US011028170B2

(12) United States Patent
Zhu et al.

(10) Patent No.: US 11,028,170 B2
(45) Date of Patent: Jun. 8, 2021

(54) INHIBITORS OF T-CELL ACTIVATION

(71) Applicant: Genzyme Corporation, Cambridge, MA (US)

(72) Inventors: Yunxiang Zhu, Cambridge, MA (US); Jozsef Karman, Framingham, MA (US); Ronnie Wei, Framingham, MA (US); Canwen Jiang, Framingham, MA (US); Seng Cheng, Framingham, MA (US)

(73) Assignee: GENZYME CORPORATION, Cambridge, MA (US)

( * ) Notice: Subject to any disclaimer, the term of this patent is extended or adjusted under 35 U.S.C. 154(b) by 342 days.

(21) Appl. No.: 15/788,433

(22) Filed: Oct. 19, 2017

(65) Prior Publication Data

US 2018/0030134 A1 Feb. 1, 2018

Related U.S. Application Data

(62) Division of application No. 14/128,461, filed as application No. PCT/US2012/045017 on Jun. 29, 2012, now Pat. No. 9,834,604.

(60) Provisional application No. 61/503,282, filed on Jun. 30, 2011.

(51) Int. Cl.
| | |
|---|---|
| *C07K 14/47* | (2006.01) |
| *C07K 14/705* | (2006.01) |
| *C07K 19/00* | (2006.01) |
| *A61K 38/17* | (2006.01) |
| *A61K 39/395* | (2006.01) |
| *C07K 16/28* | (2006.01) |
| *C07K 14/74* | (2006.01) |

(52) U.S. Cl.
CPC .......... *C07K 16/2803* (2013.01); *C07K 14/47* (2013.01); *C07K 14/70532* (2013.01); *C07K 14/70539* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 6,482,925 B1 | 11/2002 | El Tayar et al. | |
| 2007/0148162 A1 | 6/2007 | Bhardwaj et al. | |
| 2007/0184031 A1 | 8/2007 | Prabhakar et al. | |
| 2009/0214533 A1 | 8/2009 | Clynes | |
| 2011/0150892 A1 | 6/2011 | Thudium et al. | |

FOREIGN PATENT DOCUMENTS

| | | |
|---|---|---|
| EP | 0 194 276 B2 | 1/2002 |
| JP | 2014-522846 A | 9/2014 |
| WO | 1998/023741 A1 | 6/1998 |
| WO | 2004/078928 A2 | 9/2004 |
| WO | 2005/115419 A1 | 12/2005 |
| WO | 2006/031689 A2 | 3/2006 |
| WO | 2008/157367 A1 | 12/2008 |
| WO | 2009/105669 A2 | 8/2009 |
| WO | 2013/003761 A1 | 1/2013 |

OTHER PUBLICATIONS

Rathore (2017) Current State of Tolerance: The Holy Grail. Arch Clin Nephrol 3(2): 057-063.*
Blair et al. (1998) J Immunol 160: 12-15.*
Krummel et al. (1996) J Exp Med 182: 459-465.*
Walunas et al. (1996) J Exp Med 183: 2541-2550.*
Linsley et al. (1996) Curr Biol 6: 398-400.*
Algere et al. (2001) "T-cell regulation by CD28 and CTLA-4," Nat. Rev. Immunol. 1:220-228.
Atwell et al. (1996) "Design and expression of a stable bispecific scFv dimer with affinity for both glycophorin and N9 neuraminidase," Mol. Immunol. 33:1301-1312.
Baixeras et al. (1992) "Characterization of the lymphocyte activation gene 3-encoded protein. A new ligand for human leukocyte antigen class II antigens," J. Exp. Med. 176:327-337.
Baroja et al. (2002) "Inhibition of CTLA-4 function by the regulatory subunit of serine/threonine phosphatase 2A," J Immunol 168:5070-5078.
Bettini et al. (Aug. 26, 2011) "Cutting edge: accelerated autoimmune diabetes in the absence of LAG-3," J Immunol 187:3493-3498.
Bluestone et al. (2006) "CTLA4Ig: bridging the basic immunology with clinical application," Immunity. 24:233-238.
Butte et al. (2007) "Programmed death-1 ligand 1 interacts specifically with the B7-1 costimulatory molecule to inhibit T cell responses," Immunity. 27:111-122.
Driessens et al. (2009) "Costimulatory and coinhibitory receptors in anti-tumor immunity," Immunological Reviews. 229(1):126-144.
Fargeas et al. (1995) "Identification of residues in the V domain of CD80 (B7-1) implicated in functional interactions with CD28 and CTLA4," J. Exp. Med. 182:667-675.
Fife et al. (2006) "Inhibition of T cell activation and autoimmune diabetes using a B cell surface-linked CTLA-4 agonist," J. Clin. Invest. 116(8):2252-2261.
Freckleton et al. (2009) "Microarray Profiling of Phage-Display Selections for Rapid Mapping of Transcription Factor—DNA Interactions," PLoS Genetics. 5(4):e1000449. pp. 1-8.
Griffin et al. (2000) "Blockade of T cell activation using a surface-linked single-chain antibody to CTLA-4 (CD152)," J. Immunol. 164(9):4433-4442.
Holliger et al. (1993) "'Diabodies': small bivalent and bispecific antibody fragments," Proc. Natl. Acad. Sci. USA 90:6444-6448.
Huard et al. (1997) "Characterization of the major histocompatibility complex class II binding site on LAG-3 protein," Proc. Natl. Acad Sci. USA. 94:5744-5749.

(Continued)

*Primary Examiner* — Ilia I Ouspenski
(74) *Attorney, Agent, or Firm* — Lathrop GPM LLP; James H. Velema, Esq.

(57) ABSTRACT

The present invention provides a bispecific biologic comprising a ligand specific for CTLA-4 and a ligand specific for a pMHC complex.

16 Claims, 12 Drawing Sheets

Figure 1:
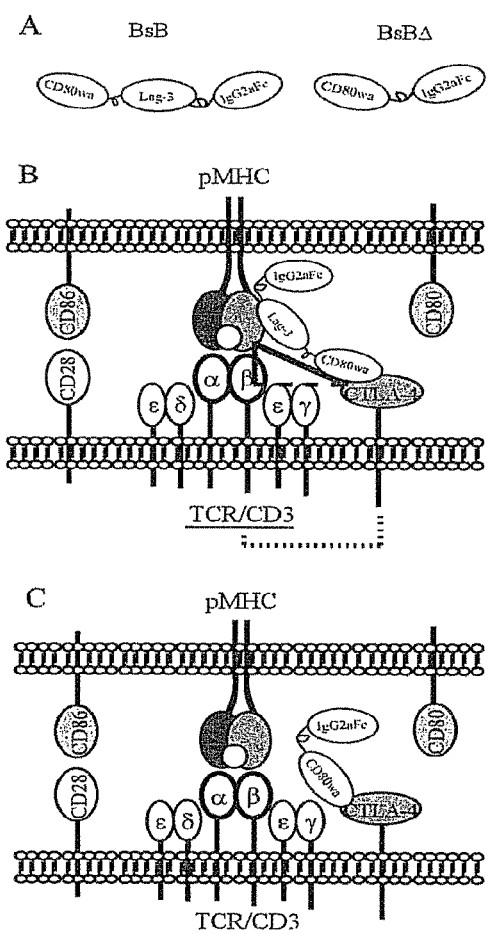

Specification includes a Sequence Listing.

(56) References Cited

OTHER PUBLICATIONS

Ise et al. (2010) "CTLA-4 suppresses the pathogenicity of self antigen-specific T cells by cell-intrinsic and cell-extrinsic mechanisms," Nat Immunol 11(2):129-135.
Kakoulidou et al. (2007) "Human Soluble CD80 is generated by alternative splicing, and recombinant soluble CD80 binds to CD28 and CD152 influencing T-cell activation," Scand. J. Immunol. 66:529-537.
Karandikar et al. (1996) "CTLA-4: a negative regulator of autoimmune disease," J Exp Med 184:783-788.
Karman et al. (Feb. 15, 2012) "Ligation of Cytotoxic T Lymphocyte Antigen-4 to T Cell Receptor Inhibits T Cell Activation and Directs Differentiation into Foxp3+ Regulatory T Cells," J. Biol. Chem. 287(14):11098-11107.
Karumuthil-Melethil (2010) "Dendritic cell-directed CTLA-4 engagement during pancreatic beta cell antigen presentation delays type 1 diabetes," J. Immunol. 184:6695-6708.
Kriangkum et al. (2001) "Bispecific and bifunctional single chain recombinant antibodies," Biomol. Eng. 18:31-40.
Lenschow et al. (1995) "Differential effects of anti-B7-1 and anti-B7-2 monoclonal antibody treatment on the development of diabetes in the nonobese diabetic mouse," J Exp Med 181:1145-1155.
Li et al. (2007) "Enhanced engagement of CTLA-4 induces antigen-specific CD4+CD25+Foxp3+ and CD4+CD25-TGF-beta 1+ adaptive regulatory T cells," J. Immunol. 179(8):5191-5203.
Liang et al. (2008) "Regulatory T cells inhibit dendritic cells by lymphocyte activation gene-3 engagement of MHC class II," J. Immunol. 180:5916-5926.
Linsley et al. (1992) "Coexpression and functional cooperation of CTLA-4 and CD28 on activated T lymphocytes," J. Exp. Med. 176:1595-1604.
Linsley et al. (1994) "Human B7-1 (CD80) and B7-2 (CD86) bind with similar avidities but distinct kinetics to CD28 and CTLA-4 receptors," Immunity 1:793-801.
Maçon-Lemaître et al. (2005) "The negative regulatory function of the lymphocyte-activation gene-3 co-receptor (CD223) on human T cells," Immunol. 115:170-178.

Onodera et al. (2009) "Constitutive expression of IDO by dendritic cells of mesenteric lymph nodes: functional involvement of the CTLA-4/B7 and CCL22/CCR4 interactions," J Immunol 183:5608-5614.
Peach et al. (1995) "Both extracellular immunoglobin-like domains of CD80 contain residues critical for binding T cell surface receptors CTLA-4 and CD28," J. Biol. Chem. 270(36):21181-21187.
Qu et al. (2009) "Remapping the type I diabetes association of the CTLA4 locus," Genes and immunity. 10(Suppl 1): S27-32.
Rao et al. (2001) "Targeted Delivery of Anti-CTLA-4 Antibody Downregulates T Cell Function in Vitro and in Vivo," Clin. Immunol. 101(2):136-145.
Ueda et al. (2003) "Association of the T-cell regulatory gene CTLA4 with susceptibility to autoimmune disease," Nature 423:506-511.
Vasu (2004) "Targeted CTLA-4 engagement induces CD4+CD25+ CTLA-4high T regulatory cells with target (allo) antigen specificity," J. Immunol. 173(4):2866-2876.
Wu et al. (1997) "CTLA-4-B7 interaction is sufficient to costimulate T cell clonal expansion," J. Exp. Med. 185(7):1327-1335.
Zhao et al. (May 21, 2013) "A Bispecific Protein Capable of Engaging CTLA-4 and MHCII Protects Non-Obese Diabetic Mice from Autoimmune Diabetes," PLOS One. 8(5):e63530. pp. 1-11.
Extended European Search Report with Search Opinion from European Patent Application No. 12804528.3, dated Jan. 9, 2015.
International Search Report with Written Opinion from International Patent Application No. PCT/US2012/045017, dated Oct. 23, 2012.
Fernando et al., "Defining the Role of the MHC in Autoimmunity: A Review and Pooled Analysis", PLoS Genetics, vol. 4, Issue 4, e1000024, Apr. 2008.
Forcione et al., "An increased risk of Crohn's disease in individuals who inherit the HLA class II DRB3*0301 allele", Proc. Natl. Acad. Sci. USA, vol. 93, pp. 5094-5098, May 1996.
Handunnetthi et al., "Regulation of major histocompatibility complex class II gene expression, genetic variation and disease", Genes and Immunity, vol. 11, pp. 99-112, 2010.
Ramagopalan et al., "Expression of the Multiple Sclerosis-Associated MHC Class II Allele HLA-DRB1*1501 Is Regulated by Vitamin D", PLoS Genetics, vol. 5, Issue 2, e1000369, Feb. 2009.

* cited by examiner

A

B

A

B

```
. . . . . . . . . . . . . . . . . . . . . . . . . . . . . . . . . . . . . . . . . . . . . . . . . . . . . . . . . . . . . . . . . . . . . . . . . . . . . .
. . . . . . . . . . . . N . . . . . N . . . . . . . . . . . . . . . . . . . . . . . . . . . . . . . . . . . . . . . . . . . . . . . . N . . . . . N . . . . .
. . . . . . . . . . . . . . . . . . . . . . . . . . N . . . . . . . . . . . . . . . . . . . . . . . . . N . . . N . . . . . . . . . . . . . . . . . . . .
. . . . . . . . . . . . . . . . . . . . . . . . . . . . . . . . . . . . . . . . . . . . . . . . . . . . . . . . . . . . . . . . . . . . . . . . . . . . . .
. . . . . . . . . . . . . . . . . . . . . . . . . . . . . . . . . . . . . . . . . . . . . . . . . . . . . . . . . . . . . . . . . . . . . . . . . . . . . .
. . . N . . . . . . . . . . . . . . . . . . . . . . . . . . . . . . . . . . . . . . . . . . . . . . . . . . . . . . . . . . N . . . . . . . . . . . . . . .
. . . . . . . . . . . . . . . . . . . . . . . . . . . . . . . . . . . . . . . . . . . . . . . . . . . . . . . . . . . . . . . . . . . . . . . . . . . . . .
. N . . . . . . . . . . . . . . . . . . . . . . . . . . . . . . . . . . . . . . . . . . . . . . . . . . . . . . . . . . . . . . . . . . . . . . . . . . . .
. . . . . . . . . . . . . . . . . . . . . . . . . . . . . . . . . . . . . . . . . . . . . . . . . . . . . . . . . . . . . . . . . . . . . . . . . . . . . .
```

| Sugars/BsB | Fuc | GlcNAc | Gal | Man | Sialic acid | Sialic acid/Gal ratio |
|---|---|---|---|---|---|---|
| Mol/Mol | 8.0 ± 0.6 | 37.1 ± 2.2 | 28.5 ± 1.1 | 36.8±2.6 | 19.3 ± 0.7 | 0.68 |

Figure 9

A

B

A

B

A

B

SEQUENCE LISTING

<160> NUMBER OF SEQ ID NOS: 17

<210> SEQ ID NO 1
<211> LENGTH: 2160
<212> TYPE: DNA
<213> ORGANISM: Artificial Sequence
<220> FEATURE:
<223> OTHER INFORMATION: Nucleotide sequence of mouse surrogate
      construct (Gene1)

<400> SEQUENCE: 1

```
atggcttgca attgtcagtt gatgcaggat acaccactcc tcaagtttcc atgtccaagg      60
ctcattcttc tctttgtgct gctgattcgt ctttcacaag tgtcttcaga tgttgatgaa     120
caactgtcca agtcagtgaa agataaggta ttgctgcctt gccgttacaa ctctcctcat     180
```

| | |
|---|---|
| gaagatgagt ctgaagaccg aatctactgg caaaaacatg acaaagtggt gctgtctgtc | 240 |
| attgctggga aactaaaagt ggcgcccgag tataagaacc ggactttata tgacaacact | 300 |
| acctactctc ttatcatcct gggcctggtc ctttcagacc ggggcacata cagctgtgtc | 360 |
| gttcaaaaga aggaaagagg aacgtatgaa gttaaacact tggctttagt aaagttgtcc | 420 |
| atcaaagctg acttctctac ccccaacata actgagtctg aaacccatc tgcagacact | 480 |
| aaaaggatta cctgctttgc ttccgggggt ttcccaaagc ctcgcttctc ttggttggaa | 540 |
| aatggaagag aattacctgg catcaatacg acaatttccc aggatcctga atctgaattg | 600 |
| tacaccatta gtagccaact agatttcaat acgactcgca accacaccat taagtgtctc | 660 |
| attaaatatg gagatgctca cgtgtcagag gacttcacct gggagcccag agggcccaca | 720 |
| atcaagccct gtcctccatg caaatgccca gcacctaacc tcttgggtgg accatccgtc | 780 |
| ttcatcttcc ctccaaagat caaggatgta ctcatgatct ccctgagccc catggtcaca | 840 |
| tgtgtggtgg tggatgtgag cgaggatgac ccagatgtcc agatcagctg gttcgtgaac | 900 |
| aacgtggaag tactcacagc tcagacacaa acccatagag aggattacaa cagtactctc | 960 |
| cgggtggtca gtgccctccc catccagcac caggactgga tgagtggcaa ggagttcaaa | 1020 |
| tgcaaggtca caacaaagc cctcccagcg cccatcgaga gaaccatctc aaaacccaaa | 1080 |
| gggtcagtaa gagctccaca ggtatatgtc ttgcctccac cagaagaaga tgactaag | 1140 |
| aaacaggtca ctctgacctg catggtcaca gacttcatgc ctgaagacat ttacgtggag | 1200 |
| tggaccaaca cgggaaaac agagctaaac tacaagaaca ctgaaccagt cctggactct | 1260 |
| gatggttctt acttcatgta cagcaagctg agagtggaaa agaagaactg ggtggaaaga | 1320 |
| aatagctact cctgctcagt ggtccacgag ggtctgcaca atcaccacac gactaagagc | 1380 |
| ttctccccgga ctccgggtaa aggcggtggc ggcggaggcg gtggcggtgg gcctgggaaa | 1440 |
| gagctccccg tggtgtgggc ccaggaggga gctcccgtcc atcttccctg cagcctcaaa | 1500 |
| tcccccaacc tggatcctaa ctttctacga agaggagggg ttatctggca acatcaacca | 1560 |
| gacagtggcc aacccactcc catcccggcc cttgaccttc accaggggat gccctcgcct | 1620 |
| agacaacccg cacccggtcg ctacacggtg ctgagcgtgg ctccaggagg cctgcgcagc | 1680 |
| gggaggcagc ccctgcatcc ccacgtgcag ctggaggagc gcggcctcca gcgcgggac | 1740 |
| ttctctctgt ggttgcgccc agctctgcgc accgatgcgg gcgagtacca cgccaccgtg | 1800 |
| cgcctcccga accgcgccct ctcctgcagt ctccgcctgc gcgtcggcca ggcctcgatg | 1860 |
| attgctagtc cctcaggagt cctcaagctg tctgattggg tccttttgaa ctgctccttc | 1920 |
| agccgtcctg accgccagt ctctgtgcac tggttccagg gccagaaccg agtgcctgtc | 1980 |
| tacaactcac cgcgtcattt tttagctgaa actttcctgt tactgcccca agtcagcccc | 2040 |
| ctggactctg ggacctgggg ctgtgtcctc acctacagag atggcttcaa tgtctccatc | 2100 |
| acgtacaacc tcaaggttct gggtctggag cccgtagccc accatcacca tcatcactga | 2160 |

<210> SEQ ID NO 2
<211> LENGTH: 719
<212> TYPE: PRT
<213> ORGANISM: Artificial Sequence
<220> FEATURE:
<223> OTHER INFORMATION: Translated protein sequence of mouse surrogate
      construct (Gene1)

<400> SEQUENCE: 2

Met Ala Cys Asn Cys Gln Leu Met Gln Asp Thr Pro Leu Leu Lys Phe
1               5                   10                  15

```
Pro Cys Pro Arg Leu Ile Leu Leu Phe Val Leu Leu Ile Arg Leu Ser
            20                  25                  30

Gln Val Ser Ser Asp Val Asp Glu Gln Leu Ser Lys Ser Val Lys Asp
        35                  40                  45

Lys Val Leu Leu Pro Cys Arg Tyr Asn Ser Pro His Glu Asp Glu Ser
    50                  55                  60

Glu Asp Arg Ile Tyr Trp Gln Lys His Asp Lys Val Val Leu Ser Val
65                  70                  75                  80

Ile Ala Gly Lys Leu Lys Val Ala Pro Glu Tyr Lys Asn Arg Thr Leu
                85                  90                  95

Tyr Asp Asn Thr Thr Tyr Ser Leu Ile Ile Leu Gly Leu Val Leu Ser
            100                 105                 110

Asp Arg Gly Thr Tyr Ser Cys Val Val Gln Lys Lys Glu Arg Gly Thr
        115                 120                 125

Tyr Glu Val Lys His Leu Ala Leu Val Lys Leu Ser Ile Lys Ala Asp
    130                 135                 140

Phe Ser Thr Pro Asn Ile Thr Glu Ser Gly Asn Pro Ser Ala Asp Thr
145                 150                 155                 160

Lys Arg Ile Thr Cys Phe Ala Ser Gly Gly Phe Pro Lys Pro Arg Phe
                165                 170                 175

Ser Trp Leu Glu Asn Gly Arg Glu Leu Pro Gly Ile Asn Thr Thr Ile
            180                 185                 190

Ser Gln Asp Pro Glu Ser Glu Leu Tyr Thr Ile Ser Ser Gln Leu Asp
        195                 200                 205

Phe Asn Thr Thr Arg Asn His Thr Ile Lys Cys Leu Ile Lys Tyr Gly
    210                 215                 220

Asp Ala His Val Ser Glu Asp Phe Thr Trp Glu Pro Arg Gly Pro Thr
225                 230                 235                 240

Ile Lys Pro Cys Pro Pro Cys Lys Cys Pro Ala Pro Asn Leu Leu Gly
                245                 250                 255

Gly Pro Ser Val Phe Ile Phe Pro Pro Lys Ile Lys Asp Val Leu Met
            260                 265                 270

Ile Ser Leu Ser Pro Met Val Thr Cys Val Val Asp Val Ser Glu
        275                 280                 285

Asp Asp Pro Asp Val Gln Ile Ser Trp Phe Val Asn Asn Val Glu Val
290                 295                 300

Leu Thr Ala Gln Thr Gln Thr His Arg Glu Asp Tyr Asn Ser Thr Leu
305                 310                 315                 320

Arg Val Val Ser Ala Leu Pro Ile Gln His Gln Asp Trp Met Ser Gly
                325                 330                 335

Lys Glu Phe Lys Cys Lys Val Asn Asn Lys Ala Leu Pro Ala Pro Ile
            340                 345                 350

Glu Arg Thr Ile Ser Lys Pro Lys Gly Ser Val Arg Ala Pro Gln Val
        355                 360                 365

Tyr Val Leu Pro Pro Pro Glu Glu Glu Met Thr Lys Lys Gln Val Thr
    370                 375                 380

Leu Thr Cys Met Val Thr Asp Phe Met Pro Glu Asp Ile Tyr Val Glu
385                 390                 395                 400

Trp Thr Asn Asn Gly Lys Thr Glu Leu Asn Tyr Lys Asn Thr Glu Pro
                405                 410                 415

Val Leu Asp Ser Asp Gly Ser Tyr Phe Met Tyr Ser Lys Leu Arg Val
            420                 425                 430
```

Glu Lys Lys Asn Trp Val Glu Arg Asn Ser Tyr Ser Cys Ser Val Val
            435                 440                 445

His Glu Gly Leu His Asn His His Thr Thr Lys Ser Phe Ser Arg Thr
    450                 455                 460

Pro Gly Lys Gly Gly Gly Gly Gly Gly Gly Gly Pro Gly Lys
465                 470                 475                 480

Glu Leu Pro Val Val Trp Ala Gln Glu Gly Ala Pro Val His Leu Pro
                485                 490                 495

Cys Ser Leu Lys Ser Pro Asn Leu Asp Pro Asn Phe Leu Arg Arg Gly
            500                 505                 510

Gly Val Ile Trp Gln His Gln Pro Asp Ser Gly Gln Pro Thr Pro Ile
        515                 520                 525

Pro Ala Leu Asp Leu His Gln Gly Met Pro Ser Pro Arg Gln Pro Ala
    530                 535                 540

Pro Gly Arg Tyr Thr Val Leu Ser Val Ala Pro Gly Gly Leu Arg Ser
545                 550                 555                 560

Gly Arg Gln Pro Leu His Pro His Val Gln Leu Glu Glu Arg Gly Leu
                565                 570                 575

Gln Arg Gly Asp Phe Ser Leu Trp Leu Arg Pro Ala Leu Arg Thr Asp
            580                 585                 590

Ala Gly Glu Tyr His Ala Thr Val Arg Leu Pro Asn Arg Ala Leu Ser
        595                 600                 605

Cys Ser Leu Arg Leu Arg Val Gly Gln Ala Ser Met Ile Ala Ser Pro
    610                 615                 620

Ser Gly Val Leu Lys Leu Ser Asp Trp Val Leu Leu Asn Cys Ser Phe
625                 630                 635                 640

Ser Arg Pro Asp Arg Pro Val Ser Val His Trp Phe Gln Gly Gln Asn
                645                 650                 655

Arg Val Pro Val Tyr Asn Ser Pro Arg His Phe Leu Ala Glu Thr Phe
            660                 665                 670

Leu Leu Leu Pro Gln Val Ser Pro Leu Asp Ser Gly Thr Trp Gly Cys
        675                 680                 685

Val Leu Thr Tyr Arg Asp Gly Phe Asn Val Ser Ile Thr Tyr Asn Leu
    690                 695                 700

Lys Val Leu Gly Leu Glu Pro Val Ala His His His His His
705                 710                 715

<210> SEQ ID NO 3
<211> LENGTH: 2139
<212> TYPE: DNA
<213> ORGANISM: Artificial Sequence
<220> FEATURE:
<223> OTHER INFORMATION: Nucleotide sequence of mouse surrogate
      construct (Gene 2)

<400> SEQUENCE: 3
atggcttgca attgtcagtt gatgcaggat acaccactcc tcaagtttcc atgtccaagg      60
ctcattcttc tctttgtgct gctgattcgt ctttcacaag tgtcttcaga tgttgatgaa     120
caactgtcca gtcagtgaa agataaggta ttgctgcctt gccgttacaa ctctcctcat     180
gaagatgagt ctgaagaccg aatctactgg caaaaacatg acaaagtggt gctgtctgtc     240
attgctggga actaaaagt ggcgcccgag tataagaacc ggactttata tgacaacact     300
acctactctc ttatcatcct gggcctggtc ctttcagacc ggggcacata cagctgtgtc     360
gttcaaaaga aggaaagagg aacgtatgaa gttaaacact tggctttagt aaagtttgtcc     420

| | |
|---|---|
| atcaaagctg acttctctac ccccaacata actgagtctg aaacccatc tgcagacact | 480 |
| aaaaggatta cctgctttgc ttccgggggt ttcccaaagc ctcgcttctc ttggttggaa | 540 |
| aatggaagag aattacctgg catcaatacg acaatttccc aggatcctga atctgaattg | 600 |
| tacaccatta gtagccaact agatttcaat acgactcgca accacaccat taagtgtctc | 660 |
| attaaatatg gagatgctca cgtgtcagag gacttcacct ggggcggtgg cggcggaggc | 720 |
| ggtggcggtg ggcctgggaa agagctcccc gtggtgtggg cccaggaggg agctcccgtc | 780 |
| catcttccct gcagcctcaa atcccccaac ctggatccta actttctacg aagaggaggg | 840 |
| gttatctggc aacatcaacc agacagtggc caacccactc ccatcccggc ccttgacctt | 900 |
| caccagggga tgccctcgcc tagacaaccc gcaccggtc gctacacggt gctgagcgtg | 960 |
| gctccaggag gcctgcgcag cgggaggcag cccctgcatc cccacgtgca gctggaggag | 1020 |
| cgcggcctcc agcgcgggga cttctctctg tggttgcgcc cagctctgcg caccgatgcg | 1080 |
| ggcgagtacc acgccaccgt gcgcctcccg aaccgcgccc tctcctgcag tctccgcctg | 1140 |
| cgcgtcggcc aggcctcgat gattgctagt ccctcaggag tcctcaagct gtctgattgg | 1200 |
| gtccttttga actgctcctt cagccgtcct gaccgcccag tctctgtgca ctggttccag | 1260 |
| ggccagaacc gagtgcctgt ctacaactca ccgcgtcatt ttttagctga aacttttcctg | 1320 |
| ttactgcccc aagtcagccc cctggactct gggacctggg gctgtgtcct cacctacaga | 1380 |
| gatggcttca atgtctccat cacgtacaac ctcaaggttc tgggtctgga gcccgtagcc | 1440 |
| cccagagggc ccacaatcaa gccctgtcct ccatgcaaat gcccagcacc taacctcttg | 1500 |
| ggtggaccat ccgtcttcat cttccctcca aagatcaagg atgtactcat gatctccctg | 1560 |
| agccccatgg tcacatgtgt ggtggtggat gtgagcgagg atgacccaga tgtccagatc | 1620 |
| agctggttcg tgaacaacgt ggaagtactc acagctcaga cacaaaccca tagagaggat | 1680 |
| tacaacagta ctctccgggt ggtcagtgcc ctccccatcc agcaccagga ctggatgagt | 1740 |
| ggcaaggagt tcaaatgcaa ggtcaacaac aaagccctcc cagcgcccat cgagagaacc | 1800 |
| atctcaaaac ccaaagggtc agtaagagct ccacaggtat atgtcttgcc tccaccagaa | 1860 |
| gaagagatga ctaagaaaca ggtcactctg acctgcatgg tcacagactt catgcctgaa | 1920 |
| gacatttacg tggagtggac caacaacggg aaaacagagc taaactacaa gaacactgaa | 1980 |
| ccagtcctgg actctgatgg ttcttacttc atgtacagca agctgagagt ggaaaagaag | 2040 |
| aactgggtgg aaagaaatag ctactcctgc tcagtggtcc acgagggtct gcacaatcac | 2100 |
| cacacgacta gagcttctc ccggactccg ggtaaatga | 2139 |

<210> SEQ ID NO 4
<211> LENGTH: 712
<212> TYPE: PRT
<213> ORGANISM: Artificial Sequence
<220> FEATURE:
<223> OTHER INFORMATION: Translated protein sequence of mouse surrogate
      construct (Gene 2)

<400> SEQUENCE: 4

Met Ala Cys Asn Cys Gln Leu Met Gln Asp Thr Pro Leu Leu Lys Phe
1               5                   10                  15

Pro Cys Pro Arg Leu Ile Leu Leu Phe Val Leu Leu Ile Arg Leu Ser
            20                  25                  30

Gln Val Ser Ser Asp Val Asp Glu Gln Leu Ser Lys Ser Val Lys Asp
        35                  40                  45

Lys Val Leu Leu Pro Cys Arg Tyr Asn Ser Pro His Glu Asp Glu Ser

```
            50                  55                  60
Glu Asp Arg Ile Tyr Trp Gln Lys His Asp Lys Val Val Leu Ser Val
 65                  70                  75                  80

Ile Ala Gly Lys Leu Lys Val Ala Pro Glu Tyr Lys Asn Arg Thr Leu
                 85                  90                  95

Tyr Asp Asn Thr Thr Tyr Ser Leu Ile Leu Gly Leu Val Leu Ser
                100                 105                 110

Asp Arg Gly Thr Tyr Ser Cys Val Val Gln Lys Lys Glu Arg Gly Thr
                115                 120                 125

Tyr Glu Val Lys His Leu Ala Leu Val Lys Leu Ser Ile Lys Ala Asp
                130                 135                 140

Phe Ser Thr Pro Asn Ile Thr Glu Ser Gly Asn Pro Ser Ala Asp Thr
145                 150                 155                 160

Lys Arg Ile Thr Cys Phe Ala Ser Gly Gly Phe Pro Lys Pro Arg Phe
                165                 170                 175

Ser Trp Leu Glu Asn Gly Arg Glu Leu Pro Gly Ile Asn Thr Thr Ile
                180                 185                 190

Ser Gln Asp Pro Glu Ser Glu Leu Tyr Thr Ile Ser Ser Gln Leu Asp
                195                 200                 205

Phe Asn Thr Thr Arg Asn His Thr Ile Lys Cys Leu Ile Lys Tyr Gly
                210                 215                 220

Asp Ala His Val Ser Glu Asp Phe Thr Trp Gly Gly Gly Gly Gly
225                 230                 235                 240

Gly Gly Gly Gly Pro Gly Lys Glu Leu Pro Val Val Trp Ala Gln Glu
                245                 250                 255

Gly Ala Pro Val His Leu Pro Cys Ser Leu Lys Ser Pro Asn Leu Asp
                260                 265                 270

Pro Asn Phe Leu Arg Arg Gly Gly Val Ile Trp Gln His Gln Pro Asp
                275                 280                 285

Ser Gly Gln Pro Thr Pro Ile Pro Ala Leu Asp Leu His Gln Gly Met
                290                 295                 300

Pro Ser Pro Arg Gln Pro Ala Pro Gly Arg Tyr Thr Val Leu Ser Val
305                 310                 315                 320

Ala Pro Gly Gly Leu Arg Ser Gly Arg Gln Pro Leu His Pro His Val
                325                 330                 335

Gln Leu Glu Glu Arg Gly Leu Gln Arg Gly Asp Phe Ser Leu Trp Leu
                340                 345                 350

Arg Pro Ala Leu Arg Thr Asp Ala Gly Glu Tyr His Ala Thr Val Arg
                355                 360                 365

Leu Pro Asn Arg Ala Leu Ser Cys Ser Leu Arg Leu Arg Val Gly Gln
370                 375                 380

Ala Ser Met Ile Ala Ser Pro Ser Gly Val Leu Lys Leu Ser Asp Trp
385                 390                 395                 400

Val Leu Leu Asn Cys Ser Phe Ser Arg Pro Asp Arg Pro Val Ser Val
                405                 410                 415

His Trp Phe Gln Gly Gln Asn Arg Val Pro Val Tyr Asn Ser Pro Arg
                420                 425                 430

His Phe Leu Ala Glu Thr Phe Leu Leu Leu Pro Gln Val Ser Pro Leu
                435                 440                 445

Asp Ser Gly Thr Trp Gly Cys Val Leu Thr Tyr Arg Asp Gly Phe Asn
                450                 455                 460

Val Ser Ile Thr Tyr Asn Leu Lys Val Leu Gly Leu Glu Pro Val Ala
465                 470                 475                 480
```

Pro Arg Gly Pro Thr Ile Lys Pro Cys Pro Cys Lys Cys Pro Ala
              485                 490                 495

Pro Asn Leu Leu Gly Gly Pro Ser Val Phe Ile Phe Pro Pro Lys Ile
          500                 505                 510

Lys Asp Val Leu Met Ile Ser Leu Ser Pro Met Val Thr Cys Val Val
          515                 520                 525

Val Asp Val Ser Glu Asp Asp Pro Asp Val Gln Ile Ser Trp Phe Val
      530                 535                 540

Asn Asn Val Glu Val Leu Thr Ala Gln Thr Gln Thr His Arg Glu Asp
545                 550                 555                 560

Tyr Asn Ser Thr Leu Arg Val Val Ser Ala Leu Pro Ile Gln His Gln
              565                 570                 575

Asp Trp Met Ser Gly Lys Glu Phe Lys Cys Lys Val Asn Asn Lys Ala
          580                 585                 590

Leu Pro Ala Pro Ile Glu Arg Thr Ile Ser Lys Pro Lys Gly Ser Val
          595                 600                 605

Arg Ala Pro Gln Val Tyr Val Leu Pro Pro Glu Glu Glu Met Thr
      610                 615                 620

Lys Lys Gln Val Thr Leu Thr Cys Met Val Thr Asp Phe Met Pro Glu
625                 630                 635                 640

Asp Ile Tyr Val Glu Trp Thr Asn Asn Gly Lys Thr Glu Leu Asn Tyr
              645                 650                 655

Lys Asn Thr Glu Pro Val Leu Asp Ser Asp Gly Ser Tyr Phe Met Tyr
          660                 665                 670

Ser Lys Leu Arg Val Glu Lys Lys Asn Trp Val Glu Arg Asn Ser Tyr
          675                 680                 685

Ser Cys Ser Val Val His Glu Gly Leu His Asn His His Thr Thr Lys
      690                 695                 700

Ser Phe Ser Arg Thr Pro Gly Lys
705                 710

<210> SEQ ID NO 5
<211> LENGTH: 2160
<212> TYPE: DNA
<213> ORGANISM: Artificial Sequence
<220> FEATURE:
<223> OTHER INFORMATION: CTLA-4 BsB human construct wildtype nucleotide
      sequence

<400> SEQUENCE: 5
atgggccaca cacggaggca gggaacatca ccatccaagt gtccatacct caatttcttt      60
cagctcttgg tgctggctgg tctttctcac ttctgttcag gtgttatcca cgtgaccaag     120
gaagtgaaaa aagtggcaac gctgtcctgt ggtcacaatg tttctgttga agagctggca     180
caaactcgca tctactggca aaaggagaag aaaatggtgc tgactatgat gtctggggac     240
atgaatatat ggcccgagta caagaaccgg accatctttg atatcactaa taacctctcc     300
attgtgatcc tggctctgcg cccatctgac gagggcacat acgagtgtgt tgttctgaag     360
tatgaaaaag acgctttcaa gcgggaacac ctggctgaag tgacgttatc agtcaaagct     420
gacttcccta cacctagtat atctgacttt gaaattccaa cttctaatat tagaaggata     480
atttgctcaa cctctggagg ttttccagag cctcacctct cctggttgga aaatggagaa     540
gaattaaatg ccatcaacac aacagtttcc caagatcctg aaactgagct ctatgctgtt     600
agcagcaaac tggatttcaa tatgacaacc aaccacagct tcatgtgtct catcaagtat     660

```
ggacatttaa gagtgaatca gaccttcaac tggaatacaa ccggcggtgg cggcggaggc    720
ggtggcggtt ccggagctga ggtcccggtg gtgtgggccc aggaggggggc tcctgcccag    780
ctcccctgca gccccacaat cccctccag gatctcagcc ttctgcgaag agcagggggtc    840
acttggcagc atcagccaga cagtggcccg cccgctgccg ccccggcca tcccctggcc    900
cccggccctc accggcggc gccctcctcc tgggggccca ggccccgccg ctacacggtg    960
ctgagcgtgg gtcccggagg cctgcgcagc gggaggctgc cctgcagcc cgcgtccag    1020
ctggatgagc gcggccggca gcgcggggac ttctcgctat ggctgcgccc agcccggcgc    1080
gcggacgccg gcgagtaccg cgccgcggtg cacctcaggg accgcgccct tcctgccgc    1140
ctccgtctgc gcctgggcca ggcctcgatg actgccagcc cccaggatc tctcagagcc    1200
tccgactggg tcattttgaa ctgctccttc agccgccctg accgcccagc ctctgtgcat    1260
tggtttcgga accggggcca gggccgagtc cctgtccggg agtcccccca tcaccactta    1320
gcggaaagct tcctcttcct gccccaagtc agccccatgg actctgggcc ctggggctgc    1380
atcctcacct acagagatgg cttcaacgtc tccatcatgt ataacctcac tgttctgggt    1440
ctgctggtgc cccggggctc cgagcccaaa tcttgtgaca aaactcacac atgcccaccg    1500
tgcccagcac ctgaactcct gggggaccg tcagtcttcc tcttcccccc aaaacccaag    1560
gacaccctca tgatctcccg gaccctgag gtcacatgcg tggtggtgga cgtgagccac    1620
gaagaccctg aggtcaagtt caactggtac gtggacggcg tggaggtgca taatgccaag    1680
acaaagccgc gggaggagca gtacaacagc acgtaccgtg tggtcagcgt cctcaccgtc    1740
ctgcaccagg actggctgaa tggcaaggag tacaagtgca aggtctccaa caaagccctc    1800
ccagcccca tcgagaaaac catctccaaa gccaagggc agccccgaga accacaggtg    1860
tacaccctgc cccatctcg ggatgagctg accaagaacc aggtcagcct gacctgcctg    1920
gtcaaaggct tctatcccag cgacatcgcc gtggagtggg agagcaatgg gcagccggag    1980
aacaactaca agaccacgcc tcccgtgctg gactccgacg gctccttctt cctatacagc    2040
aagctcaccg tggacaagag caggtggcag caggggaacg tcttctcatg ctccgtgatg    2100
catgaggctc tgcacaacca ctacacgcag aagagcctct ccctgtctcc gggtaaatga    2160
```

<210> SEQ ID NO 6
<211> LENGTH: 719
<212> TYPE: PRT
<213> ORGANISM: Artificial Sequence
<220> FEATURE:
<223> OTHER INFORMATION: CTLA-4 BsB human construct wildtype translated
      protein sequence

<400> SEQUENCE: 6

```
Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95
```

```
Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
            115                 120                 125

Glu His Leu Ala Glu Val Thr Leu Ser Val Lys Ala Asp Phe Pro Thr
        130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
210                 215                 220

Val Asn Gln Thr Phe Asn Trp Asn Thr Thr Gly Gly Gly Gly Gly Gly
225                 230                 235                 240

Gly Gly Gly Ser Gly Ala Glu Val Pro Trp Trp Ala Gln Glu Gly Ala
                245                 250                 255

Pro Ala Gln Leu Pro Cys Ser Pro Thr Ile Pro Leu Gln Asp Leu Ser
            260                 265                 270

Leu Leu Arg Arg Ala Gly Val Thr Trp Gln His Gln Pro Asp Ser Gly
            275                 280                 285

Pro Pro Ala Ala Ala Pro Gly His Pro Leu Ala Pro Gly Pro His Pro
290                 295                 300

Ala Ala Pro Ser Ser Trp Gly Pro Arg Pro Arg Arg Tyr Thr Val Leu
305                 310                 315                 320

Ser Val Gly Pro Gly Gly Leu Arg Ser Gly Arg Leu Pro Leu Gln Pro
            325                 330                 335

Arg Val Gln Leu Asp Glu Arg Gly Arg Gln Arg Gly Asp Phe Ser Leu
            340                 345                 350

Trp Leu Arg Pro Ala Arg Arg Ala Asp Ala Gly Glu Tyr Arg Ala Ala
            355                 360                 365

Val His Leu Arg Asp Arg Ala Leu Ser Cys Arg Leu Arg Leu Arg Leu
        370                 375                 380

Gly Gln Ala Ser Met Thr Ala Ser Pro Pro Gly Ser Leu Arg Ala Ser
385                 390                 395                 400

Asp Val Val Val Ile Leu Asn Cys Ser Phe Ser Arg Pro Asp Arg Pro
                405                 410                 415

Ala Ser Val His Trp Phe Arg Asn Arg Gly Gln Gly Arg Val Pro Val
            420                 425                 430

Arg Glu Ser Pro His His His Leu Ala Glu Ser Phe Leu Phe Leu Pro
        435                 440                 445

Gln Val Ser Pro Met Asp Ser Gly Pro Trp Gly Cys Ile Leu Thr Tyr
    450                 455                 460

Arg Asp Gly Phe Asn Val Ser Ile Met Tyr Asn Leu Thr Val Leu Gly
465                 470                 475                 480

Leu Leu Val Pro Arg Gly Ser Glu Pro Lys Ser Cys Asp Lys Thr His
                485                 490                 495

Thr Cys Pro Pro Cys Pro Ala Pro Glu Leu Leu Gly Gly Pro Ser Val
        500                 505                 510

Phe Leu Phe Pro Pro Lys Pro Lys Asp Thr Leu Met Ile Ser Arg Thr
```

```
            515                 520                 525
Pro Glu Val Thr Cys Val Val Asp Val Ser His Glu Asp Pro Glu
530                 535                 540

Val Lys Phe Asn Trp Tyr Val Asp Gly Val Glu Val His Asn Ala Lys
545                 550                 555                 560

Thr Lys Pro Arg Glu Glu Gln Tyr Asn Ser Thr Tyr Arg Val Val Ser
                565                 570                 575

Val Leu Thr Val Leu His Gln Asp Trp Leu Asn Gly Lys Glu Tyr Lys
            580                 585                 590

Cys Lys Val Ser Asn Lys Ala Leu Pro Ala Pro Ile Glu Lys Thr Ile
                595                 600                 605

Ser Lys Ala Lys Gly Gln Pro Arg Glu Pro Gln Val Tyr Thr Leu Pro
610                 615                 620

Pro Ser Arg Asp Glu Leu Thr Lys Asn Gln Val Ser Leu Thr Cys Leu
625                 630                 635                 640

Val Lys Gly Phe Tyr Pro Ser Asp Ile Ala Val Glu Trp Ser Asn
                645                 650                 655

Gly Gln Pro Glu Asn Asn Tyr Lys Thr Thr Pro Pro Val Leu Asp Ser
                660                 665                 670

Asp Gly Ser Phe Phe Leu Tyr Ser Lys Leu Thr Val Asp Lys Ser Arg
                675                 680                 685

Trp Gln Gln Gly Asn Val Phe Ser Cys Ser Val Met His Glu Ala Leu
690                 695                 700

His Asn His Tyr Thr Gln Lys Ser Leu Ser Leu Ser Pro Gly Lys
705                 710                 715

<210> SEQ ID NO 7
<211> LENGTH: 2160
<212> TYPE: DNA
<213> ORGANISM: Artificial Sequence
<220> FEATURE:
<223> OTHER INFORMATION: CTLA-4 BsB human construct variant nucleotide
      sequence 1

<400> SEQUENCE: 7
atgggccaca cacggaggca gggaacatca ccatccaagt gtccatacct caatttcttt      60
cagctcttgg tgctggctgg tctttctcac ttctgttcag gtgttatcca cgtgaccaag     120
gaagtgaaag aagtggcaac gctgtcctgt ggtcacaatg tttctgttga agagctggca     180
caaactcgca tctactggca aaaggagaag aaaatggtgc tgactatgat gtctggggac     240
atgaatatag cccccgagta caagaaccgg accatctttg atatcactaa taacctctcc     300
attgtgatcc tggctctgcg cccatctgac gagggcacat acgagtgtgt tgttctgaag     360
tatgaaaaag acgctttcaa gcgggaacac ctggctgaag tgacgttatc agtcaaagct     420
gacttcccta cacctagtat atctgacttt gaaattccaa cttctaatat tagaaggata     480
atttgctcaa cctctggagg ttttccagag cctcacctct cctggttgga aaatggagaa     540
gaattaaatg ccatcaacac aacagttgcc caagatcctg aaactgagct ctatgctgtt     600
agcagcaaac tggatttcaa tatgacaacc aaccacagct tcatgtgtct catcaagtat     660
ggacatttaa gagtgaatca gaccttcaac tggaatacaa ccggcggtgg cggcggaggc     720
ggtggcggtt ccggagctga ggtcccggtg gtgtgggccc aggaggggc tcctgcccag     780 ctcccctgca gccccacaat cccctccag gatctcagcc ttctgcgaag agcagggtc     840 acttggcagc atcagccaga cagtggcccg ccgctgccg cccccggcca tcccctggcc     900
```

```
cccggccctc acccggcggc gccctcctcc tggggggccca ggcccgagcg ctacacggtg      960
ctgagcgtgg gtcccggagg cctgcgcagc gggaggctgc ccctgcagcc cgcgtccag     1020
ctggatgagc gcggccggca gcgcggggac ttctcgctat ggctgcgccc agcccggcgc     1080
gcggacgccg gcgagtaccg cgccgcggtg cacctcaggg accgcgccct tcctgccgc     1140
ctccgtctgc gcctgggcca ggcctcgatg actgccagcc ccccaggatc tctcagagcc     1200
tccgactggg tcattttgaa ctgctccttc agccgccctg accgccagc ctctgtgcat      1260
tggtttcgga accggggcca gggccgagtc cctgtccggg agtcccccca tcaccactta     1320
gcggaaagct tcctcttcct gccccaagtc agccccatgg actctgggcc tggggctgc      1380
atcctcacct acagagatgg cttcaacgtc tccatcatgt ataacctcac tgttctgggt     1440
ctgctggtgc cccggggctc cgagcccaaa tcttgtgaca aaactcacac aagcccaccg     1500
agcccagcac ctgaactcct ggggggatcc tcagtcttcc tcttcccccc aaaacccaag     1560
gacaccctca tgatctcccg gacccctgag gtcacatgcg tggtggtgga cgtgagccac     1620
gaagaccctg aggtcaagtt caactggtac gtggacggcg tggaggtgca taatgccaag     1680
acaaagccgc gggaggagca gtaccagagc acgtaccgtg tggtcagcgt cctcaccgtc     1740
ctgcaccagg actggctgaa tggcaaggag tacaagtgca aggtctccaa caaagccctc     1800
ccagccccca tcgagaaaac catctccaaa gccaaagggc agccccgaga accacaggtg     1860
tacaccctgc cccatctcg ggatgagctg accaagaacc aggtcagcct gacctgcctg      1920
gtcaaaggct tctatcccag cgacatcgcc gtggagtggg agagcaatgg gcagccggag     1980
aacaactaca agaccacgcc tcccgtgctg gactccgacg gctccttctt cctatacagc     2040
aagctcaccg tggacaagag caggtggcag caggggaacg tcttctcatg ctccgtgatg     2100
catgaggctc tgcacaacca ctacacgcag aagagcctct ccctgtctcc gggtaaatga    2160
```

```
<210> SEQ ID NO 8
<211> LENGTH: 719
<212> TYPE: PRT
<213> ORGANISM: Artificial Sequence
<220> FEATURE:
<223> OTHER INFORMATION: CTLA-4 BsB human construct variant translated
      protein sequence 1

<400> SEQUENCE: 8

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Ala Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140
```

```
Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ala Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Gly Gly Gly Gly Gly Gly
225                 230                 235                 240

Gly Gly Gly Ser Gly Ala Glu Val Pro Val Val Trp Ala Gln Glu Gly
                245                 250                 255

Ala Pro Ala Gln Leu Pro Cys Ser Pro Thr Ile Pro Leu Gln Asp Leu
            260                 265                 270

Ser Leu Leu Arg Arg Ala Gly Val Thr Trp Gln His Gln Pro Asp Ser
        275                 280                 285

Gly Pro Pro Ala Ala Ala Pro Gly His Pro Leu Ala Pro Gly Pro His
    290                 295                 300

Pro Ala Ala Pro Ser Ser Trp Gly Pro Arg Pro Glu Arg Tyr Thr Val
305                 310                 315                 320

Leu Ser Val Gly Pro Gly Gly Leu Arg Ser Gly Arg Leu Pro Leu Gln
                325                 330                 335

Pro Arg Val Gln Leu Asp Glu Arg Gly Arg Gln Arg Gly Asp Phe Ser
            340                 345                 350

Leu Trp Leu Arg Pro Ala Arg Arg Ala Asp Ala Gly Glu Tyr Arg Ala
        355                 360                 365

Ala Val His Leu Arg Asp Arg Ala Leu Ser Cys Arg Leu Arg Leu Arg
    370                 375                 380

Leu Gly Gln Ala Ser Met Thr Ala Ser Pro Pro Gly Ser Leu Arg Ala
385                 390                 395                 400

Ser Asp Trp Val Ile Leu Asn Cys Ser Phe Ser Arg Pro Asp Arg Pro
                405                 410                 415

Ala Ser Val His Trp Phe Arg Asn Arg Gly Gln Gly Arg Val Pro Val
            420                 425                 430

Arg Glu Ser Pro His His His Leu Ala Glu Ser Phe Leu Phe Leu Pro
        435                 440                 445

Gln Val Ser Pro Met Asp Ser Gly Pro Trp Gly Cys Ile Leu Thr Tyr
    450                 455                 460

Arg Asp Gly Phe Asn Val Ser Ile Met Tyr Asn Leu Thr Val Leu Gly
465                 470                 475                 480

Leu Leu Val Pro Arg Gly Ser Glu Pro Lys Ser Cys Asp Lys Thr His
                485                 490                 495

Thr Ser Pro Pro Ser Pro Ala Pro Glu Leu Leu Gly Gly Ser Ser Val
            500                 505                 510

Phe Leu Phe Pro Pro Lys Pro Lys Asp Thr Leu Met Ile Ser Arg Thr
        515                 520                 525

Pro Glu Val Thr Cys Val Val Val Asp Val Ser His Glu Asp Pro Glu
    530                 535                 540

Val Lys Phe Asn Trp Tyr Val Asp Gly Val Glu Val His Asn Ala Lys
545                 550                 555                 560
```

```
Thr Lys Pro Arg Glu Glu Gln Tyr Gln Ser Thr Tyr Arg Val Val Ser
                565                 570                 575
Val Leu Thr Val Leu His Gln Asp Trp Leu Asn Gly Lys Glu Tyr Lys
            580                 585                 590
Cys Lys Val Ser Asn Lys Ala Leu Pro Ala Pro Ile Glu Lys Thr Ile
        595                 600                 605
Ser Lys Ala Lys Gly Gln Pro Arg Glu Pro Gln Val Tyr Thr Leu Pro
    610                 615                 620
Pro Ser Arg Asp Glu Leu Thr Lys Asn Gln Val Ser Leu Thr Cys Leu
625                 630                 635                 640
Val Lys Gly Phe Tyr Pro Ser Asp Ile Ala Val Glu Trp Glu Ser Asn
                645                 650                 655
Gly Gln Pro Glu Asn Asn Tyr Lys Thr Thr Pro Pro Val Leu Asp Ser
            660                 665                 670
Asp Gly Ser Phe Phe Leu Tyr Ser Lys Leu Thr Val Asp Lys Ser Arg
        675                 680                 685
Trp Gln Gln Gly Asn Val Phe Ser Cys Ser Val Met His Glu Ala Leu
    690                 695                 700
His Asn His Tyr Thr Gln Lys Ser Leu Ser Leu Ser Pro Gly Lys
705                 710                 715

<210> SEQ ID NO 9
<211> LENGTH: 2160
<212> TYPE: DNA
<213> ORGANISM: Artificial Sequence
<220> FEATURE:
<223> OTHER INFORMATION: CTLA-4 BsB human construct variant nucleotide
      sequence 2

<400> SEQUENCE: 9
atgggccaca cacggaggca gggaacatca ccatccaagt gtccatacct caatttcttt      60
cagctcttgg tgctggctgg tctttctcac ttctgttcag gtgttatcca cgtgaccaag     120
gaagtgaaag aagtggcaac gctgtcctgt ggtcacaatg tttctgttga agagctggca     180
caaactcgca tctactggca aaaggagaag aaaatggtgc tgactatgat gtctggggac     240
atgaatatag cccccgagta caagaaccgg accatctttg atatcactaa taacctctcc     300
attgtgatcc tggctctgcg cccatctgac gagggcacat acgagtgtgt tgttctgaag     360
tatgaaaaag acgcttttca gcgggaacac ctggctgaag tgacgttatc agtcaaagct     420
gacttcccta cacctagtat atctgacttt gaaattccaa cttctaatat tagaaggata     480
atttgctcaa cctctggagg ttttccagag cctcacctct cctggttgga aaatggagaa     540
gaattaaatg ccatcaacac aacagttgcc caagatcctg aaactgagct ctatgctgtt     600
gccagcaaac tggatttcaa tatgacaacc aaccacagct tcatgtgtct catcaagtat     660
ggacatttaa gagtgaatca gaccttcaac tggaatacaa ccggcggtgg cggcggaggc     720
ggtggcggtt ccgagctgaa ggtcccggtg gtgtgggccc aggaggggc tcctgcccag     780 ctcccctgca gccccacaat cccctccag gatctcagcc ttctgcgaag agcaggggtc     840
acttggcagc atcagccaga cagtggcccc ccgctgccg ccccggcca tccctggcc     900 cccgccctc accggcggc gccctcctcc tgggggccca ggcccgagcg ctacacggtg     960
ctgagcgtgg gtcccggagg cctgcgcagc gggaggctgc ccctgcagcc ccgcgtccag    1020
ctggatgagc gcggccggca gcgcggggac ttctcgctat ggctgcgccc agcccggcgc    1080
gcggacgccg gcgagtaccg cgccgcggtg cacctcaggg accgcgccct ctcctgccgc    1140
```

```
ctccgtctgc gcctgggcca ggcctcgatg actgccagcc ccccaggatc tctcagagcc    1200
tccgactggg tcattttgaa ctgctccttc agccgccctg accgcccagc tctgtgcat     1260 tggtttcgga accggggcca gggccgagtc cctgtccggg agtcccccca tcaccactta    1320
gcggaaagct tcctcttcct gccccaagtc agccccatgg actctgggcc tggggctgc    1380 atcctcacct acagagatgg cttcaacgtc tccatcatgt ataacctcac tgttctgggt    1440
ctgctggtgc cccggggctc cgagcccaaa tcttgtgaca aaactcacac aagcccaccg    1500
agcccagcac ctgaactcct gggggatcc tcagtcttcc tcttcccccc aaaacccaag     1560
gacaccctca tgatctcccg gacccctgag gtcacatgcg tggtggtgga cgtgagccac    1620
gaagaccctg aggtcaagtt caactggtac gtggacggcg tggaggtgca taatgccaag    1680
acaaagccgc gggaggagca gtaccagagc acgtaccgtg tggtcagcgt cctcaccgtc    1740
ctgcaccagg actggctgaa tggcaaggag tacaagtgca aggtctccaa caaagccctc    1800
ccagccccca tcgagaaaac catctccaaa gccaaagggc agccccgaga accacaggtg    1860
tacaccctgc cccatctcg ggatgagctg accaagaacc aggtcagcct gacctgcctg     1920
gtcaaaggct tctatcccag cgacatcgcc gtggagtggg agagcaatgg cagccggag     1980 aacaactaca agaccacgcc tcccgtgctg gactccgacg gctccttctt cctatacagc    2040
aagctcaccg tggacaagag caggtggcag caggggaacg tcttctcatg ctccgtgatg    2100
catgaggctc tgcacaacca ctacacgcag aagagcctct ccctgtctcc gggtaaatga    2160
```

<210> SEQ ID NO 10
<211> LENGTH: 719
<212> TYPE: PRT
<213> ORGANISM: Artificial Sequence
<220> FEATURE:
<223> OTHER INFORMATION: CTLA-4 BsB human construct variant translated
      protein sequence 2

<400> SEQUENCE: 10

```
Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Ala Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ala Gln Asp
```

-continued

```
              180                 185                 190
Pro Glu Thr Glu Leu Tyr Ala Val Ala Ser Lys Leu Asp Phe Asn Met
             195                 200                 205
Thr Thr Asn His Ser Phe Met Cys Leu Ile Lys Tyr Gly His Leu Arg
             210                 215                 220
Val Asn Gln Thr Phe Asn Trp Asn Thr Thr Gly Gly Gly Gly Gly Gly
225                 230                 235                 240
Gly Gly Gly Ser Gly Ala Glu Val Pro Val Val Trp Ala Gln Glu Gly
                 245                 250                 255
Ala Pro Ala Gln Leu Pro Cys Ser Pro Thr Ile Pro Leu Gln Asp Leu
            260                 265                 270
Ser Leu Leu Arg Arg Ala Gly Val Thr Trp Gln His Gln Pro Asp Ser
            275                 280                 285
Gly Pro Pro Ala Ala Ala Pro Gly His Pro Leu Ala Pro Gly Pro His
            290                 295                 300
Pro Ala Ala Pro Ser Ser Trp Gly Pro Arg Pro Glu Arg Tyr Thr Val
305                 310                 315                 320
Leu Ser Val Gly Pro Gly Gly Leu Arg Ser Gly Arg Leu Pro Leu Gln
                 325                 330                 335
Pro Arg Val Gln Leu Asp Glu Arg Gly Arg Gln Arg Gly Asp Phe Ser
            340                 345                 350
Leu Trp Leu Arg Pro Ala Arg Arg Ala Asp Ala Gly Glu Tyr Arg Ala
            355                 360                 365
Ala Val His Leu Arg Asp Arg Ala Leu Ser Cys Arg Leu Arg Leu Arg
            370                 375                 380
Leu Gly Gln Ala Ser Met Thr Ala Ser Pro Pro Gly Ser Leu Arg Ala
385                 390                 395                 400
Ser Asp Trp Val Ile Leu Asn Cys Ser Phe Ser Arg Pro Asp Arg Pro
                 405                 410                 415
Ala Ser Val His Trp Phe Arg Asn Arg Gly Gln Gly Arg Val Pro Val
            420                 425                 430
Arg Glu Ser Pro His His His Leu Ala Glu Ser Phe Leu Phe Leu Pro
            435                 440                 445
Gln Val Ser Pro Met Asp Ser Gly Pro Trp Gly Cys Ile Leu Thr Tyr
            450                 455                 460
Arg Asp Gly Phe Asn Val Ser Ile Met Tyr Asn Leu Thr Val Leu Gly
465                 470                 475                 480
Leu Leu Val Pro Arg Gly Ser Glu Pro Lys Ser Cys Asp Lys Thr His
                 485                 490                 495
Thr Ser Pro Pro Ser Pro Ala Pro Glu Leu Leu Gly Gly Ser Ser Val
            500                 505                 510
Phe Leu Phe Pro Pro Lys Pro Lys Asp Thr Leu Met Ile Ser Arg Thr
            515                 520                 525
Pro Glu Val Thr Cys Val Val Val Asp Val Ser His Glu Asp Pro Glu
            530                 535                 540
Val Lys Phe Asn Trp Tyr Val Asp Gly Val Glu Val His Asn Ala Lys
545                 550                 555                 560
Thr Lys Pro Arg Glu Glu Gln Tyr Gln Ser Thr Tyr Arg Val Val Ser
                 565                 570                 575
Val Leu Thr Val Leu His Gln Asp Trp Leu Asn Gly Lys Glu Tyr Lys
            580                 585                 590
Cys Lys Val Ser Asn Lys Ala Leu Pro Ala Pro Ile Glu Lys Thr Ile
            595                 600                 605
```

```
Ser Lys Ala Lys Gly Gln Pro Arg Glu Pro Gln Val Tyr Thr Leu Pro
610                 615                 620

Pro Ser Arg Asp Glu Leu Thr Lys Asn Gln Val Ser Leu Thr Cys Leu
625                 630                 635                 640

Val Lys Gly Phe Tyr Pro Ser Asp Ile Ala Val Glu Trp Glu Ser Asn
                645                 650                 655

Gly Gln Pro Glu Asn Asn Tyr Lys Thr Thr Pro Pro Val Leu Asp Ser
                660                 665                 670

Asp Gly Ser Phe Phe Leu Tyr Ser Lys Leu Thr Val Asp Lys Ser Arg
            675                 680                 685

Trp Gln Gln Gly Asn Val Phe Ser Cys Ser Val Met His Glu Ala Leu
                690                 695                 700

His Asn His Tyr Thr Gln Lys Ser Leu Ser Leu Ser Pro Gly Lys
705                 710                 715
```

<210> SEQ ID NO 11
<211> LENGTH: 2160
<212> TYPE: DNA
<213> ORGANISM: Artificial Sequence
<220> FEATURE:
<223> OTHER INFORMATION: CTLA-4 BsB human construct variant nucleotide
      sequence 3

<400> SEQUENCE: 11

```
atgggccaca cacggaggca gggaacatca ccatccaagt gtccatacct caatttcttt      60
cagctcttgg tgctggctgg tctttctcac ttctgttcag gtgttatcca cgtgaccaag     120
gaagtgaaag aagtggcaac gctgtcctgt ggtcacaatg tttctgttga agagctggca     180
caaactcgca tctactggca aaaggagaag aaaatggtgc tgactatgat gtctggggac     240
atgaatatat ggcccgagta caagaaccgg accatctttg atatcactaa taacctctcc     300
attgtgatcc tggctctgcg cccatctgac gagggcacat acgagtgtgt tgttctgaag     360
tatgaaaaag acgctttcaa gcgggaacac ctggctgaag tgacgttatc agtcaaagct     420
gacttcccta cacctagtat atctgacttt gaaattccaa cttctaatat tagaaggata     480
atttgctcaa cctctggagg ttttccagag cctcacctct cctggttgga aaatggagaa     540
gaattaaatg ccatcaacac aacagttgcc caagatcctg aaactgccct ctatgctgtt     600
agcagcaaac tggatttcaa tatgacaacc aaccacagct tcatgtgtct catcaagtat     660
ggacatttaa gagtgaatca gaccttcaac tggaatacaa ccggcggtgg cggcggaggc     720
ggtggcggtt ccggagctga ggtcccggtg gtgtgggccc aggagggggc tcctgcccag     780
ctcccctgca gccccacaat ccccctccag gatctcagcc ttctgcgaag agcaggggtc     840
acttggcagc atcagccaga cagtggcccg cccgctgccg ccccggcca tcccctggcc     900 cccggccctc accggcggc gccctcctcc tgggggccca ggcccgagcg ctacacggtg     960
ctgagcgtgg tcccggagg cctgcgcagc gggaggctgc cctgcagcc ccgcgtccag    1020 ctggatgagc gcggccggca gcgcgggac ttctcgctat ggctgcgccc agcccggcgc    1080
gcggacgccg gcgagtaccg cgccgcggtg cacctcaggg accgcgccct ctcctgccgc    1140
ctccgtctgc gcctgggcca ggcctcgatg actgccagcc cccaggatc tctcagagcc    1200 tccgactggg tcattttgaa ctgctcctcc agccgccctg accgccagc ctctgtgcat    1260 tggtttcgga accggggcca gggccgagtc cctgtccggg agtcccccca tcaccactta    1320
gcggaaagct tcctcttcct gccccaagtc agccccatgg actctgggcc ctggggctgc    1380
```
atcctcacct acagagatgg cttcaacgtc tccatcatgt ataacctcac tgttctgggt 1440
ctgctggtgc cccggggctc cgagcccaaa tcttgtgaca aaactcacac aagcccaccg 1500
agcccagcac ctgaactcct ggggggatcc tcagtcttcc tcttcccccc aaaacccaag 1560
gacaccctca tgatctcccg gacccctgag gtcacatgcg tggtggtgga cgtgagccac 1620
gaagaccctg aggtcaagtt caactggtac gtggacggcg tggaggtgca taatgccaag 1680
acaaagccgc gggaggagca gtaccagagc acgtaccgtg tggtcagcgt cctcaccgtc 1740
ctgcaccagg actggctgaa tggcaaggag tacaagtgca aggtctccaa caaagccctc 1800
ccagccccca tcgagaaaac catctccaaa gccaaagggc agccccgaga accacaggtg 1860
tacaccctgc ccccatctcg ggatgagctg accaagaacc aggtcagcct gacctgcctg 1920
gtcaaaggct tctatcccag cgacatcgcc gtggagtggg agagcaatgg gcagccggag 1980
aacaactaca agaccacgcc tcccgtgctg gactccgacg gctccttctt cctatacagc 2040
aagctcaccg tggacaagag caggtggcag caggggaacg tcttctcatg ctccgtgatg 2100
catgaggctc tgcacaacca ctacacgcag aagagcctct ccctgtctcc gggtaaatga 2160

<210> SEQ ID NO 12
<211> LENGTH: 720
<212> TYPE: PRT
<213> ORGANISM: Artificial Sequence
<220> FEATURE:
<223> OTHER INFORMATION: CTLA-4 BsB human construct variant translated
      protein sequence 3

<400> SEQUENCE: 12

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ala Gln Asp
            180                 185                 190

Pro Glu Thr Ala Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

```
Val Asn Gln Thr Phe Asn Trp Asn Thr Thr Gly Gly Gly Gly Gly
225                 230                 235                 240

Gly Gly Gly Ser Gly Ala Glu Val Pro Val Trp Ala Gln Glu Gly
            245                 250                 255

Ala Pro Ala Gln Leu Pro Cys Ser Pro Thr Ile Pro Leu Gln Asp Leu
        260                 265                 270

Ser Leu Leu Arg Arg Ala Gly Val Thr Trp Gln His Gln Pro Asp Ser
        275                 280                 285

Gly Pro Pro Ala Ala Ala Pro Gly His Pro Leu Ala Pro Gly Pro His
    290                 295                 300

Pro Ala Ala Pro Ser Ser Trp Gly Pro Arg Pro Glu Arg Tyr Thr Val
305                 310                 315                 320

Leu Ser Val Gly Pro Gly Gly Leu Arg Ser Gly Arg Leu Pro Leu Gln
                325                 330                 335

Pro Arg Val Gln Leu Asp Glu Arg Gly Arg Gln Arg Gly Asp Phe Ser
            340                 345                 350

Leu Trp Leu Arg Pro Ala Arg Arg Ala Asp Ala Gly Glu Tyr Arg Ala
        355                 360                 365

Ala Val His Leu Arg Asp Arg Ala Leu Ser Cys Arg Leu Arg Leu Arg
    370                 375                 380

Leu Gly Gln Ala Ser Met Thr Ala Ser Pro Pro Gly Ser Leu Arg Ala
385                 390                 395                 400

Ser Asp Val Val Val Ile Leu Asn Cys Ser Phe Ser Arg Pro Asp Arg
                405                 410                 415

Pro Ala Ser Val His Trp Phe Arg Asn Arg Gly Gln Gly Arg Val Pro
            420                 425                 430

Val Arg Glu Ser Pro His His His Leu Ala Glu Ser Phe Leu Phe Leu
        435                 440                 445

Pro Gln Val Ser Pro Met Asp Ser Gly Pro Trp Gly Cys Ile Leu Thr
    450                 455                 460

Tyr Arg Asp Gly Phe Asn Val Ser Ile Met Tyr Asn Leu Thr Val Leu
465                 470                 475                 480

Gly Leu Leu Val Pro Arg Gly Ser Glu Pro Lys Ser Cys Asp Lys Thr
                485                 490                 495

His Thr Ser Pro Pro Ser Pro Ala Pro Glu Leu Leu Gly Gly Ser Ser
            500                 505                 510

Val Phe Leu Phe Pro Pro Lys Pro Lys Asp Thr Leu Met Ile Ser Arg
        515                 520                 525

Thr Pro Glu Val Thr Cys Val Val Val Asp Val Ser His Glu Asp Pro
    530                 535                 540

Glu Val Lys Phe Asn Trp Tyr Val Asp Gly Val Glu Val His Asn Ala
545                 550                 555                 560

Lys Thr Lys Pro Arg Glu Glu Gln Tyr Gln Ser Thr Tyr Arg Val Val
                565                 570                 575

Ser Val Leu Thr Val Leu His Gln Asp Trp Leu Asn Gly Lys Glu Tyr
            580                 585                 590

Lys Cys Lys Val Ser Asn Lys Ala Leu Pro Ala Pro Ile Glu Lys Thr
        595                 600                 605

Ile Ser Lys Ala Lys Gly Gln Pro Arg Glu Pro Gln Val Tyr Thr Leu
    610                 615                 620

Pro Pro Ser Arg Asp Glu Leu Thr Lys Asn Gln Val Ser Leu Thr Cys
625                 630                 635                 640

Leu Val Lys Gly Phe Tyr Pro Ser Asp Ile Ala Val Glu Trp Glu Ser
```

```
                  645                 650                 655
Asn Gly Gln Pro Glu Asn Asn Tyr Lys Thr Thr Pro Pro Val Leu Asp
            660                 665                 670

Ser Asp Gly Ser Phe Phe Leu Tyr Ser Lys Leu Thr Val Asp Lys Ser
        675                 680                 685

Arg Trp Gln Gln Gly Asn Val Phe Ser Cys Ser Val Met His Glu Ala
    690                 695                 700

Leu His Asn His Tyr Thr Gln Lys Ser Leu Ser Leu Ser Pro Gly Lys
705                 710                 715                 720

<210> SEQ ID NO 13
<211> LENGTH: 2160
<212> TYPE: DNA
<213> ORGANISM: Artificial Sequence
<220> FEATURE:
<223> OTHER INFORMATION: CTLA-4 BsB human construct variant nucleotide
      sequence 4

<400> SEQUENCE: 13
atgggccaca cacggaggca gggaacatca ccatccaagt gtccatacct caatttcttt      60
cagctcttgg tgctggctgg tctttctcac ttctgttcag tgttatcca cgtgaccaag      120 gaagtgaaag aagtggcaac gctgtcctgt ggtcacaatg tttctgttga agagctggca    180
caaactcgca tctactggca aaaggagaag aaaatggtgc tgactatgat gtctggggac    240
atgaatatat ggcccgagta caagaaccgg accatctttg atatcactaa taacctctcc    300
attgtgatcc tggctctgcg cccatctgac gagggcacat acgagtgtgt tgttctgaag    360
tatgaaaaag acgctttcaa gcgggaacac ctggctgaag tgacgttatc agtcaaagct    420
gacttcccta cacctagtat atctgacttt gaaattccaa cttctaatat tagaaggata    480
atttgctcaa cctctggagg ttttccagag cctcacctct cctggttgga aaatggagaa    540
gaattaaatg ccatcaacac aacagttgcc caagatcctg aaactgccct ctatgctgtt    600
gccagcaaac tggatttcaa tatgacaacc aaccacagct tcatgtgtct catcaagtat    660
ggacatttaa gagtgaatca gaccttcaac tggaatacaa ccggcggtgg cggcggaggc    720
ggtggcggtt ccggagctga ggtcccggtg gtgtgggccc aggaggggc tcctgcccag    780 ctcccctgca gccccacaat cccctccag gatctcagcc ttctgcgaag agcaggggtc    840
acttggcagc atcagccaga cagtggcccg ccgctgccg ccccggcca tccctggcc    900 cccggccctc acccggcggc gccctcctcc tggggcccca ggcccgagcg ctacacggtg    960
ctgagcgtgg tcccggagg cctgcgcagc gggaggctgc cctgcagcc ccgcgtccag    1020 ctggatgagc gcggccggca gcgcgggac ttctcgctat ggctgcgccc agcccggcgc    1080
gcggacgccg gcgagtaccg cgccgcgtg cacctcaggg accgcgccct ctcctgccgc    1140
ctccgtctgc gcctgggcca ggcctcgatg actgccagcc cccaggatc tctcagagcc    1200 tccgactggg tcattttgaa ctgctccttc agcgccctg accgccagc ctctgtgcat    1260 tggtttcgga accggggcca gggccgagtc cctgtccggg agtcccccca tcaccactta    1320
gcggaaagct tcctcttcct gcccaagtc agcccatgg actctgggcc tggggctgc    1380 atcctcacct acagagatgg cttcaacgtc tccatcatgt ataacctcac tgttctgggt    1440
ctgctggtgc ccggggctc cgagcccaaa tcttgtgaca aaactcacac aagcccaccg    1500
agcccagcac ctgaactcct gggggatcc tcagtcttcc tcttcccccc aaaacccaag    1560
gacaccctca tgatctcccg gacccctgag gtcacatgcg tggtggtgga cgtgagccac    1620
```

```
gaagaccctg aggtcaagtt caactggtac gtggacggcg tggaggtgca taatgccaag    1680
acaaagccgc gggaggagca gtaccagagc acgtaccgtg tggtcagcgt cctcaccgtc    1740
ctgcaccagg actggctgaa tggcaaggag tacaagtgca aggtctccaa caaagccctc    1800
ccagccccca tcgagaaaac catctccaaa gccaagggc agccccgaga ccacaggtg     1860 tacaccctgc ccccatctcg ggatgagctg accaagaacc aggtcagcct gacctgcctg    1920
gtcaaaggct tctatcccag cgacatcgcc gtggagtggg agagcaatgg gcagccggag    1980
aacaactaca agaccacgcc tcccgtgctg gactccgacg gctccttctt cctatacagc    2040
aagctcaccg tggacaagag caggtggcag caggggaacg tcttctcatg ctccgtgatg    2100
catgaggctc tgcacaacca ctacacgcag aagagcctct ccctgtctcc gggtaaatga    2160
```

<210> SEQ ID NO 14
<211> LENGTH: 719
<212> TYPE: PRT
<213> ORGANISM: Artificial Sequence
<220> FEATURE:
<223> OTHER INFORMATION: CTLA-4 BsB human construct variant translated
    protein sequence 4

<400> SEQUENCE: 14

```
Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ala Gln Asp
            180                 185                 190

Pro Glu Thr Ala Leu Tyr Ala Val Ala Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Gly Gly Gly Gly Gly Gly
225                 230                 235                 240

Gly Gly Gly Ser Gly Ala Glu Val Pro Val Val Trp Ala Gln Glu Gly
                245                 250                 255

Ala Pro Ala Gln Leu Pro Cys Ser Pro Thr Ile Pro Leu Gln Asp Leu
            260                 265                 270
```

```
Ser Leu Leu Arg Arg Ala Gly Val Thr Trp Gln His Gln Pro Asp Ser
        275                 280                 285

Gly Pro Pro Ala Ala Ala Pro Gly His Pro Leu Ala Pro Gly Pro His
    290                 295                 300

Pro Ala Ala Pro Ser Ser Trp Gly Pro Arg Pro Glu Arg Tyr Thr Val
305                 310                 315                 320

Leu Ser Val Gly Pro Gly Gly Leu Arg Ser Gly Arg Leu Pro Leu Gln
                325                 330                 335

Pro Arg Val Gln Leu Asp Glu Arg Gly Arg Gln Arg Gly Asp Phe Ser
                340                 345                 350

Leu Trp Leu Arg Pro Ala Arg Arg Ala Asp Ala Gly Glu Tyr Arg Ala
        355                 360                 365

Ala Val His Leu Arg Asp Arg Ala Leu Ser Cys Arg Leu Arg Leu Arg
    370                 375                 380

Leu Gly Gln Ala Ser Met Thr Ala Ser Pro Pro Gly Ser Leu Arg Ala
385                 390                 395                 400

Ser Asp Trp Val Ile Leu Asn Cys Ser Phe Ser Arg Pro Asp Arg Pro
                405                 410                 415

Ala Ser Val His Trp Phe Arg Asn Arg Gly Gln Gly Arg Val Pro Val
                420                 425                 430

Arg Glu Ser Pro His His His Leu Ala Glu Ser Phe Leu Phe Leu Pro
        435                 440                 445

Gln Val Ser Pro Met Asp Ser Gly Pro Trp Gly Cys Ile Leu Thr Tyr
    450                 455                 460

Arg Asp Gly Phe Asn Val Ser Ile Met Tyr Asn Leu Thr Val Leu Gly
465                 470                 475                 480

Leu Leu Val Pro Arg Gly Ser Glu Pro Lys Ser Cys Asp Lys Thr His
                485                 490                 495

Thr Ser Pro Pro Ser Pro Ala Pro Glu Leu Leu Gly Gly Ser Ser Val
                500                 505                 510

Phe Leu Phe Pro Pro Lys Pro Lys Asp Thr Leu Met Ile Ser Arg Thr
        515                 520                 525

Pro Glu Val Thr Cys Val Val Asp Val Ser His Glu Asp Pro Glu
    530                 535                 540

Val Lys Phe Asn Trp Tyr Val Asp Gly Val Glu Val His Asn Ala Lys
545                 550                 555                 560

Thr Lys Pro Arg Glu Glu Gln Tyr Gln Ser Thr Tyr Arg Val Val Ser
                565                 570                 575

Val Leu Thr Val Leu His Gln Asp Trp Leu Asn Gly Lys Glu Tyr Lys
                580                 585                 590

Cys Lys Val Ser Asn Lys Ala Leu Pro Ala Pro Ile Glu Lys Thr Ile
        595                 600                 605

Ser Lys Ala Lys Gly Gln Pro Arg Glu Pro Gln Val Tyr Thr Leu Pro
    610                 615                 620

Pro Ser Arg Asp Glu Leu Thr Lys Asn Gln Val Ser Leu Thr Cys Leu
625                 630                 635                 640

Val Lys Gly Phe Tyr Pro Ser Asp Ile Ala Val Glu Trp Glu Ser Asn
                645                 650                 655

Gly Gln Pro Glu Asn Asn Tyr Lys Thr Thr Pro Pro Val Leu Asp Ser
                660                 665                 670

Asp Gly Ser Phe Phe Leu Tyr Ser Lys Leu Thr Val Asp Lys Ser Arg
        675                 680                 685
```

```
Trp Gln Gln Gly Asn Val Phe Ser Cys Ser Val Met His Glu Ala Leu
            690                 695                 700

His Asn His Tyr Thr Gln Lys Ser Leu Ser Leu Ser Pro Gly Lys
705                 710                 715
```

<210> SEQ ID NO 15
<211> LENGTH: 288
<212> TYPE: PRT
<213> ORGANISM: Homo sapiens

<400> SEQUENCE: 15

```
Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45

Ser Cys Gly His Asn Val Ser Val Glu Leu Ala Gln Thr Arg Ile
    50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
    130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
    210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
            260                 265                 270

Glu Arg Arg Arg Asn Glu Arg Leu Arg Arg Glu Ser Val Arg Pro Val
        275                 280                 285
```

<210> SEQ ID NO 16
<211> LENGTH: 1485
<212> TYPE: DNA
<213> ORGANISM: Artificial Sequence
<220> FEATURE:
<223> OTHER INFORMATION: BsBdelta (CD80wa-Fc) DNA

<400> SEQUENCE: 16

```
atggcttgca attgtcagtt gatgcaggat acaccactcc tcaagtttcc atgtccaagg    60
```

```
ctcattcttc tctttgtgct gctgattcgt ctttcacaag tgtcttcaga tgttgatgaa    120
caactgtcca agtcagtgaa agataaggta ttgctgcctt gccgttacaa ctctcctcat    180
gaagatgagt ctgaagaccg aatctactgg caaaaacatg acaaagtggt gctgtctgtc    240
attgctggga aactaaaagt ggcgcccgag tataagaacc ggactttata tgacaacact    300
acctactctc ttatcatcct gggcctggtc ctttcagacc ggggcacata cagctgtgtc    360
gttcaaaaga aggaaagagg aacgtatgaa gttaaacact tggctttagt aaagttgtcc    420
atcaaagctg acttctctac ccccaacata actgagtctg gaaacccatc tgcagacact    480
aaaaggatta cctgctttgc ttccgggggt ttcccaaagc ctcgcttctc ttggttggaa    540
aatggaagag aattacctgg catcaatacg acaatttccc aggatcctga atctgaattg    600
tacaccatta gtagccaact agatttcaat acgactcgca accacaccat taagtgtctc    660
attaaatatg gagatgctca cgtgtcagag gacttcacct gggagcccag agggcccaca    720
atcaagccct gtcctccatg caaatgccca gcacctaacc tcttgggtgg accatccgtc    780
ttcatcttcc ctccaaagat caaggatgta ctcatgatct ccctgagccc catggtcaca    840
tgtgtggtgg tggatgtgag cgaggatgac ccagatgtcc agatcagctg gttcgtgaac    900
aacgtggaag tactcacagc tcagacacaa acccatagag aggattacaa cagtactctc    960
cgggtggtca gtgccctccc catccagcac caggactgga tgagtggcaa ggagttcaaa   1020
tgcaaggtca acaacaaagc cctcccagcg cccatcgaga gaaccatctc aaaacccaaa   1080
gggtcagtaa gagctccaca ggtatatgtc ttgcctccac cagaagaaga gatgactaag   1140
aaacaggtca ctctgacctg catggtcaca gacttcatgc ctgaagacat ttacgtggag   1200
tggaccaaca acgggaaaac agagctaaac tacaagaaca ctgaaccagt cctggactct   1260
gatggttctt acttcatgta cagcaagctg agagtggaaa agaagaactg ggtggaaaga   1320
aatagctact cctgctcagt ggtccacgag ggtctgcaca atcaccacac gactaagagc   1380
ttctcccgga ctccgggtaa aggcggtggc ggcggaggcg gtggcggtgg gcctgggaaa   1440
gagctgggtc tggagcccgt agcccaccat caccatcatc actga                   1485
```

```

<210> SEQ ID NO 17
<211> LENGTH: 494
<212> TYPE: PRT
<213> ORGANISM: Artificial Sequence
<220> FEATURE:
<223> OTHER INFORMATION: BsBdelta (CD80wa-Fc) Protein

<400> SEQUENCE: 17

Met Ala Cys Asn Cys Gln Leu Met Gln Asp Thr Pro Leu Leu Lys Phe
1               5                   10                  15

Pro Cys Pro Arg Leu Ile Leu Leu Phe Val Leu Leu Ile Arg Leu Ser
            20                  25                  30

Gln Val Ser Ser Asp Val Asp Glu Gln Leu Ser Lys Ser Val Lys Asp
        35                  40                  45

Lys Val Leu Leu Pro Cys Arg Tyr Asn Ser Pro His Glu Asp Glu Ser
    50                  55                  60

Glu Asp Arg Ile Tyr Trp Gln Lys His Asp Lys Val Val Leu Ser Val
65                  70                  75                  80

Ile Ala Gly Lys Leu Lys Val Ala Pro Glu Tyr Lys Asn Arg Thr Leu
                85                  90                  95

Tyr Asp Asn Thr Thr Tyr Ser Leu Ile Ile Leu Gly Leu Val Leu Ser
            100                 105                 110
```

```
Asp Arg Gly Thr Tyr Ser Cys Val Val Gln Lys Lys Glu Arg Gly Thr
            115                 120                 125

Tyr Glu Val Lys His Leu Ala Leu Val Lys Leu Ser Ile Lys Ala Asp
        130                 135                 140

Phe Ser Thr Pro Asn Ile Thr Glu Ser Gly Asn Pro Ser Ala Asp Thr
145                 150                 155                 160

Lys Arg Ile Thr Cys Phe Ala Ser Gly Gly Phe Pro Lys Pro Arg Phe
                165                 170                 175

Ser Trp Leu Glu Asn Gly Arg Glu Leu Pro Gly Ile Asn Thr Thr Ile
                180                 185                 190

Ser Gln Asp Pro Glu Ser Glu Leu Tyr Thr Ile Ser Ser Gln Leu Asp
            195                 200                 205

Phe Asn Thr Thr Arg Asn His Thr Ile Lys Cys Leu Ile Lys Tyr Gly
210                 215                 220

Asp Ala His Val Ser Glu Asp Phe Thr Trp Glu Pro Arg Gly Pro Thr
225                 230                 235                 240

Ile Lys Pro Cys Pro Pro Cys Lys Cys Pro Ala Pro Asn Leu Leu Gly
                245                 250                 255

Gly Pro Ser Val Phe Ile Phe Pro Pro Lys Ile Lys Asp Val Leu Met
                260                 265                 270

Ile Ser Leu Ser Pro Met Val Thr Cys Val Val Val Asp Val Ser Glu
                275                 280                 285

Asp Asp Pro Asp Val Gln Ile Ser Trp Phe Val Asn Asn Val Glu Val
        290                 295                 300

Leu Thr Ala Gln Thr Gln Thr His Arg Glu Asp Tyr Asn Ser Thr Leu
305                 310                 315                 320

Arg Val Val Ser Ala Leu Pro Ile Gln His Gln Asp Trp Met Ser Gly
                325                 330                 335

Lys Glu Phe Lys Cys Lys Val Asn Asn Lys Ala Leu Pro Ala Pro Ile
                340                 345                 350

Glu Arg Thr Ile Ser Lys Pro Lys Gly Ser Val Arg Ala Pro Gln Val
            355                 360                 365

Tyr Val Leu Pro Pro Pro Glu Glu Glu Met Thr Lys Lys Gln Val Thr
        370                 375                 380

Leu Thr Cys Met Val Thr Asp Phe Met Pro Glu Asp Ile Tyr Val Glu
385                 390                 395                 400

Trp Thr Asn Asn Gly Lys Thr Glu Leu Asn Tyr Lys Asn Thr Glu Pro
                405                 410                 415

Val Leu Asp Ser Asp Gly Ser Tyr Phe Met Tyr Ser Lys Leu Arg Val
                420                 425                 430

Glu Lys Lys Asn Trp Val Glu Arg Asn Ser Tyr Ser Cys Ser Val Val
            435                 440                 445

His Glu Gly Leu His Asn His His Thr Thr Lys Ser Phe Ser Arg Thr
        450                 455                 460

Pro Gly Lys Gly Gly Gly Gly Gly Gly Gly Gly Gly Pro Gly Lys
465                 470                 475                 480

Glu Leu Gly Leu Glu Pro Val Ala His His His His His
                485                 490
```

INHIBITORS OF T-CELL ACTIVATION

CROSS-REFERENCE TO RELATED APPLICATIONS

This application is a divisional of U.S. patent application Ser. No. 14/128.461, filed Aug. 13, 2014, which is a 35 U.S.C. § 371 National Stage filing of International Patent Annlication No. PCT/US2012/045017, filed Jun. 29, 2012, which claims the benefit of U.S. Provisional Patent Application Ser. No. 61/503,282, filed Jun. 30, 2011, the entire contents of which are hereby incorporated herein by reference.

BACKGROUND OF THE INVENTION

Cell therapy using freshly isolated, ex vivo expanded or in vitro induced Tregs in models of autoimmune diseases or organ transplants have demonstrated that adoptive transfer of Tregs can restore the balance of Tregs versus effector T cells, thereby controlling autoimmunity associated with these diseases (Allan et al., (2008) *Immunol. Rev.* 223:391-421; Jiang et al., (2006) *Expert review of clinical immunology* 2:387-392; Riley et al., (2009) *Immunity* 30:656-665; Tang et al., (2012) *Journal of molecular cell biology* 4:11-21). However, the use of adoptive transfer as a therapeutic strategy presents several challenges to translation into the clinic. The number of autologous Tregs that can be isolated from peripheral blood of a human subject is limiting and extensive ex vivo expansion of the Tregs may alter their functionality and/or purity. As the isolated Tregs are polyclonal, they can exert a pan-immune suppressive function on non-target effector T cells. Importantly, the plasticity of Tregs poses a significant challenge (Bluestone et al., (2009) *Nat Rev Immunol* 9:811-816; Zhou et al., (2009a) *Curr Opin Immunol* 21:281-285), as adoptively transferred Tregs can lose Foxp3 expression and redifferentiate into Th17 cells (Koenen et al., (2008) *Blood* 112:2340-2352.) or pathogenic memory T cells (Zhou et al., (2009b) *Nat Immunol* 10:1000-1007) which raises the risk of aggravating the autoimmunity or inflammation.

A therapeutic that induces the generation of Tregs in an antigen-specific manner in situ would have advantages over adoptive Treg cell therapy. Cytotoxic T lymphocyte associated antigen-4 (CTLA-4; CD 152) is a well-established negative regulator of the T cell response, is important for the maintenance of T cell homeostasis and self-tolerance. CTLA-4 is homologous to the co-stimulatory molecule CD28 and shares the same ligands, CD80 (B7.1) and CD86 (B7.2), which are expressed on the surface of antigen presenting cells (APCs). However, differential binding of CD80/CD86 on APCs to CD28 and CTLA-4 on effector T cells leads to opposing outcomes, with CD28 triggering T cell activation and CTLA-4 causing T cell inhibition.

Because CD28 is constitutively expressed on T cells and the expression of CTLA-4 is only induced following T cell activation, peaking 2-3 days later (Jago et al., (2004) *Clinical & Experimental Immunology*, 136: 463-471), extensive T cell activation would have occurred prior to CTLA-4 engagement. Hence, the main role of CTLA-4 is to act as a safeguard against an excessive T cell response rather than to inhibit T cell activation. However, early engagement of CTLA-4 by its ligand and its subsequent crosslinking to the T cell receptor (TCR) can prematurely dampen TCR signaling, causing T cell inhibition and hyporesponsiveness, or anergy. This concept has been validated experimentally using a variety of methods, including the following: (i) crosslinking T cell-activating antibodies (anti-CD3/antiCD28) using an agonistic anti-CTLA-4 antibody by co-immobilization on a bead or via a secondary antibody (Blair et al., (1998) *J. Immunol.* 160: 12-15; Krummel and Allison, (1996) *J Exp Med* 183:2533-2540; Walunas et al., (1996) *J. Exp. Med.* 183:2541-2550); (ii) molecularly engineering a surface-linked agonistic scFv against CTLA-4 on an APC (Fife et al., (2006) *J. Clin. Invest.* 116 (8):2252-61; Griffin et al., (2001) *J. Immunol. Methods.* 248 (1-2):77-90; Griffin et al., (2000) *J. Immunol.* 164 (9):4433-42); and (iii) chemically crosslinking antibodies that recognize specific antigens on an APC to an agonistic anti-CTLA-4 antibody (Li et al., (2007). *J. Immunol.* 179 (8):5191-203; Rao et al., (2001) *Clin. Immunol.* 101 (2):136-45; Vasu et al., (2004) *J. Immunol.* 173 (4):2866-76).

Restoring the balance of Tregs versus effector T cells is a promising means of treating autoimmune disease. However, cell therapy involving transfer of Tregs has certain limitations. Accordingly, therapeutics that can induce the generation of Tregs (e.g., CTLA-4) in an antigen-specific manner for the treatment of autoimmune disease are urgently required.

SUMMARY OF THE INVENTION

The present invention relates to ligands which crosslink ligand-engaged cytotoxic T lymphocyte antigen-4 (CTLA-4) to the T cell receptor (TCR) during the early phase of T cell activation and thereby attenuate TCR signaling, leading to T cell inhibition. To develop an agent that can inhibit T cell activation, a bispecific fusion protein comprising moieties that selectively bind and activate CTLA-4 and co-ligate it to the TCR was generated. In contrast to the approaches of the prior art, the bispecific fusion protein was engineered to crosslink MHC to CTLA-4; both are then drawn to the TCR, generating the CTLA-4/MHCII/TCR tri-molecular complex within the immune synapses.

Crosslinking ligand-engaged cytotoxic T lymphocyte antigen-4 (CTLA-4) to the TCR with a bispecific fusion protein (BsB) comprising a mutant mouse CD80 and lymphocyte activation antigen-3 in an allogenic MLR attenuated TCR signaling and direct T cell differentiation towards Foxp3$^+$ regulatory T cells (Tregs). As described herein, antigen-specific Tregs can also be induced in an antigen-specific setting. Treatment of non-obese diabetic (NOD) mice with a short course of BsB moderately delayed the onset of autoimmune type 1 diabetes (T1D) with a transient increase of Tregs in blood. However, a longer course of treatment of NOD animals with BsB significantly delayed the onset of disease as well as reduced the incidence of animals presenting with diabetes. Histopathological analysis of the pancreata of BsB-treated mice that remained non-diabetic revealed the presence of Tregs that were intermixed with other CD3$^+$ T cells and non-T cell leukocytes around the islets. This peri-insulitis was associated with minimal invasive insulitis and no notable destruction of the insulin-producing β-cells. Thus, bifunctional proteins capable of engaging CTLA-4 and MHCII and indirectly co-ligating it to the TCR may induce antigen-specific Tregs in vivo to protect mice from T1D or other autoimmune diseases.

In particular, the invention describes bispecific fusion proteins which cross-link CTLA-4 to the pMHCII complex. For example, there is described a bispecific fusion protein comprising a mutant mouse CD80 (CD80w88a) and lymphocyte activation antigen-3 (LAG-3) which is engineered to concurrently engage CTLA-4 and crosslink it to the TCR via pMHCII. In a first aspect, therefore, there is provided a bispecific biologic comprising a ligand specific for CTLA-4 and a ligand specific for a pMHC complex.

In one aspect, the invention provides a bispecific biologic comprising a ligand specific for CTLA-4 and a ligand specific for a pMHC complex. The bispecific biologic according to the invention is capable of cross-linking CTLA-4, present on T-cells, with the peptide MHC (pMHC) complex on antigen-presenting cells (APC). The peptide MHC complex is bound by the cognate T-cell receptor (TCR) on T-cells, meaning that the bispecific biologic according to the invention gives rise to a tripartite CTLA-4/MHC/TCR complex.

In various embodiments of the aspects delineated herein, the ligand specific for CTLA-4 is selected from an antibody specific for CTLA-4, and CD80 (B7-1) or CD86 (B7-2). In a particular embodiment, the antibody specific for CTLA-4, and CD80 (B7-1) or CD86 (B7-2) is an agonistic antibody. Antibodies specific for CTLA-4 can be engineered, and both CD80 and CD86 are natural ligands for CTLA-4. In one aspect, CD80 or a mutant thereof is used, since CD80 binds preferentially to CTLA-4 over CD28, and thus promotes T-cell inactivation as opposed to activation.

In various embodiments of the aspects delineated herein, the ligand specific for the pMHC complex can be selected from an anti-MHC antibody and LAG-3. The LAG-3 polypeptide is a natural ligand for the MHCII protein. In one embodiment, the MHC is MHC-II (which interacts with $CD4^+$ T-cells). In another embodiment the MHC is MHC-I, which interacts with $CD8^+$ T-cells.

In the bispecific biologic according to the invention, the ligand specific for CTLA-4 and the ligand specific for the pMHC complex are preferably spaced apart by a linker. The linker can take the form of one or more of a polyamino acid sequence and an antibody Fc domain. A suitable polyamino acid sequence is G9 (Gly-9).

In various embodiments of the aspects delineated herein, the ligand specific for CTLA-4 is CD80, or a mutant thereof which is mutated to increase specificity for CTLA-4 over CD28. In one embodiment, the mutated CD80 comprises one or more mutations selected from W88A, K75G. K75V, Si 12G, R126S, R126D, G127L, S193A, and S204A, using sequence numbering in mouse CD80 precursor, or their human CD80 counterparts (W84A, K71G, K71V, S109G, R123S, R123D, G124L, S190A, and S201A) and in addition R63A, M81A, N97A, E196A.

In one embodiment, the bispecific biologic comprises CD80, which comprises the mutation W84A (human) or W88A (mouse).

In a particular embodiment, the ligand specific for the MHCII complex is LAG-3. Advantageously, LAG-3 is mutated to increase specificity for pMHCII. For example, LAG-3 comprises one or more mutations selected from R73E, R75A, R75E and R76E (Huard et al., (1997) *Proc. Natl. Acad. Sci. USA*. 94 (11): 5744-5749. In one embodiment, LAG-3 comprises the mutation R75E.

Preferential binding of the bispecific fusion protein to CTLA-4 over CD28 was attained using mutant CD80 (CD80w88a), which contains alanine instead of tryptophan at amino acid 88 (numbered in mouse CD80), as the ligand. CD80w88a binds CTLA-4 but exhibits minimal affinity for CD28 (Wu et al., (1997), *J. Exp. Med.* 185:1327-1335).

Lymphocyte activation gene-3 (LAG-3), a natural ligand of MHCII, was selected as the other binding component of the bispecific fusion protein (Baixeras et al., (1992) *J. Exp. Med.* 176:327-337; Triebel et al., (1990) *J. Exp. Med.* 171:1393-1405). We show that a fusion protein with such bi-functionality effectively inhibits T cell activation and stimulates anti-inflammatory cytokines IL-10 and TGF-β production. More importantly, this bispecific fusion protein also directed T cell differentiation into highly suppressive Foxp3$^+$ Tregs. This did not occur when the well-established co-stimulatory inhibitor CTLA-4Ig was used instead (Bluestone et al., (2006) *Immunity* 24:233-238; Linsley and Nadler (2009) *Immunol. Rev.* 229:307-321). Therefore, early engagement of CTLA-4 and crosslinking of CTLA-4 to the TCR during T cell activation could actively influence T cell differentiation. Such bispecific fusion proteins might thus represent a novel class of biologics that could be used to control excessive T cell responses in autoimmune diseases.

In a second aspect of the invention, there is provided the use of a bispecific biologic comprising a ligand specific for CTLA-4 and a ligand specific for a pMHC complex according to the first aspect of the invention, for the tolerisation of a T-cell by contacting said T-cell with an antigen-presenting cell which is presenting a peptide derived from said antigen complexed to a MHC molecule and said bispecific biologic.

In a third aspect, there is provided the use of a bispecific biologic comprising a ligand specific for CTLA-4 and a ligand specific for a pMHC complex according to the first aspect of the invention, in the treatment of a disease selected from an autoimmune disease and transplant rejection.

For example, the autoimmune disease is type 1 diabetes (T1D, Systemic Lupus Erythematosus (SLE), Rheumatoid Arthritis (RA) and inflammatory bowel disease (IBD) (including ulcerative colitis (UC) and Crohn's disease (CD)), multiple sclerosis (MS), scleroderma, and other diseases and disorders, such as PV (pemphigus vulgaris), psoriasis, atopic dermatitis, celiac disease, Chronic Obstructive Lung disease, Hashimoto's thyroiditis, Graves' disease (thyroid), Sjogren's syndrome, Guillain-Barre syndrome, Goodpasture's syndrome, Addison's disease, Wegener's granulomatosis, primary biliary sclerosis, sclerosing cholangitis, autoimmune hepatitis, polymyalgia rheumatica. Raynaud's phenomenon, temporal arteritis, giant cell arteritis, autoimmune hemolytic anemia, pernicious anemia, polyarteritis nodosa. Behcet's disease, primary bilary cirrhosis, uveitis, myocarditis, rheumatic fever, ankylosing spondylitis, glomerulenephritis, sarcoidosis, dermatomyositis, myasthenia gravis, polymyositis, alopecia areata, and vitilgo.

In a fourth aspect, there is provided a method of tolerising a T-cell to an antigen, comprising contacting said T-cell with an antigen-presenting cell which is presenting a peptide derived from said antigen complexed to a MHC molecule and a bispecific biologic according to the first aspect of the invention.

In a fifth aspect, there is provided a method for treating a subject suffering from a condition selected from an autoimmune disease and transplant rejection, comprising the steps of administering to a subject in need thereof a bispecific biologic comprising a ligand specific for CTLA-4 and a ligand specific for a pMHC complex according to the first aspect of the invention.

For example, the autoimmune disease is Type 1 diabetes (T1D).

DESCRIPTION OF THE FIGURES

FIG. 1. Designs of BsB and BsBΔ. (A) Schematic drawings of the BsB (bispecific biologics) and BsBΔ fusion proteins. (B) Schematic drawing of pMHCII, the TCR and co-stimulatory molecules in the immune synapse, as well as the proposed scheme for BsB-mediated crosslinking of CTLA-4 to the TCR via the CTLA-4/MHC 11/TCR trimolecular complex. The fusion protein engages CTLA-4 and indirectly ligates the TCR via binding to MHCII in the immune synapse. The two solid sides of the triangle denote crosslinking of MHCI I and CTLA-4 as well as MHCI I and TCR; the dashed side depicts ligation of CTLA-4 to TCR. The dotted line indicates inhibition of TCR signaling by BsB-engaged CTLA-4. C. Schematic drawing showing that the action of BsBΔ is similar to that of BsB except, it is unable to ligate the TCR.

Figure 2:
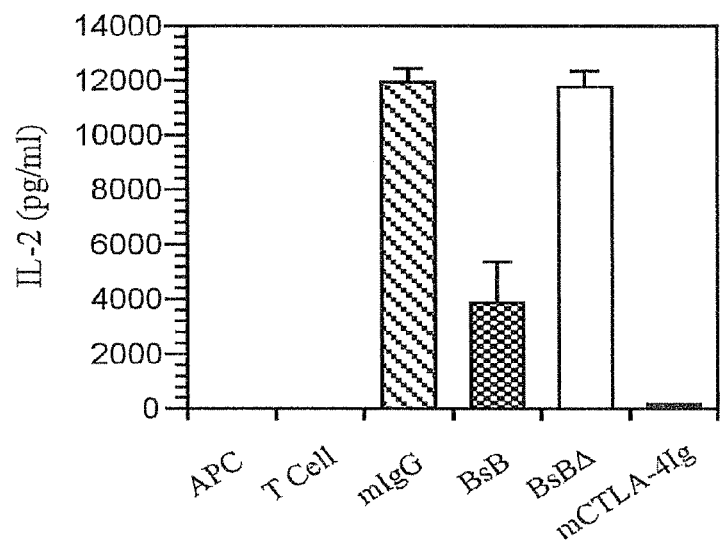

FIG. 2. Inhibition of allogenic T cell activation by BsB in a mixed lymphocyte reaction. Naïve T cells from C57BL/6 mice and LPS-treated and irradiated BALB/c APCs were mixed with the test constructs for 2 days. Culture media were then harvested and assayed for IL-2. Only BsB and CTLA-4Ig inhibited T cell activation, as indicated by a decreased amount of IL-2 in the media. The figure is representative of more than five independent but similar studies.

Figure 3:
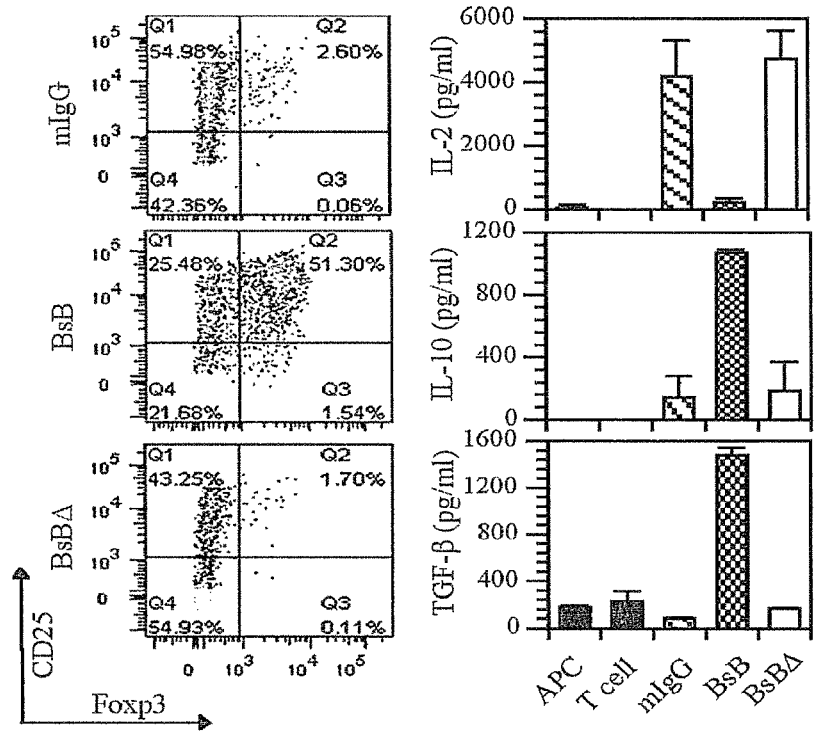
Figure 3:
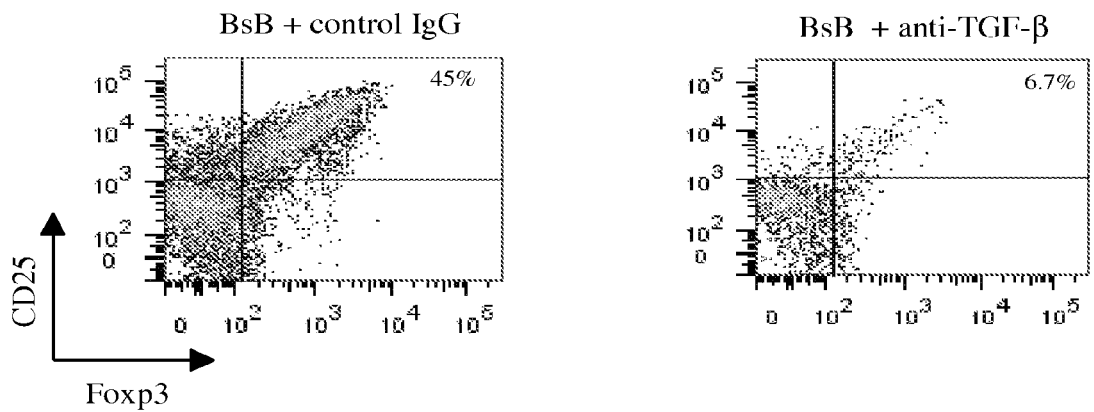

FIG. 3. Induction of Foxp3$^+$ Tregs and IL-10 and TGF-β production by BsB. (A) Allogenic mixed lymphocyte reactions were set up as described in the legend to FIG. 2, using naïve $CD4^+CD62L^{hi}CD25^-GFP^{lo}$ cells that had been isolated from Foxp3-EGFP knock-in mice in the presence of the test constructs. Five days post-activation, $CD4^+$ T cells were analyzed for GFP expression by flow cytometry. Tregs were gated as GFP$^+$ and CD25$^+$ cells. Only BsB treatment led to GFP expression, indicating induction of Foxp3$^+$ Tregs (middle left panel). Culture media were collected for cytokine analysis (right panels), which revealed elevated IL-10 and TGF-β levels in the presence of BsB. The data are representative of numerous independent but similar studies. (B) Requirement of autocrine TGF-β for Treg induction is indicated by the complete blockade of Treg induction in the presence of a blocking antibody to TGF-β, whereas control Ab did not noticeably impact Treg induction.

Figure 4:
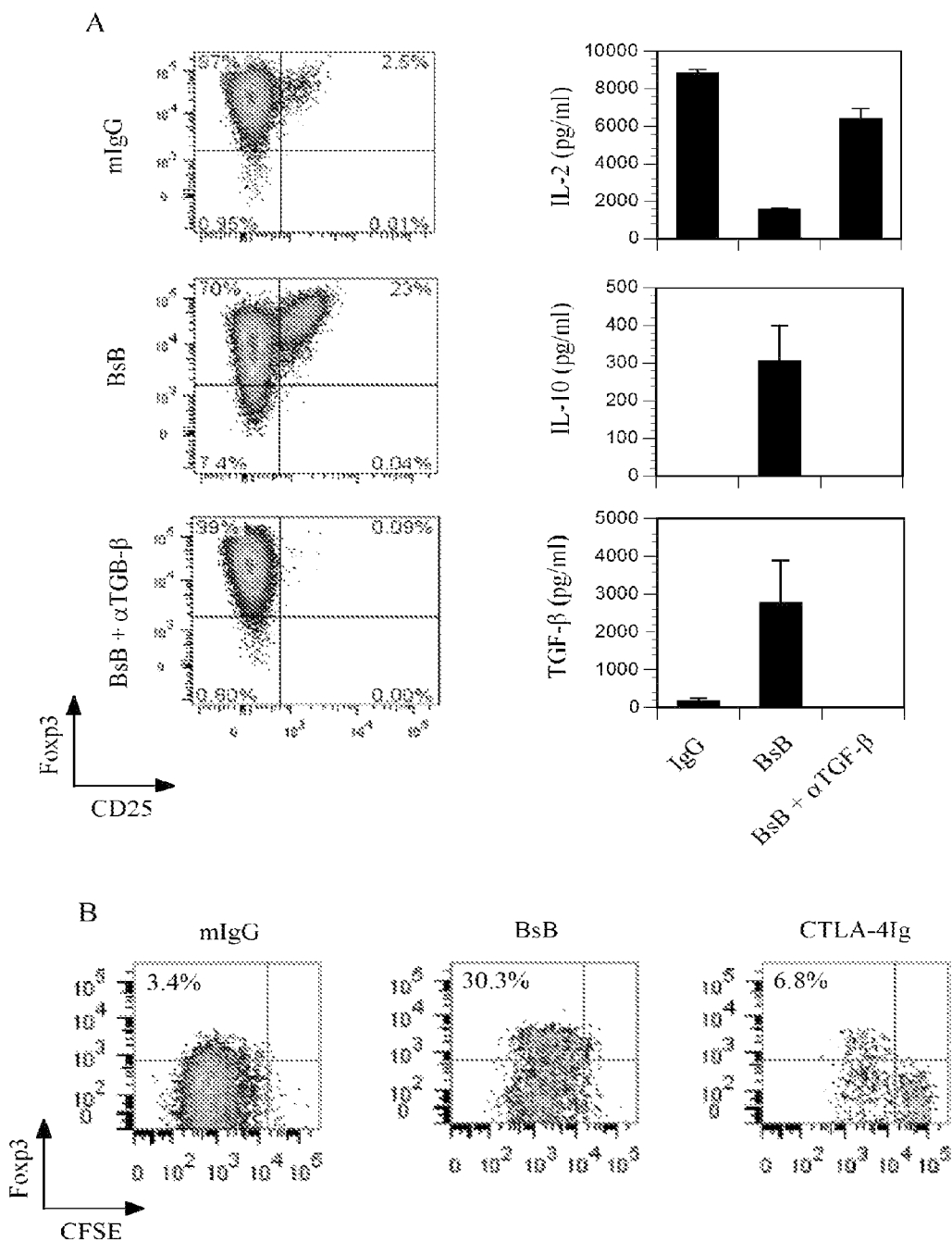

FIG. 4. BsB-mediated induction of antigen-specific Tregs in vitro. (A) In vitro induction of $Ova_{233-339}$-specific Tregs. Naïve OT-II T cells were mixed with LPS-activated and irradiated syngeneic APC in the presence of 0.5 µg/ml $OVA_{233-239}$ peptide. Control mIgG2a, BsB, and BsB plus an anti-TGF-β antibody (αTGF-β) were then added and tested as indicated (left panels). Cells were cultured for 5 days and then labeled with anti-CD25 and anti-Foxp3 antibodies before being analyzed by flow cytometry. IL-2, IL-10 and TGF-β levels in the culture media were assayed by ELISA (right panels). (B) Monitoring of induced Tregs proliferation. Studies were conducted as in A except naïve OT-II T cells were pre-labeled with CFSE before being mixed with APCs. Cells were gated on Foxp3 and CFSE fluorescent channels.

Figure 5:
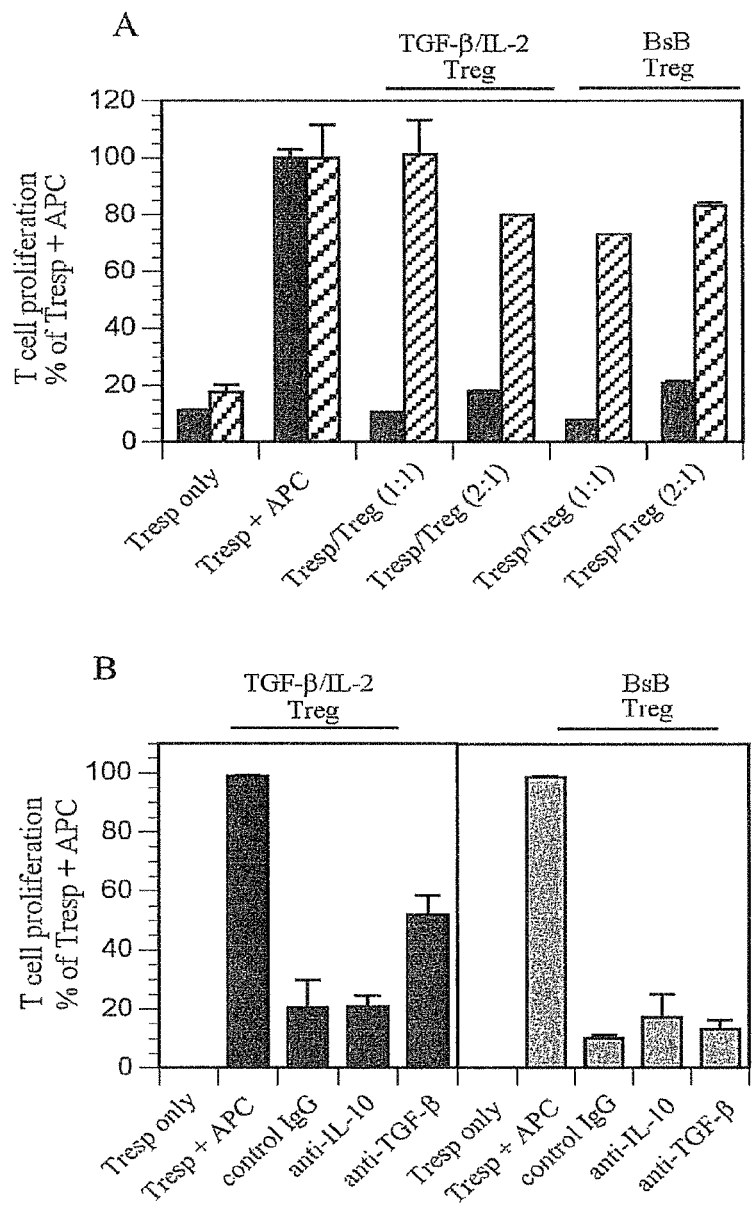

FIG. 5. Suppressive function of BsB-induced Tregs. (A) BsB- or TGF-β-induced Tregs were purified by flow cytometry and mixed with CFSE-labeled naïve responder T cells prepared from C57BL/6 mice at the indicated ratios in transwells (filled columns) or regular culture wells (hatched columns). LPS-treated allogenic BALB/c APCs were added to stimulate T cell activation. The results (mean+standard deviation) indicate the percentage of proliferating responder T cells (Tresp), based on a CFSE dilution without Tregs (Tresp+APC only) set to 100%. (B) Anti-IL-10 and anti-TGF-β antibodies were added to cells in regular culture wells at a Tresp:Treg ratio of 1:1 to determine the cytokines' contribution to T cell proliferation. The anti-TGF-β antibody partially inhibited the suppressive function of TGF-β-induced Tregs (left panel) but did not affect BsB-induced Tregs (right panel). The figure is representative of more than three independent but similar studies.

Figure 6:
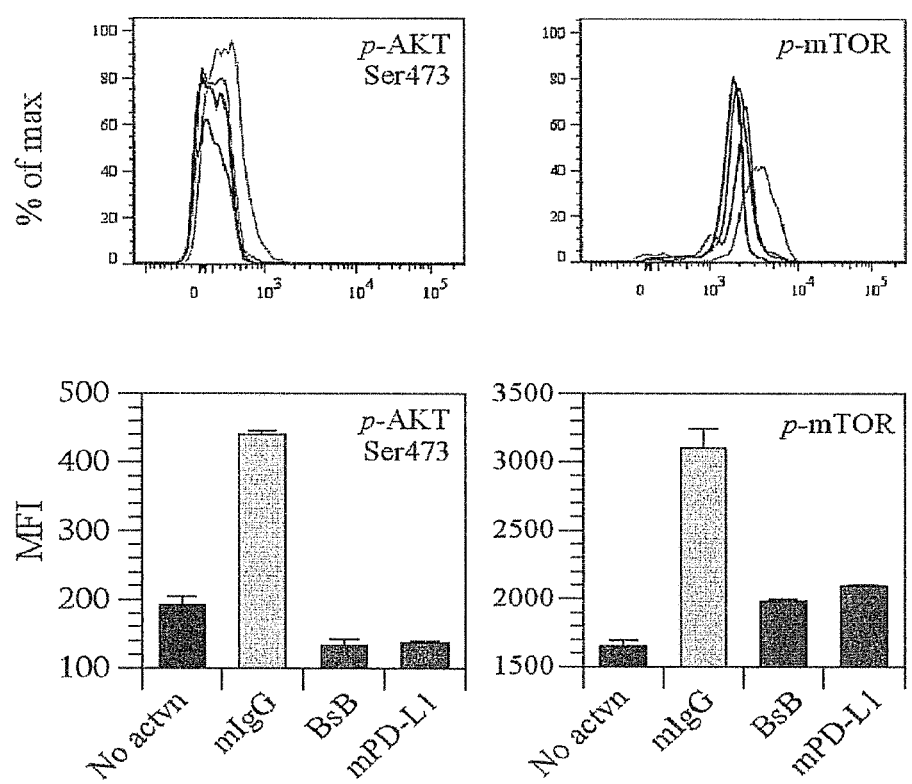

FIG. 6. Down-regulation of AKT and mTOR phosphorylation by BsB. Naïve T cells were cultured in round-bottom 96-well plates co-coated with anti-CD3, anti-CD28 and BsB, mouse IgG (mIgG) or mouse PD-L1 (mPD-L1) for 18 h. Cells deemed not activated were cultured in wells coated with IgG only. The phosphorylation status of AKT and mTOR was then monitored by flow cytometry after staining with fluorescently labeled antibodies to phosphorylated AKT and mTOR. MFI denotes mean fluorescent intensity. This figure represents one of three independent experiments.

Figure 7:
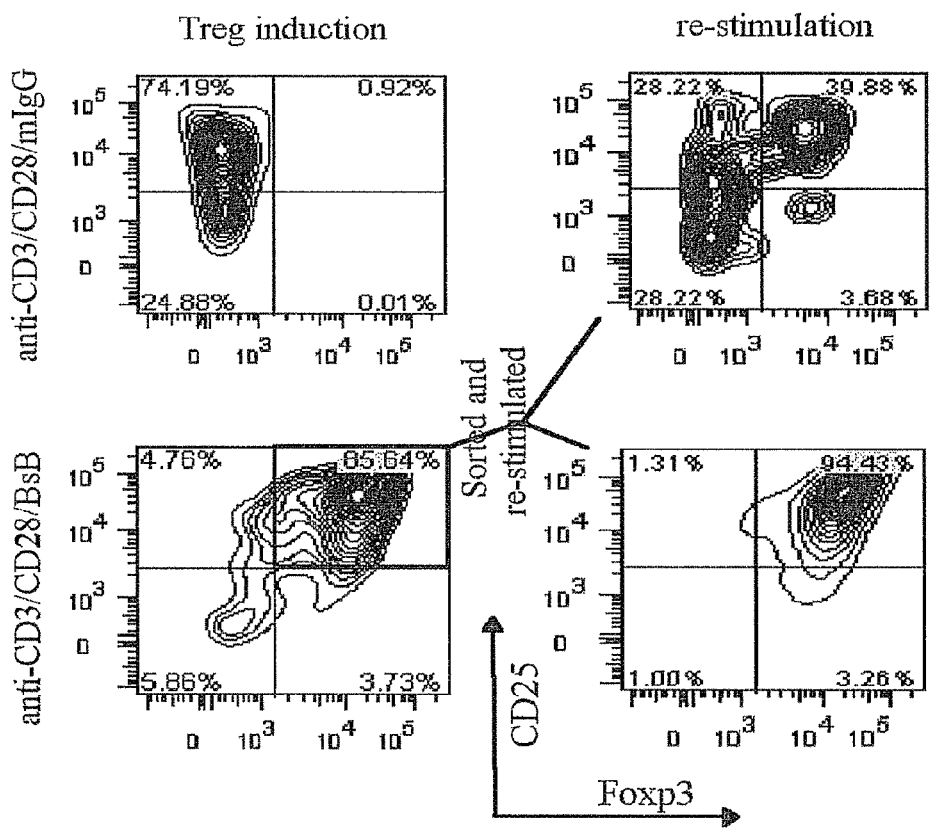

FIG. 7. Sustained Foxp3 expression in Tregs in response to continuous stimulation with BsB. Round-bottom 96-well plates were co-coated with anti-CD3, anti-CD28 and BsB or mouse IgG. Naïve T cells from Foxp3-EGFP knock-in mice were cultured for 5 days to induce Tregs (left panels), which were then purified from the BsB-treated cells (red square) and re-stimulated in another round of culture in co-coated wells, as above, for 5 days, before analysis by flow cytometry for GFP$^+$ cells. Re-culturing of purified Tregs with the mouse IgG control for 5 days resulted in a loss of Foxp3$^+$ expression in ~60% of cells (upper right quadrant of upper right panel), whereas less than 7% of the Tregs re-cultured with BsB had lost Foxp3$^+$ expression (upper right quadrant of bottom right panel). This figure represents one of three independent experiments.

Figure 8:
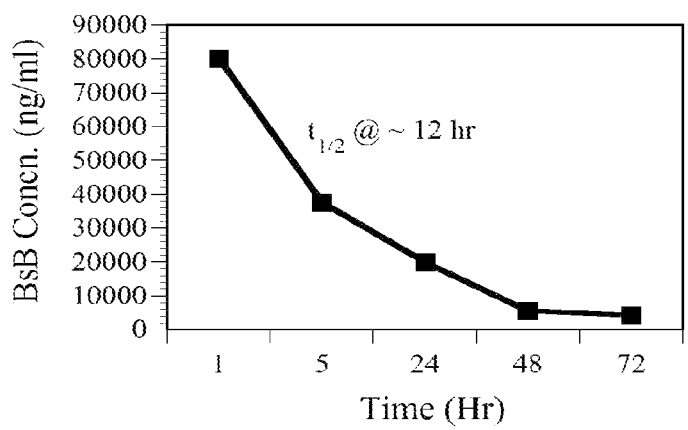
Figure 8:
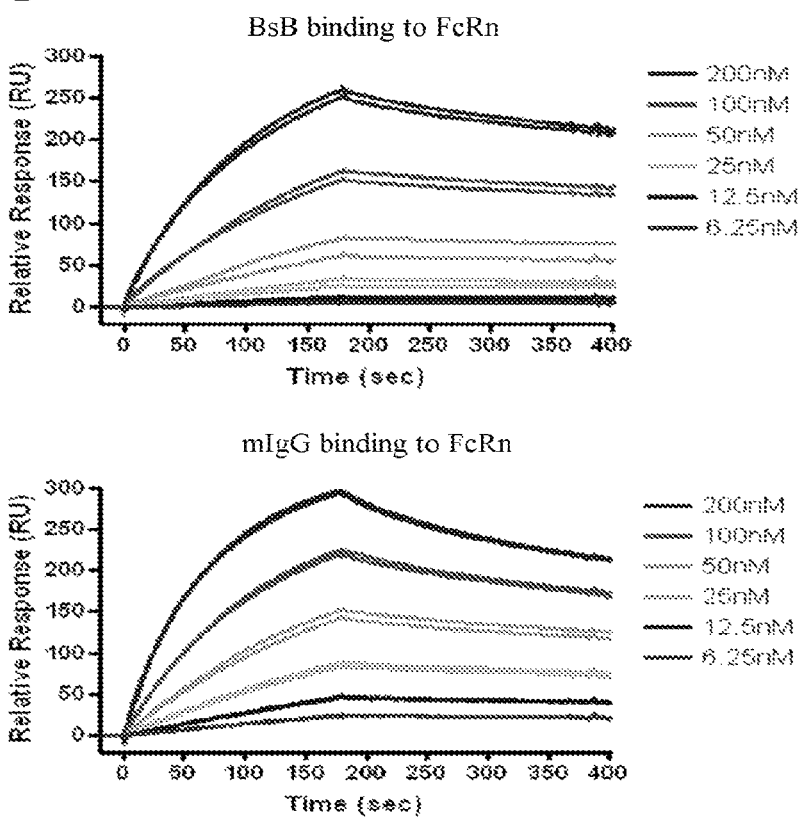

FIG. 8. Pharmacokinetics of BsB in vivo and biochemical analysis. (A) Pharmacokinetic profile of BsB in mice. Normal C57BL/6 mice (n=5) were dosed intraperitoneally with 20 mg/kg of BsB. Blood samples were collected at the different time points indicated and the levels of BsB levels determined using an ELISA. (B) Comparison of the binding of BsB and mouse IgG2a to FcRn. FcRn were immobilized to a Biacore chip. BsB or control mouse IgG2a was loaded onto the chip at various concentrations and the signals then recorded.

FIG. 9. Analysis of asparagine-linked glycosylation on BsB. The amino acid sequence of BsB was submitted to the NetNGlyc 1.0 Server for prediction of Asn-linked glycosylation sites. A total of 10 Asn-linked glycosylation sites (denoted N) were predicted; other amino acids are presented as dots. Monosaccharide composition of BsB was also performed to determine the composition of the glycans fucose (Fuc), N-acetylglucosamine (GlcNAc), galactose (Gal), mannose (Man), sialic acid (N-acetylneuramic acid). A sialic acid:galactose ratio of 0.68 indicates that about a third of the galactose residues are available for binding to the asialoglycoprotein receptor.

Figure 10:
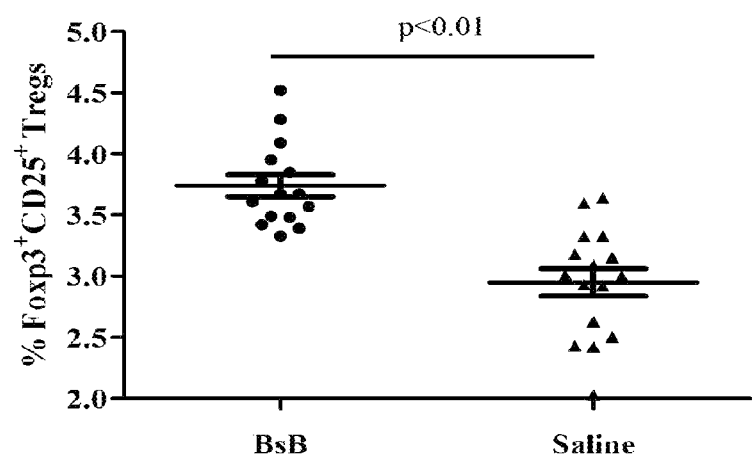
Figure 10:
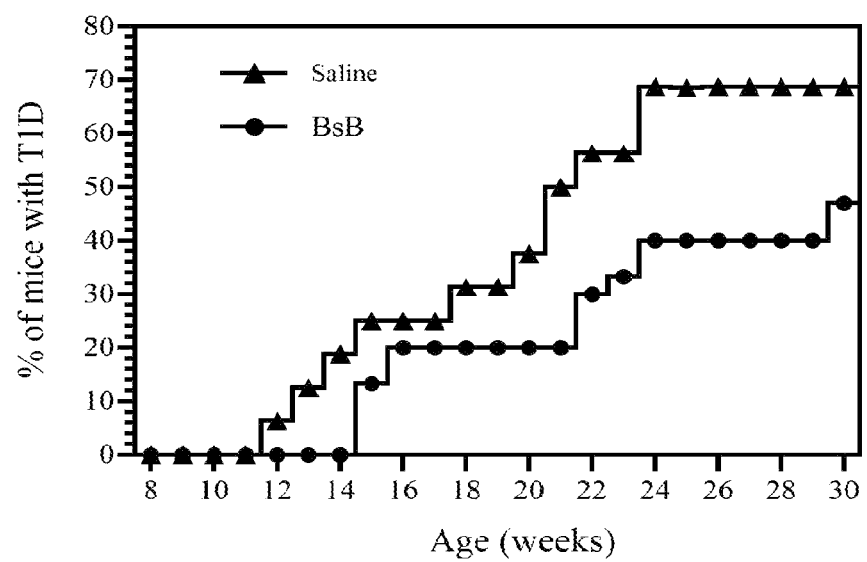

FIG. 10. Treatment of non-diabetic (NOD) mice with BsB delayed the onset of type 1 diabetes (T1D) in a late prevention treatment paradigm. (A) Levels of Foxp3$^+$ Tregs in the blood of BsB-treated NOD (closed circles, n=15) and saline-treated control NOD mice (closed triangles, n=14). There was a moderate but significant increase in the number of Tregs in the BsB-treated animals over that noted in the control animals. (B) Cumulative incidences of overt diabetes in NOD animals treated with BsB (filled circles) or saline (filled triangles).

Figure 11:
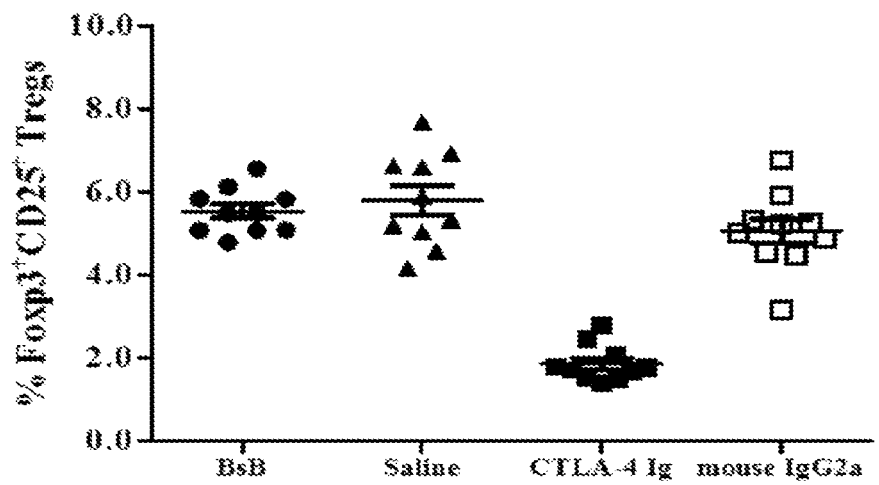
Figure 11:
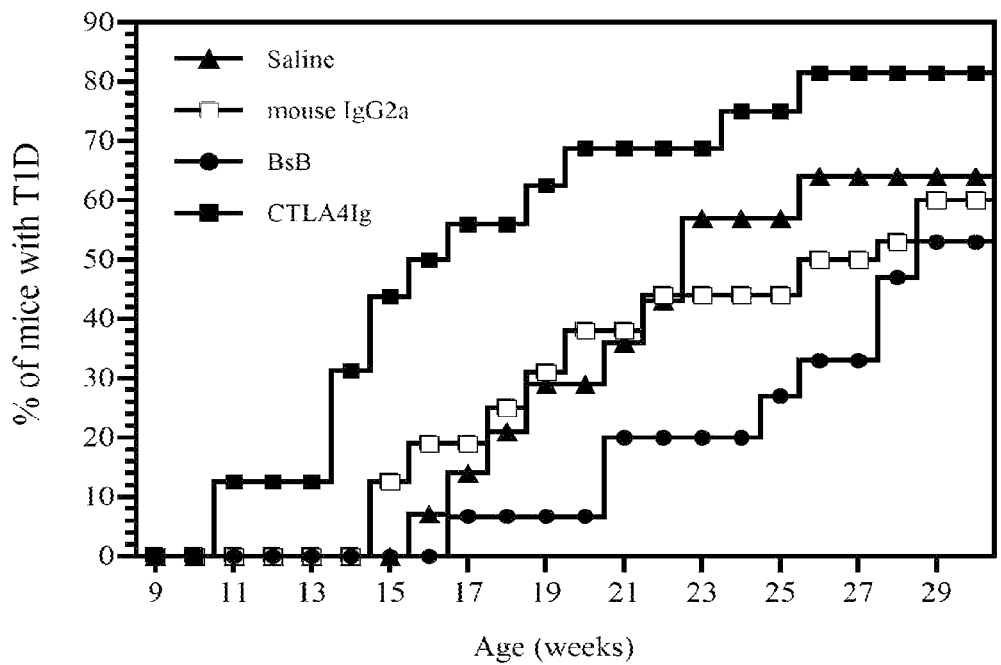

FIG. 11. Treatment of NOD mice with BsB delayed the onset of T1D in an early prevention treatment paradigm. (A) Levels of Foxp3$^+$ Tregs in the blood of mice treated with BsB (closed circles, n=10), saline (closed triangles, n=10), CTLA-4Ig (closed squares, n=10) and mouse IgG2a (open squares, n=10). No increase in the number of Foxp3$^+$ Tregs was detected after two weeks of treatment with BsB when compared to saline or mIgG2a-treated controls. However, treatment with CTLA-4Ig resulted in a statistically significant decrease in the number of Foxp3$^+$ Tregs in the blood.

(B) Cumulative incidences of overt diabetes in animals treated with BsB or controls. BsB treatment resulted in a significant delay in the onset of T1D when compared to the saline or mouse IgG2a-treated control groups before 24 weeks of age (p=0.04). However, no significant difference between the groups was noted at the end of the study. Data represent one of two separate studies with similar results, with total of 26 NOD mice in each group.

Figure 12:
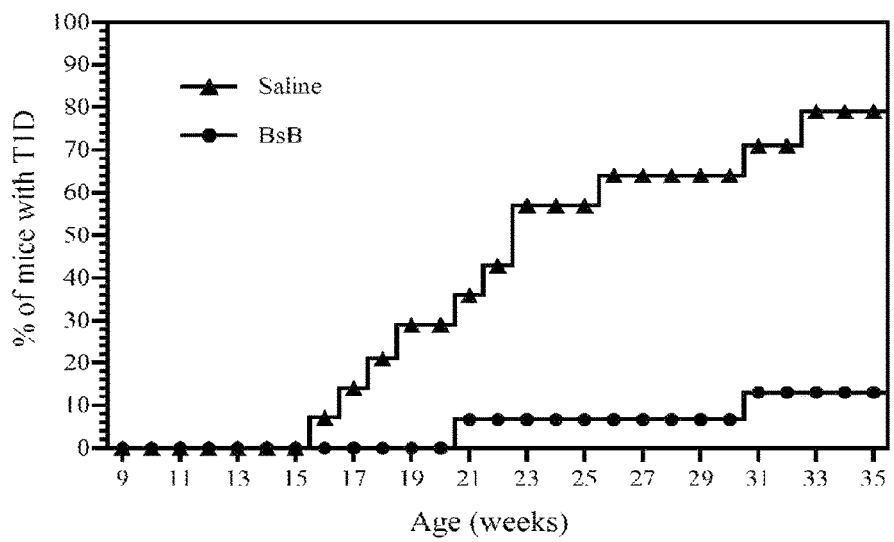
Figure 12:
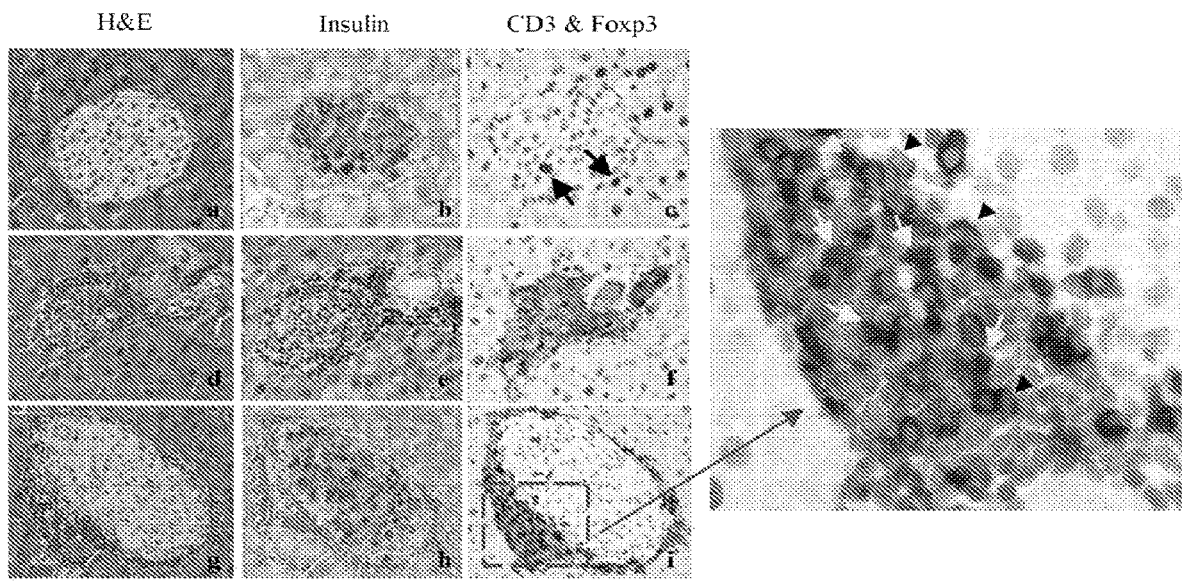

FIG. 12. Longer-term treatment of NOD mice with BsB significantly delayed the onset of T1D in NOD mice. (A) Cumulative incidences of overt diabetes in BsB-treated (n=16) and untreated mice (n=16). BsB treatment significantly reduced the incidence of T1D when compared to those treated with saline (p<0.01). (B) Histopathological analysis of pancreatic tissues from animals treated with saline or BsB. Panels a-c represent sections from saline-treated mice that remained non-diabetic with H&E, an antibody to insulin, or anti-CD3 and forkhead box P3 (Foxp3), respectively. Similar observations were noted in BsB-treated NOD mice that remained disease-free. No evidence of infiltration or insulitis was noted in any of the sections; a few Foxp3$^+$ Tregs may be present (arrows in panel c). Panels d-f represent pancreatic sections from diabetic NOD animals. Invasive insulitis was clearly evident and insulin-producing β-cells were completely destroyed (e). Some CD3$^+$ T cell infiltrations were also detected, along with few Tregs and many non-T cell leukocytes with blue nuclei (f). Panels g-i shows islets of BsB treated animals that remained non-diabetic exhibited characteristic peri-insulitis. Leukocyte infiltrations were noted but that were restricted to the periphery of the islets. Moreover, they were no notable destruction of the insulin-producing β-cells. Most of the leukocytes at the periphery were non-T cells. Enlarged inset (panel j, represents square in i) indicated Foxp3$^+$ Tregs (arrow head) were intermixed with other CD3$^+$ T cells and non-T cell leukocytes at the periphery of islets. Images were acquired with a 40× objective; the inset was acquired with a 60× objective, which was then further enlarged 3× digitally.

DETAILED DESCRIPTION OF THE INVENTION

Unless otherwise stated, all technical and scientific terms used herein have the same meanings as commonly understood by one of ordinary skill in the art to which this invention belongs. Any methods and materials with similar or equivalent function to those described herein can be used in the practice or testing of the present invention. Methods, devices, and materials suitable for such uses are now described. All publications cited herein are incorporated herein by reference in their entirety for the purpose of describing and disclosing the methodologies, reagents, and tools reported in the publications that might be used in connection with the invention.

The methods and techniques of the present application are generally performed according to conventional methods well known to those of skill in the art and as described in various general and more specific references that are cited and discussed throughout the present specification unless otherwise indicated. Such techniques are explained fully in the literature. See, e.g., Gennaro, A. R., ed. (1990) Remington's Pharmaceutical Sciences, 18th ed., Mack Publishing Co.; Hardman, J. G., Limbird, L. E., and Gilman, A. G., eds. (2001) The Pharmacological Basis of Therapeutics, 10th ed., McGraw-Hill Co.; Colowick, S. et al., eds., Methods In Enzymology, Academic Press, Inc.; Weir, D. M., and Blackwell, C. C., eds. (1986) Handbook of Experimental Immunology, Vols. I-IV, Blackwell Scientific Publications; Maniatis, T. et al., eds. (1989) Molecular Cloning: A Laboratory Manual, 2nd edition, Vols. I-III, Cold Spring Harbor Laboratory Press; Ausubel, F. M. et al., eds. (1999) Short Protocols in Molecular Biology, 4th edition, John Wiley & Sons; Ream et al., eds. (1998) Molecular Biology Techniques: An Intensive Laboratory Course, Academic Press; Newton, C. R., and Graham, A., eds. (1997) PCR (Introduction to Biotechniques Series), 2nd ed., Springer-Verlag.

The term "antibody", unless indicated otherwise, is used to refer to entire antibodies as well as antigen-binding fragments of such antibodies. For example, the term encompasses four-chain IgG molecules, as well as antibody fragments.

As used herein, the term "antibody fragments" refers to portions of an intact full length antibody—such as an antigen binding or variable region of the intact antibody. Examples of antibody fragments include Fab, Fab', F(ab')$_2$, and Fv fragments; diabodies; linear antibodies; single-chain antibody molecules (e.g., scFv); multispecific antibody fragments such as bispecific, trispecific, and multispecific antibodies (e.g., diabodies, triabodies, tetrabodies); binding-domain immunoglobulin fusion proteins; camelized antibodies; minibodies; chelating recombinant antibodies; tribodies or bibodies; intrabodies; nanobodies; small modular immunopharmaceuticals (SMIP), $V_{HH}$ containing antibodies; and any other polypeptides formed from antibody fragments, for example as further described below.

Antibodies may be of any class, such as IgG, IgA, or IgM; and of any subclass, such as IgG1 or IgG4. Different classes and subclasses of immunoglobulin have different properties, which may be advantageous in different applications.

Specificity, in the context of the present invention, requires that the claimed antibody be capable of selectively binding its defined cognate antigen, which is either CTLA-4 or the pMHC complex.

Naturally occurring immunoglobulins have a common core structure in which two identical light chains (about 24 kD) and two identical heavy chains (about 55 or 70 kD) form a tetramer. The amino-terminal portion of each chain is known as the variable (V) region and can be distinguished from the more conserved constant (C) regions of the remainder of each chain. Within the variable region of the light chain (also called the $V_L$ domain) is a C-terminal portion known as the J region. Within the variable region of the heavy chain (also called the $V_H$ domain), there is a D region in addition to the J region. Most of the amino acid sequence variation in immunoglobulins is confined to three separate locations in the V regions known as hypervariable regions or complementarity determining regions (CDRs) which are directly involved in antigen binding. Proceeding from the amino-terminus, these regions are designated CDR1, CDR2 and CDR3, respectively. The CDRs are held in place by more conserved framework regions (FRs). Proceeding from the amino-terminus, these regions are designated FR1, FR2, FR3 and FR4, respectively. The locations of CDR and FR regions and a numbering system have been defined by Kabat et al. (Kabat, E. A., et al., (1991) Sequences of Proteins of Immunological Interest, Fifth Edition, U.S. Department of Health and Human Services, U.S. Government Printing Office, and updates thereof which may be found online.

A humanized monoclonal antibody, as referred to herein, is an antibody which is composed of a human antibody framework, into which have been grafted CDRs from a non-human antibody. Procedures for the design and production of humanized antibodies are well known in the art, and have been described, for example, in Cabilly et al., U.S. Pat. No. 4,816,567; Cabilly et al., European Patent Application 0 125 023; Boss et al., U.S. Pat. No. 4,816,397; Boss et al., European Patent Application 0 120 694; Neuberger, M. S. et al., WO 86/01533; Neuberger, M. S. et al., European Patent Application 0 194 276 B1; Winter, U.S. Pat. No. 5,225,539; Winter, European Patent Application 0 239 400; Padlan, E. A. et al., European Patent Application 0 519 596. Further details on antibodies, humanized antibodies, human engineered antibodies, and methods for their preparation can be found in Kontermann, R. and Dübel, S. eds. (2001, 2010) Antibody Engineering, 2nd ed., Springer-Verlag, New York, N.Y., 2001.

Constant regions may be derived from any human antibody constant regions. Typically, variable region genes are cloned into expression vectors in frame with constant region genes to express heavy and light immunoglobulin chains. Such expression vectors can be transfected into antibody producing host cells for antibody synthesis.

Required antibody variable and constant regions may be derived from sequence databases. For example, immunoglobulin sequences are available in the IMGT/LIGM database (Giudicelli et al., (2006) *Nucleic Acids Res.* 34:(suppl. 1):D781-D784) or VBase (vbase.mrccpe.cam.ac.uk).

"Nucleic acids" as referred to herein typically include DNA molecules which encode the antibodies of the invention. Preferred are expression vectors, which are suitable for expressing the antibody genes in a host cell. Expression vectors and host cells for antibody gene expression are known in the art; see, for example, Morrow, K. J. (2008) *Genetic Engineering & Biotechnology News.* (Jun. 15, 2008) 28 (12), and Backliwal, G., et al. (2008) *Nucleic Acids Res.* 36 (15): e96-e96.

"CD80", as used herein, refers to mammalian CD80 antigen as well as to mutants thereof which have increased binding avidity or specificity for CTLA-4. See Linsley et al., (1994) *Immunity* 1:793-801, and Wu et al., (1997) *J. Exp. Med.* 185 (7):1327-1335, incorporated herein by reference. Mammalian CD80 can be selected from rodent, such as mouse, or human CD80.

"CD86", as used herein, refers to mammalian CD86 antigen as well as to mutants thereof which have increased binding avidity or specificity for CTLA-4. See Linsley et al., (1994) *Immunity* 1:793-801, incorporated herein by reference. Mammalian CD86 can be selected from rodent, such as mouse, or human CD86.

"CTLA-4", as used herein, refers to mammalian cytotoxic lymphocyte-associated antigen-4 (CTLA-4). The sequence of human CTLA-4 can be found in GenBank, Accession number AAH74893.1, GI:49904741. Mammalian CTLA-4 can be selected from rodent, such as mouse, or human CTLA-4.

"LAG-3", as used herein, refers to mammalian lymphocyte activation antigen 3 (LAG-3). The sequence for human LAG-3 can be found in Huard et al., (1997) *Proc. Natl. Acad. Sci, USA* 94:5744-5749, incorporated herein by reference. Mammalian LAG-3 can be selected from rodent, such as mouse, or human LAG-3.

The "MHC" is the complex involved in the presentation of antigen derived peptides by antigen-presenting cells, which is recognised by the TCR. In a certain aspect, the MHC is MHCII, which presents antigen to CD4$^+$ helper T-cells. See, for example, Wucherpfennig et al., *CSH Perspect. Biol.* 2 (4): a005140, epub 2010 Mar. 17.

A bispecific biologic, which may be referred to as a bispecific ligand, is a ligand which is capable of binding, or being bound by, two targets contemporaneously. Bispecific antibodies are known in the art, and are further described below. In the context of the present invention, the two targets are the CTLA-4 molecule on a T-cell and the MHC peptide complex on an APC. The bispecific biologic according to the invention can cross-link the two targets; by virtue of the pMHC binding to the TCR in the immune synapse, it therefore cross-links the CTLA-4 molecule to the TCR. A "biologic", in general, is a biological therapeutic or agent, which may be useful for, inter alia, therapeutic, diagnostic and/or research purposes.

A linker is any amino acid sequence which joins and separates two polypeptide domains in a protein. In the context of the bispecific ligand of the invention, the linker is the sequence which joins the CTLA-4 ligand to the MHC ligand. Exemplary linkers are sequences of amino acid, such as polyglycine, for example Gly-9. An alternative linker is an antibody Fc region. Such a linker spaces the two ligand domains by approximately 120 Å.

A ligand according to the invention may comprise antibody and non-antibody ligands in any combination. For example, the CTLA-4 ligand may be an anti-CTLA-4 antibody, and the MHC ligand may be LAG-3. Alternatively, CD80 may be used as the CTLA-4 ligand, in combination with LAG-3 or an anti-MHC antibody. Both ligands may be antibodies, or both may be the natural ligands, CD80 and LAG-3.

Cytotoxic Lymphocyte-associated Antigen-4 (CTLA-4)

Cytotoxic T lymphocyte associated antigen-4 (CTLA-4), also known as CD152, is a negative regulator of the T cell response, which plays an important role in the maintenance of T cell homeostasis and in the induction of self-tolerance (Karandikar et al., (1996) *J Exp Med* 184:783-788; Krummel and Allison, (1995) *J Exp Med* 182:459-465; Linsley and Golstein, (1996) *Curr Biol* 6:398-400; Walunas and Bluestone, (1998) *J Immunol* 160:3855-3860; Walunas et al., (1994) *J Immunol* 160:3855-3860). Mice deficient in CTLA-4 develop multi-organ autoimmune disease and typically succumb to the ailment by 4 weeks of age (Tivol et al., (1995) *Immunity* 3:541-547; Waterhouse et al., (1995) *Science* 270:985-988). The molecular mechanisms through which CTLA-4 modulate T cell activity are multifaceted and are thought to occur either intrinsically on conventional T cells or extrinsically through regulatory T cells (Tregs) (Ise et al., (2010) *Nat Immunol* 11:129-135; Jain et al., (2010) *Proc Natl Acad Sci USA* 107:1524-1528; Paterson and Sharpe, (2010) *Nat Immunol* 11:109-111).

These mechanisms include competing with CD28 for ligand binding (Linsley et al., (1994) *Immunity* 1:793-801), inducing the production of the tolerogenic enzyme indoleamine 2,3 dioxygenase in APC (Grohmann et al., (2002) *Nat Immunol* 3:1097-1101; Onodera et al., (2009) *J. Immunol* 183:5608-5614), and displacing CD28 from the immunological synapse (Pentcheva-Hoang et al., (2004) *Immunity* 21:401-413). CTLA-4 is homologous to the co-stimulatory molecule CD28 and shares the same ligands, CD80 (B7.1) and CD86 (B7.2), which are expressed on the surface of antigen presenting cells (APCs). However, differential binding of CD80/CD86 on APCs to CD28 and CTLA-4 on effector T cells leads to opposing outcomes, with CD28 triggering T cell activation and CTLA-4 causing T cell inhibition. Engagement of CTLA-4 by its ligands (CD80/86) on APC also stimulates the recruitment of the phosphatases SHP-1 (Guntermann and Alexander, (2002) *J. Immunol* 168:4420-4429) and PP2A (Baroja et al., (2002) *J. Immunol* 168:5070-5078; Chuang et al., (2000) *Immunity* 13:313-322) to the vicinity of the TCR of T cells undergoing activation. Consequent dephosphorylation of key signaling molecules associated with the TCR results in termination of T cell activation (Griffin et al., (2000) *J Immunol* 164:4433-4442). Moreover, interventions that promote early engagement of CTLA-4 with its ligands and crosslinking to the TCR result in premature dampening of key signaling signatures and consequent inhibition of T cell activation, leading to T cell hyporesponsiveness or anergy (Blair et al., (1998) *Immunol* 160:12-15; Griffin et al., (2000) *J. Immunol* 164:4433-4442; Krummel and Allison, (1996) *J Exp Med* 182:459-465; Walunas et al., (1996) *J Exp Med* 183:2541-2550).

To promote crosslinking of CTLA-4 to the TCR during the early phase of T cell activation a bispecific fusion protein (designated as "BsB") comprising a mutant CD80 (CD80w88a) and lymphocyte activation gene-3 (LAG-3) was generated. BsB was designed to concurrently engage CTLA-4 and MHCII in the immune synapse and thereby indirectly crosslink it to the TCR via the cognate pairing of MHCII with the TCR (Karman et al., (2012) *J Biol Chem* epub 2012 Feb. 15). In an allogenic MLR, BsB was shown to be effective at inhibiting T cell activation. Surprisingly, BsB also induced the production of IL-10 and TGF-β and promoted the differentiation of T cells undergoing activation to Tregs. IL-10 can exert broad immune suppressive properties through its ability to control the activation of macrophages and dendritic cells (DCs), as well as self-regulate Th1 cells (Ohata et al., (2007) *Arthritis Rheum* 56:2947-2956). TGF-β can act as an inhibitor of T cell differentiation (Kehrl et al., (1986) *J Exp Med* 163:1037-1050), macrophage activation (Tsunawaki et al., (1988) *Nature* 334:260-262; Wahl et al., (1990) *Ann N Y Acad Sci* 593:188-196) and dendritic cell maturation (Steinman et al., (2003) *Annu Rev Immunol* 21:685-711). In addition to their anti-inflammatory functions, IL-10 and TGF-β also purportedly can influence Treg function. For example, IL-10 has been shown to induce IL-10 producing Tr1 cells (Roncarolo et al., (2006) *Immunol Rev* 212:28-50) and to act on Foxp3$^+$ Tregs to maintain expression of Foxp3 and thereby propagate their suppressive function (Murai et al., (2009) *Nat Immunol* 10:1178-1184). Similarly, TGF-β has been reported to be necessary for the induction of Tregs (Chen et al., (2003) *J Exp Med* 198:1875-1886; Zheng et al., (2002) *J Immunol* 169:4183-4189) and in maintaining their suppressive function by promoting Foxp3 expression (Marie et al., (2005) *J Exp Med* 201:1061-1067).

Regulatory T Cells (Tregs)

Tregs are a functionally distinct subpopulation of T cells capable of controlling the immune responses to self and non-self antigens. A deficiency of Tregs results in a heightened immune response and presentation of autoimmune diseases (Sakaguchi et al., (1995) *J Immunol* 155:1151-1164). Extensive research has established a role of these specialized T cells in controlling all aspects of immune responses, in particular in engendering self-tolerance. Without being bound to a particular theory, these findings indicate that agents capable of boosting the in situ production of Tregs or the adoptive transfer of Tregs may be deployed to treat autoimmune diseases. Indeed, Treg cell-based therapies using freshly isolated or ex vivo expanded Tregs have been shown to be effective in treating animal models of type 1 diabetes (T1D) (Tang et al., (2004) *J Exp Med* 199:1455-1465; Tarbell et al., (2007) *J Exp Med* 204:191-201) and graft-versus-host disease (Anderson et al., (2004); Taylor et al., (2002) *Blood* 99:3493-3499; Zhao et al., (2008) *Blood* 112:2129-2138). In lieu of isolating and expanding Foxp3$^+$ CD4$^+$CD25$^+$ Tregs (often designated as natural Tregs or nTregs) from peripheral blood or lymph nodes, Tregs can be induced from naïve CD4$^+$CD25$^-$ T cells in the context of TCR activation and in the concomitant presence of TGF-β.

These Tregs are often referred to as adaptive Tregs (aTregs) or induced Tregs (iTregs). They are also Foxp3$^+$ and purportedly exhibit equally potent suppressive functions as nTregs (Chen et al., (2003) *J Exp Med* 198:1875-1886; Yamagiwa et al., (2001) *J Immunol* 166:7282-7289; Zheng et al., (2002) *J Immunol* 169:4183-4189). Adoptive transfers of aTregs or iTregs have been shown to be effective in conferring protection against autoimmune disease in an animal model of collagen-induced arthritis (Gonzalez-Rey et al., (2006) *Arthritis Rheum* 54:864-876). However, it is becoming more evident that antigen-specific Tregs offer a significantly higher therapeutic quotient than polyclonal Tregs with a pan-TCR repertoire (Masteller et al., (2005) *J Immunol* 175:3053-3059; Tang et al., (2004) *J Exp Med* 199:1455-1465; Tarbell et al., (2007) *J Exp Med* 204:191-201), with less potential side effect on pan-immune suppression. For this reason, we sought to evaluate the relative merits of BsB at producing antigen-specific Tregs in an antigen-specific T cell activation setting in vitro. Moreover, we tested its potential in treating autoimmune diabetes in the non-obese diabetic (NOD) mouse.

Type 1 Diabetes

Type 1 Diabetes (T1D) is an autoimmune disease caused by tissue specific destruction of insulin-producing pancreatic β-cells with consequent development of hyperglycemia. Non-obese diabetic (NOD) mice (female mice in particular) spontaneously develop autoreactive T cells towards islet-specific self-antigens (e.g. insulin and glutamic acid decarboxylase 65). In concert with other lymphocytes, these autoreactive T cells initiate the development of peri-insulitis between 3 and 4 weeks of age followed by invasive insulitis at 9 weeks and spontaneous overt diabetes between 12 and 35 weeks (Anderson and Bluestone, (2005) *Annu Rev Immunol* 23:447-485). NOD mice share many similarities to the disease in human subjects such as the production of pancreas-specific autoantibodies and activation of autoreactive CD4$^+$ and CD8$^+$ T cells. Susceptibility of these mice to autoimmunity, as in humans, is influenced by genes for the major histocompatibility complex (MHC), CTLA-4, and LAG-3. NOD mice harbor a unique major histocompatibility complex (MHC) haplotype (H-2$^{g7}$), which reportedly confers the highest risk for disease susceptibility (McDevitt et al., (1996) *Hormone and metabolic research* 28:287-288; Wicker et al., (1995) *Annu Rev Immunol* 13:179-200). CTLA-4 polymorphism has also been noted in NOD mice (Ueda et al., (2003) Nature 423:506-511) and in humans (Qu et al., (2009) *Genes and immunity* 10 Suppl 1:S27-32) and a deficiency of LAG-3 on the NOD background accelerates T1D onset with 100% penetrance (Bettini et al., (2011) *J Immunol* 187:3493-3498). Because BsB engages all these targets, the therapeutic merits of BsB were tested in this murine model of T1D.

Antibodies

The invention encompasses antigen-binding fragments of the antibodies set forth in the claims. As used herein, the term "fragments" refers to portions of the intact full length antibody—such as an antigen binding or variable region of the intact antibody. Examples of antibody fragments are set forth above.

The term "fragments" as used herein refers to fragments capable of binding the targets specified, the CTLA-4 molecule or the pMHC complex. These fragments may lack the Fc fragment of an intact antibody, clear more rapidly from the circulation, and can have less nonspecific tissue binding than an intact antibody. These fragments can be produced from intact antibodies using well known methods, for example by proteolytic cleavage with enzymes such as papain (to produce Fab fragments) or pepsin (to produce F(ab')$_2$ fragments), or expression of such fragments by recombinant technology.

The antibodies and fragments also encompass single-chain antibody fragments (scFv) that bind to the CTLA-4 molecule or the pMHC complex. An scFv comprises an antibody heavy chain variable region (V$_H$) operably linked to an antibody light chain variable region (V$_L$) wherein the heavy chain variable region and the light chain variable region, together or individually, form a binding site that binds CTLA-4 molecule or the pMHC complex. An scFv may comprise a V$_H$ region at the amino-terminal end and a V$_L$ region at the carboxy-terminal end. Alternatively, scFv may comprise a V$_L$ region at the amino-terminal end and a V$_H$ region at the carboxy-terminal end. Furthermore, although the two domains of the Fv fragment, V$_L$ and V$_H$, are coded for by separate genes, they can be joined, using recombinant methods, by a synthetic linker that enables them to be made as a single protein chain in which the V$_L$ and V$_H$ regions pair to form monovalent molecules (known as single chain Fv (scFv)). A scFv may optionally further comprise a polypeptide linker between the heavy chain variable region and the light chain variable region.

The antibodies and fragments also encompass domain antibody (dAb) fragments as described in Ward, E. S. et al. (1989) Nature 341:544-546 which consist of a V$_H$ domain.

The antibodies and fragments also encompass heavy chain antibodies (HCAb). These antibodies can apparently form antigen-binding regions using only heavy chain variable region, in that these functional antibodies are dimers of heavy chains only (referred to as "heavy-chain antibodies" or "HCAbs"). Accordingly, antibodies and fragments may be heavy chain antibodies (HCAb) that specifically bind to the CTLA-4 or pMHC targets.

The antibodies and fragments also encompass antibodies that are SMIPs or binding domain immunoglobulin fusion proteins specific for the CTLA-4 or pMHC targets. These constructs are single-chain polypeptides comprising antigen-binding domains fused to immunoglobulin domains necessary to carry out antibody effector functions (see WO 2005/017148).

The antibodies and fragments also encompass diabodies. These are bivalent antibodies in which V$_H$ and V$_L$ domains are expressed on a single polypeptide chain, but using a linker that is too short to allow for pairing between the two domains on the same chain. This forces the domains to pair with complementary domains of another chain and thereby creates two antigen-binding sites (see, for example, WO 93/11161). Diabodies can be bispecific or monospecific.

The antibody or antibody fragment thereof according to the invention does not cross-react with any target other than the intended CTLA-4 or pMHC targets.

The antibodies and fragments thereof may themselves be bispecific. For example, bispecific antibodies may resemble single antibodies (or antibody fragments) but have two different antigen binding sites (variable regions). Bispecific antibodies can be produced by various methods—such as chemical techniques, "polydoma" techniques or recombinant DNA techniques. Bispecific antibodies may have binding specificities for at least two different epitopes, for example one epitope on each of the CTLA-4 and pMHC targets.

Bispecific antibodies comprising complementary pairs of V$_H$ and V$_L$ regions are known in the art. These bispecific antibodies comprise two pairs of V$_H$ and V$_L$, each V$_H$V$_L$ pair binding to a single antigen or epitope. Such bispecific antibodies include hybrid hybridomas (Milstein, C. and Cuello, A. C., (1983) Nature 305 (5934): 537-40), minibodies (Hu et al., (1996) Cancer Res. 56:.3055-3061), diabodies (Holliger et al., (1993) Proc. Natl. Acad. Sci. USA 90:6444-6448; WO 94/13804), chelating recombinant antibodies (CRAbs) (Neri et al., (1995) J. Mol. Biol. 246, 367-373), biscFv (e.g., Atwell et al., (1996) Mol. Immunol. 33:1301-1312), "knobs in holes" stabilised antibodies (Carter et al., (1997) Protein Sci. 6:781-788). In each case each antibody species comprises two antigen-binding sites, each fashioned by a complementary pair of V$_H$ and V$_L$ domains. Each antibody is thereby able to bind to two different antigens or epitopes at the same time, with the binding to each antigen or epitope mediated by a V$_H$ and its complementary V$_L$ domain.

Natural autoantibodies have been described that are polyreactive (Casali and Notkins (1989) Ann. Rev. Immunol. 7: 515-531), reacting with at least two (usually more) different antigens or epitopes that are not structurally related. It has also been shown that selections of random peptide repertoires using phage display technology on a monoclonal antibody will identify a range of peptide sequences that fit the antigen binding site. Some of the sequences are highly related, fitting a consensus sequence, whereas others are very different and have been termed mimotopes (Lane and Stephen (1993) Current Opinion in Immunology 5:268-271). It is therefore clear that the binding site of an antibody, comprising associated and complementary V$_H$ and V$_L$ domains, has the potential to bind to many different antigens from a large universe of known antigens.

WO 03/002609 (Domantis) describes the production of dual specific antibodies in which each V$_H$V$_L$ pair possesses a dual specificity, i.e., is able to bind two epitopes on the same or different antigens. The conformation can be open or closed; in an open conformation, the two epitopes may be bound simultaneously, but in the closed conformation binding to the first epitope prevents or discourages binding to the second.

Non-immunoglobulin proteins with multiple binding specificities are known in nature; for example, a number of transcription factors bind both DNA and other protein molecules. However, methods for selecting binding peptides in the prior art only select peptides with single, not dual or multiple specificities.

Different research teams have previously tethered polypeptides with cysteine residues to a synthetic molecular structure (Kemp, D. S. and McNamara, P. E., (1985) J. Org. Chem. Timmerman, P. et al., (2005) ChemBioChem. 6 (5):821-4). Meloen and co-workers had used tris(bromomethyl)benzene and related molecules for rapid and quantitative cyclisation of multiple peptide loops onto synthetic scaffolds for structural mimicry of protein surfaces (Timmerman, P. et al., (2005) ibid). Methods for the generation of candidate drug compounds wherein said compounds are generated by linking cysteine containing polypeptides to a molecular scaffold as for example tris(bromomethyl)benzene are disclosed in WO 2004/077062 and WO 2006/078161. The selection of such molecules using display technology is described in WO 2009/098450. Dual specific embodiments are further described in WO 2010/089117.

The ligand, such as an antibody or fragment thereof, may be modified in order to increase its serum half-life, for example, by adding molecules—such as PEG or other water soluble polymers, including polysaccharide polymers to increase the half-life. In one embodiment, an antibody Fc region may be added to the bispecific linker according to the invention, to increase circulating half-life.

Antibody Production

Antibody production can be performed by any technique known in the art, including in transgenic organisms such as goats (see Pollock et al. (1999) *J. Immunol. Methods* 231: 147-157), chickens (see Morrow, K J J (2000) *Genet. Eng. News* 20:1-55), mice (see Pollock et al. ibid) or plants (see Doran P M (2000) *Curr. Opinion Biotechnol.* 11:199-204; Ma, J K-C (1998) Nat. Med. 4:601-606; Baez, J. et al. (2000) *BioPharm.* 13:50-54; Stoger, E. et al. (2000) *Plant Mol. Biol.* 42:583-590). Antibodies may also be produced by chemical synthesis; however expression of genes encoding the antibodies in host cells is preferred.

A polynucleotide encoding the antibody is isolated and inserted into a replicable construct or vector such as a plasmid for further propagation or expression in a host cell. Constructs or vectors (e.g., expression vectors) suitable for the expression of a humanized immunoglobulin according to the invention are available in the art. A variety of vectors are available, including vectors which are maintained in single copy or multiple copies in a host cell, or which become integrated into the host cell's chromosome(s). The constructs or vectors can be introduced into a suitable host cell, and cells which express a humanized immunoglobulin can be produced and maintained in culture. A single vector or multiple vectors can be used for the expression of a humanized immunoglobulin.

Polynucleotides encoding the antibody are readily isolated and sequenced using conventional procedures (e.g., oligonucleotide probes). Vectors that may be used include plasmid, virus, phage, transposons, minichromsomes of which plasmids are a typical embodiment. Generally such vectors further include a signal sequence, origin of replication, one or more marker genes, an enhancer element, a promoter and transcription termination sequences operably linked to the light and/or heavy chain polynucleotide so as to facilitate expression. Polynucleotides encoding the light and heavy chains may be inserted into separate vectors and introduced (e.g., by transformation, transfection, electroporation or transduction) into the same host cell concurrently or sequentially or, if desired both the heavy chain and light chain can be inserted into the same vector prior to such introduction.

A promoter can be provided for expression in a suitable host cell. Promoters can be constitutive or inducible. For example, a promoter can be operably linked to a nucleic acid encoding a humanized immunoglobulin or immunoglobulin chain, such that it directs expression of the encoded polypeptide. A variety of suitable promoters for prokaryotic and eukaryotic hosts are available. Prokaryotic promoters include lac, tac, T3. T7 promoters for *E. coli*; 3-phosphoglycerate kinase or other glycolytic enzymes e.g., enolase, glyceralderhyde 3-phosphate dehydrogenase, hexokinase, pyruvate decarboxylase, phosphofructokinase, glucose 6 phosphate isomerase, 3-phosphoglycerate mutase and glucokinase. Eukaryotic promoters include inducible yeast promoters such as alcohol dehydrogenase 2, isocytochrome C, acid phosphatase, metallothionein and enzymes responsible for nitrogen metabolism or maltose/galactose utilization; RNA polymerase II promoters including viral promoters such as polyoma, fowlpox and adenoviruses (e.g., adenovirus 2), bovine papilloma virus, avian sarcoma virus, cytomegalovirus (in particular the immediate early gene promoter), retrovirus, hepatitis B virus, actin, rous sarcoma virus (RSV) promoter and the early or late Simian virus 40 and non-viral promoters such as EF-1 alpha (Mizushima and Nagata (1990) *Nucleic Acids Res.* 18 (17):5322). Those of skill in the art will be able to select the appropriate promoter for expressing a humanized antibody or portion thereof of the invention.

Where appropriate, e.g., for expression in cells of higher eukaroytes, additional enhancer elements can be included instead of or as well as those found located in the promoters described above. Suitable mammalian enhancer sequences include enhancer elements from globin, elastase, albumin, fetoprotein, metallothionine and insulin. Alternatively, one may use an enhancer element from a eukaroytic cell virus such as SV40 enhancer, cytomegalovirus early promoter enhancer, polyoma enhancer, baculoviral enhancer or murine IgG2a locus (see WO 04/009823). Whilst such enhancers are typically located on the vector at a site upstream to the promoter, they can also be located elsewhere e.g., within the untranslated region or downstream of the polyadenylation signal. The choice and positioning of enhancer may be based upon compatibility with the host cell used for expression.

In addition, the vectors (e.g., expression vectors) typically comprise a selectable marker for selection of host cells carrying the vector and, in the case of a replicable vector, an origin of replication. Genes encoding products which confer antibiotic or drug resistance are common selectable markers and may be used in prokaryotic (e.g., β-lactamase gene (ampicillin resistance), Tet gene (tetracycline resistance) and eukaryotic cells (e.g., neomycin (G418 or geneticin), gpt (mycophenolic acid), ampicillin, or hygromycin resistance genes). Dihydrofolate reductase marker genes permit selection with methotrexate in a variety of hosts. Genes encoding the gene product of auxotrophic markers of the host (e.g., LEU2, URA3, HIS3) are often used as selectable markers in yeast. Use of viral (e.g., baculovirus) or phage vectors, and vectors which are capable of integrating into the genome of the host cell, such as retroviral vectors, are also contemplated.

In eukaryotic systems, polyadenylation and termination signals are operably linked to polynucleotide encoding the antibody of this invention. Such signals are typically placed 3' of the open reading frame. In mammalian systems, non-limiting examples of polyadenylation/termination signals include those derived from growth hormones, elongation factor-1 alpha and viral (e.g., SV40) genes or retroviral long terminal repeats. In yeast systems, non-limiting examples of polydenylation/termination signals include those derived from the phosphoglycerate kinase (PGK) and the alcohol dehydrogenase 1 (ADH) genes. In prokaryotic systems polyadenylation signals are typically not required and it is instead usual to employ shorter and more defined terminator sequences. The choice of polyadenylation/termination sequences may be based upon compatibility with the host cell used for expression. In addition to the above, other features that can be employed to enhance yields include chromatin remodeling elements, introns and host-cell specific codon modification. The codon usage of the antibody of this invention thereof can be modified to accommodate codon bias of the host cell such to augment transcript and/or product yield (e.g., Hoekema, A. et al. (1987) Mol Cell Biol. 7 (8):2914-24). The choice of codons may be based upon compatibility with the host cell used for expression.

The invention thus relates to isolated nucleic acid molecules that encode the humanized immunoglobulins, or heavy or light chains, thereof, of this invention. The invention also relates to isolated nucleic acid molecules that encode an antigen-binding portion of the immunoglobulins and their chains.

The antibodies according to this invention can be produced, for example, by the expression of one or more recombinant nucleic acids encoding the antibody in a suitable host cell. The host cell can be produced using any suitable method. For example, the expression constructs (e.g., one or more vectors, e.g., a mammalian cell expression vector) described herein can be introduced into a suitable host cell, and the resulting cell can be maintained (e.g., in culture, in an animal, in a plant) under conditions suitable for expression of the construct(s) or vector(s). Suitable host cells can be prokaryotic, including bacterial cells such as *E. coli* (e.g., strain DH5a™ (Invitrogen, Carlsbad, Calif.), PerC6 cells (Crucell, Leiden, NL), *B. subtilis* and/or other suitable bacteria; eukaryotic cells, such as fungal or yeast cells (e.g., *Pichia pastoris, Aspergillus* sp., *Saccharomyces cerevisiae, Schizosaccharomyces pombe, Neurospora crassa*), or other lower eukaryotic cells, and cells of higher eukaryotes such as those from insects (e.g., *Drosophila* Schnieder S2 cells, Sf9 insect cells (WO 94/126087 (O'Connor), TN5BI-4 (HIGH FIVE™) insect cells (Invitrogen), mammals (e.g., COS cells, such as COS-I (ATCC Accession No. CRL-1650) and COS-7 (ATCC Accession No. CRL-1651), CHO (e.g., ATCC Accession No. CRL-9096), CHO DG44 (Urlaub, G. and Chasin, L A., (1980) *Proc. Natl. Acac. Sci. USA*, 77 (7):4216-4220), 293 (ATCC Accession No. CRL-1573), HeLa (ATCC Accession No. CCL-2), CVI (ATCC Accession No. CCL-70), WOP (Dailey, L., et al., (1985) *J. Virol.*, 54:739-749), 3T3, 293T (Pear, W. S., et al., (1993) *Proc. Natl. Acad. Sci. USA*. 90:8392-8396), NSO cells, SP2/0 cells, HuT 78 cells and the like, or plants (e.g., tobacco, lemna (duckweed), and algae). See, for example, Ausubel, F. M. et al., eds. *Current Protocols in Molecular Biology*, Greene Publishing Associates and John Wiley & Sons Inc. (1993). In some embodiments, the host cell is not part of a multicellular organism (e.g., plant or animal), e.g., it is an isolated host cell or is part of a cell culture.

Host cells may be cultured in spinner flasks, shake flasks, roller bottles, wave bioreactors (e.g., System 1000 from wavebiotech.com) or hollow fibre systems but it is preferred for large scale production that stirred tank bioreactors or bag bioreactors (e.g., Wave Biotech, Somerset, N.J. USA) are used particularly for suspension cultures. Typically stirred tank bioreactors are adapted for aeration using e.g., spargers, baffles or low shear impellers. For bubble columns and airlift bioreactors, direct aeration with air or oxygen bubbles maybe used. Where the host cells are cultured in a serum free culture medium, the medium can be supplemented with a cell protective agent such as pluronic F-68 to help prevent cell damage as a result of the aeration process. Depending on the host cell characteristics, microcarriers maybe used as growth substrates for anchorage dependent cell lines, or the cells maybe adapted to suspension culture. The culturing of host cells, particularly vertebrate host cells, may utilize a variety of operational modes such as batch, fed-batch, repeated batch processing (see Drapeau et al (1994) *Cytotechnology* 15: 103-109), extended batch process or perfusion culture. Although recombinantly transformed mammalian host cells may be cultured in serum-containing media such media comprising fetal calf serum (FCS), it is preferred that such host cells are cultured in serum free media such as disclosed in Keen et al (1995) *Cytotechnology* 17:153-163, or commercially available media such as ProCHO-CDM or UltraCHO™ (Cambrex N.J., USA), supplemented where necessary with an energy source such as glucose and synthetic growth factors such as recombinant insulin. The serum-free culturing of host cells may require that those cells are adapted to grow in serum free conditions. One adaptation approach is to culture such host cells in serum containing media and repeatedly exchange 80% of the culture medium for the serum-free media so that the host cells learn to adapt in serum free conditions (see e.g., Scharfenberg K. et al (1995) in Animal Cell Technology Developments Towards the 21st Century (Beuvery E. C. et al eds), pp 619-623, Kluwer Academic publishers).

Antibodies according to the invention may be secreted into the medium and recovered and purified therefrom using a variety of techniques to provide a degree of purification suitable for the intended use. For example, the use of therapeutic antibodies of the invention for the treatment of human patients typically mandates at least 95% purity as determined by reducing SDS-PAGE, more typically 98% or 99% purity, when compared to the culture media comprising the therapeutic antibodies. In the first instance, cell debris from the culture media is typically removed using centrifugation followed by a clarification step of the supernatant using e.g., microfiltration, ultrafiltration and/or depth filtration. Alternatively, the antibody can be harvested by microfiltration, ultrafiltration or depth filtration without prior centrifugation. A variety of other techniques such as dialysis and gel electrophoresis and chromatographic techniques such as hydroxyapatite (HA), affinity chromatography (optionally involving an affinity tagging system such as polyhistidine) and/or hydrophobic interaction chromatography (HIC) (see U.S. Pat. No. 5,429,746) are available. In one embodiment, the antibodies of the invention, following various clarification steps, are captured using Protein A or G affinity chromatography followed by further chromatography steps such as ion exchange and/or HA chromatography, anion or cation exchange, size exclusion chromatography and ammonium sulphate precipitation. Typically, various virus removal steps are also employed (e.g., nanofiltration using, e.g., a DV-20 filter). Following these various steps, a purified preparation comprising at least 10 mg/ml or greater e.g., 100 mg/m; or greater of the antibody of the invention is provided and therefore forms an embodiment of the invention. Concentration to 100 mg/ml or greater can be generated by ultracentrifugation. Such preparations are substantially free of aggregated forms of antibodies of the invention.

Bacterial systems are particularly suited for the expression of antibody fragments. Such fragments are localized intracellularly or within the periplasm. Insoluble periplasmic proteins can be extracted and refolded to form active proteins according to methods known to those skilled in the art, see Sanchez et al. (1999) *J. Biotechnol.* 72:13-20; Cupit, P M et al. (1999) *Lett. Appl. Microbiol.* 29:273-277.

The present invention also relates to cells comprising a nucleic acid, e.g., a vector, of the invention (e.g., an expression vector). For example, a nucleic acid (i.e., one or more nucleic acids) encoding the heavy and light chains of a humanized immunoglobulin according to the invention, or a construct (i.e., one or more constructs, e.g., one or more vectors) comprising such nucleic acid(s), can be introduced into a suitable host cell by a method appropriate to the host cell selected (e.g., transformation, transfection, electroporation, infection), with the nucleic acid(s) being, or becoming, operably linked to one or more expression control elements (e.g., in a vector, in a construct created by processes in the cell, integrated into the host cell genome). Host cells can be maintained under conditions suitable for expression (e.g., in the presence of inducer, suitable media supplemented with appropriate salts, growth factors, antibiotic, nutritional supplements, etc.), whereby the encoded polypeptide(s) are produced. If desired, the encoded humanised antibody can be isolated, for example, from the host cells, culture medium, or milk. This process encompasses expression in a host cell (e.g., a mammary gland cell) of a transgenic animal or plant (e.g., tobacco) (see e.g., WO 92/03918).

CD80 Ligands

The design and construction of CD80 ligands is intended to maximise the specificity of the ligand for CTLA-4 over CD28. The sequence of CD80 is known in the art, cited example in Wu et al., 1997. CD80 comprises an extracellular Ig-V variable-like domain, and an intracellular IgC constant-like domain. In a preferred embodiment, the extracellular domain of CD80 is used as a ligand. For example, see SEQ ID NO: 15, especially residues 1-241.

Mutations can be made in human CD80 to improve binding affinity, and to improve selectivity for CTLA4 over CD28. See, for example, Wu et al., 1997.

Mutants other than W84A may be made, including K71G, K71V, S109G, R123S, R123D, G124L, S190A, S201A, R63A, M81A, N97A, E196A. See Peach et al., *JBC* 1995. 270 (6): 21181-21187. Assessment of binding affinity of mutants for both CTLA-4 and CD28 can be effected by site-directed mutagenesis followed by expression of the mutant polypeptides, and determination of Kd by surface plasmon resonance using CTLA-4 and CD28 Biacore chips. See, for example. Guo et al., (1995) *J. Exp. Med.* 181:1345-55.

Mutants having advantageous binding and selectivity profiles can be selected, and further assessed in cell based assays. For example, flow cytometry can be used to assay the effect of wild-type or mutant CD80 transfected into the cells.

LAG-3 Ligands

LAG-3 has been described in the art, and the binding site to the MHCII protein characterised. See Huard et al., (1997) *Proc. Natl. Acad. Sci. USA* 94 (11):5744-9. LAG-3 has four extracellular lg-like domains, and mutations can be introduced into these domains to optimise binding to MHCII.

The effectiveness of mutations can be analysed as described above in respect of CD80 ligands.

In one aspect, only domains 1 and 2 (D1 and D2) of the four 1 g-like domains of LAG-3 are used in a ligand according to the invention. It is believed that these domains are responsible for interaction with the MHCII protein.

Bispecific Ligand Constructs

The construction of a bispecific ligand follows the general formula "ligand-linker-ligand". Bispecific antibodies are known in the art, and are described above.

Construction of bispecific ligands preferably involved construction and expression of an appropriate gene encoding the desired polypeptide. Other methods of constructing by mixing the two polypeptides under conditions that permit covalent, ionic, or hydrophobic bonding. In preferred embodiments, it comprises covalently bonding the polypeptides. Where a bispecific molecule comprising three components is constructed, such as a CTLA-4 ligand, a linker and an MHC ligand, two of the three may be combined, bound together, and the third polypeptide subsequently added to the fusion product, and bound to create a fusion product comprising all three polypeptides.

Polypeptides in accordance with the present invention can be produced by any desired technique, including chemical synthesis, isolation from biological samples and expression of a nucleic acid encoding such a polypeptide. Nucleic acids, in their turn, can be synthesised or isolated from biological sources, and modified by site-directed mutagenesis if desired.

The invention thus relates to vectors encoding a bispecific ligand according to the invention, or a fragment thereof. The vector can be, for example, a phage, plasmid, viral, or retroviral vector.

Nucleic acids according to the invention can be part of a vector containing a selectable marker for propagation in a host. Generally, a plasmid vector is introduced in a precipitate, such as a calcium phosphate precipitate, or in a complex with a charged lipid.

If the vector is a virus, it can be packaged in vtro using an appropriate packaging cell line and then transduced into host cells.

The nucleic acid insert is operatively linked to an appropriate promoter, such as the phage lambda PL promoter, the *E. coli* lac, trp, phoA and tac promoters, the SV40 early and late promoters and promoters of retroviral LTRs. Other suitable promoters are known to those skilled in the art. The expression constructs further contain sites for transcription initiation, termination, and, in the transcribed region, a ribosome binding site for translation. The coding portion of the transcripts expressed by the constructs preferably includes a translation initiating codon at the beginning and a termination codon (UAA, UGA or UAG) appropriately positioned at the end of the polypeptide to be translated.

As indicated, the expression vectors preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells (e.g., *Saccharomyces cerevisiae* or *Pichia pastoris*); insect cells such as Drosophila S2 and Spodoptera Sf9 cells; animal cells such as CHO. COS, HEK293, and Bowes melanoma cells; and plant cells.

Appropriate culture media and conditions for the above-described host cells are known in the art and available commercially.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK2233, pKK233-3, pDR540, pRIT5 available from Pharmacia Biotech, Inc. Among preferred eukaryotic vectors are pWLNEO, pSV2CAT, p0G44, pXTI and pSG available from Stratagene; and pSVK3, pBPV, pMSG and pSVL available from Pharmacia. Among vectors preferred for use in mammalian cell expression include pSG5 Vector, pCMV˙SPORT6, pcDNA, pCEP4, pREP4, pCI, pSI and pBICEP-CMV. Preferred expression vectors for use in yeast systems include, but are not limited to pYES2, pYDI, pTEFI/Zeo, pYES2/GS, pPICZ, pGAPZ, pGAPZalph, pPIC9, pPIC3.5, pHILD2, pHIL-SI, pPIC3.5K, pPIC9K, and PA0815 (all available from Invitrogen, Carlsbad, Calif.).

Introduction of the construct into the host cell can be effected by calcium phosphate transfection. DEAE-dextran mediated transfection, cationic lipid-mediated transfection, electroporation, transduction, infection, or other methods. Such methods are described in many standard laboratory manuals, such as Sambrook et al., referred to above. A polypeptide according to the invention can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides according to the present invention can also be recovered from biological sources, including bodily fluids, tissues and cells, especially cells derived from tumour tissue or suspected tumour tissues from a subject.

In addition, polypeptides according to the invention can be chemically synthesised using techniques known in the art (for example, see Creighton, 1983, Proteins: Structures and Molecular Principles, W. H. Freeman & Co., N.Y., and Hunkapiller et al., (1984) *Nature*, 310:105-111). For example, a polypeptide comprising all or part of a bispecific ligand according to the invention can be synthesised by use of a peptide synthesiser.

Bispecific ligands in accordance with the invention are described in detail in the SEQ IDs appended hereto. SEQ ID NOs: 1 and 2 provide the mouse surrogate DNA and protein sequences of bispecific ligands in which the CTLA-4 ligand CD80w88a is paired with the MHC ligand LAG-3, separated by the IGg2a Fc region and a Gly-9 (G9) sequence. A terminal His tag (H6) sequence is provided at the C-terminus. SEQ ID NOs: 3 and 4 provide mouse surrogate DNA and protein sequences for the same constructs as SEQ ID NOs: 1 and 2, except that the IgG2a Fc region is placed C-terminal to the LAG-3 polypeptide, such that the CD80 and LAG-3 peptides are separated by G9 alone. The two arrangements, with the Fc region between the ligands or C-terminal thereto, are referred to as gene 1 and gene 2 constructs, respectively.

SEQ ID NOs: 5 and 6 provide human DNA and protein sequences in which wild-type sequence has been preserved. No mutations are made, either to CD80 or LAG-3.

In SEQ ID NOs: 7 and 8, a W84A mutation has been made to human CD80 (the equivalent of W88A in mouse) and an R75E mutation has been made in LAG-3. The remaining SEQ IDs (NOs: 7-14) describe other mutations in the CD80 and LAG-3 sequences.

Therapeutic Applications

Suppression of T cell activity is desirable in a number of situations in which immunosuppression is warranted, and/or an autoimmune condition occurs. Accordingly, targeting of the CTLA4/MHC interaction is indicated in the treatment of diseases involving an inappropriate or undesired immune response, such as inflammation, autoimmunity, and conditions involving such mechanisms. In one embodiment, such disease or disorder is an autoimmune and/or inflammatory disease. Examples of such autoimmune and/or inflammatory diseases are set forth above.

In one embodiment, such disease or disorder is Type 1 Diabetes (T1D).

In another embodiment, the ligands according to the invention are used to aid transplantation by immunosuppressing the subject. Such use alleviates graft-versus-host disease. For a description of existing treatments for graft-versus-host disease, see Svennilson, (2005) *Bone Marrow Transplantation* 35:S65-S67, and references cited therein. Advantageously, the antibodies of the invention may be used in combination with other available therapies.

With regard to the treatment of autoimmune diseases, combination therapy may include administration of a ligand of the present invention together with a medicament, which together with the ligand comprise an effective amount for preventing or treating such autoimmune diseases. Where said autoimmune disease is Type 1 diabetes, the combination therapy may encompass one or more of an agent that promotes the growth of pancreatic beta-cells or enhances beta-cell transplantation, such as beta cell growth or survival factors or immunomodulatory antibodies. Where said autoimmune disease is rheumatoid arthritis, said combination therapy may encompass one or more of methotrexate, an anti-TNF-α antibody, a TNF-α receptor-Ig fusion protein, an anti-IL-6, or anti-IL17, or anti-IL-15 or anti-IL-21 antibody, a non-steroidal anti-inflammatory drug (NSAID), or a disease-modifying anti-rheumatic drug (DMARD). For example, the additional agent may be a biological agent such as an anti-TNF agent (e.g., Enbrel®, infliximab (Remicade® and adalimumab (Humira®) or rituximab (Rituxan®). Where said autoimmune disease is hematopoietic transplant rejection, hematopoietic growth factor(s) (such as erythropoietin, G-CSF, GM-CSF, IL-3, IL-11, thrombopoietin, etc.) or antimicrobial(s) (such as antibiotic, antiviral, antifungal drugs) may be administered. Where said autoimmune disease is psoriasis, the additional agent may be one or more of tar and derivatives thereof, phototherapy, corticosteroids, Cyclosporine A, vitamin D analogs, methotrexate, p38 mitogen-activated protein kinase (MAPK) inhibitors, as well as biologic agents such as anti-TNF-α agents and Rituxan®. Where said autoimmune disease is an inflammatory bowel disease (TBD) such as, for example, Crohn's Disease or ulcerative colitis, the additional agent may be one or more of aminosalicylates, corticosteroids, immunomodulators, antibiotics, or biologic agents such as Remicade® and Humira®.

The combination treatment may be carried out in any way as deemed necessary or convenient by the person skilled in the art and for the purpose of this specification, no limitations with regard to the order, amount, repetition or relative amount of the compounds to be used in combination is contemplated. Accordingly, the antibodies according to the present invention for use in therapy may be formulated into pharmaceutical compositions. The present invention is also related to pharmaceutical compositions comprising peptides according to the present invention.

Pharmaceutical Compositions

In a preferred embodiment, there is provided a pharmaceutical composition comprising a bispecific ligand according to the invention, or a ligand or ligands identifiable by an assay method as defined in the previous aspect of the invention. Ligands may be immunoglobulins, peptides, nucleic acids or small molecules, as discussed herein. They are referred to, in the following discussion, as "compounds".

A pharmaceutical composition according to the invention is a composition of matter comprising a compound or compounds capable of modulating T-cell activity as an active ingredient. Typically, the compound is in the form of any pharmaceutically acceptable salt, or e.g., where appropriate, an analog, free base form, tautomer, enantiomer racemate, or combination thereof. The active ingredients of a pharmaceutical composition comprising the active ingredient according to the invention are contemplated to exhibit excellent therapeutic activity, for example, in the treatment of graft-versus-host disease, when administered in amount which depends on the particular case.

In another embodiment, one or more compounds of the invention may be used in combination with any art recognized compound known to be suitable for treating the particular indication in treating any of the aforementioned conditions. Accordingly, one or more compounds of the invention may be combined with one or more art recognized compounds known to be suitable for treating the foregoing indications such that a convenient, single composition can be administered to the subject. Dosage regimen may be adjusted to provide the optimum therapeutic response.

For example, several divided doses may be administered daily or the dose may be proportionally reduced as indicated by the exigencies of the therapeutic situation.

The active ingredient may be administered in a convenient manner such as by the oral, intravenous (where water soluble), intramuscular, subcutaneous, intranasal, intradermal or suppository routes or implanting (e.g., using slow release molecules).

Depending on the route of administration, the active ingredient may be required to be coated in a material to protect said ingredients from the action of enzymes, acids and other natural conditions which may inactivate said ingredient.

In order to administer the active ingredient by other than parenteral administration, it will be coated by, or administered with, a material to prevent its inactivation. For example, the active ingredient may be administered in an adjuvant, co administered with enzyme inhibitors or in liposomes. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin.

Liposomes include water-in-oil-in-water CGF emulsions as well as conventional liposomes.

The active ingredient may also be administered parenterally or intraperitoneally.

Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants.

The prevention of the action of microorganisms can be brought about by various antibacterial and antifungal agents, for example, parabens, chlorobutanol, phenol, sorbic acid, thirmerosal, and the like. In certain cases, it may be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active ingredient in the required amount in the appropriate solvent with various of the other ingredients enumerated above, as required, followed by filtered sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

As used herein "pharmaceutically acceptable carrier and/or diluent" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such as active material for the treatment of disease in living subjects having a diseased condition in which bodily health is impaired.

The principal active ingredients are compounded for convenient and effective administration in effective amounts with a suitable pharmaceutically acceptable carrier in dosage unit form. In the case of compositions containing supplementary active ingredients, the dosages are determined by reference to the usual dose and manner of administration of the said ingredients.

In order to facilitate delivery of peptide compounds, including antibodies, to cells, peptides may be modified in order to improve their ability to cross a cell membrane. For example, U.S. Pat. No. 5,149,782 discloses the use of fusogenic peptides, ion-channel forming peptides, membrane peptides, long-chain fatty acids and other membrane blending agents to increase protein transport across the cell membrane. These and other methods are also described in WO 97/37016 and U.S. Pat. No. 5,108,921, incorporated herein by reference.

In a further aspect there is provided the active ingredient of the invention as hereinbefore defined for use in the treatment of disease either alone or in combination with art recognized compounds known to be suitable for treating the particular indication. Consequently there is provided the use of an active ingredient of the invention for the manufacture of a medicament for the treatment of disease associated with an aberrant immune response.

Moreover, there is provided a method for treating a condition associated with an aberrant immune response, comprising administering to a subject a therapeutically effective amount of a ligand identifiable using an assay method as described above.

The invention is further described, for the purposes of illustration only, in the following examples.

EXAMPLES

Example 1

Design of a Bispecific Fusion Protein that Engages CTLA-4 and Crosslinks it to the TCR via MHC 11.

To generate a bispecific fusion protein that selectively and agonistically engages CTLA-4 and simultaneously ligates it to the TCR, mutant CD80 (CD80w88a, referred to hereafter as CD80wa) that binds CTLA-4 but has minimal affinity for CD28 (Wu et al., 1997) was fused to LAG-3, a natural ligand of MHCII (Baixeras et al., 1992; Triebel et al., 1990). CD80wa was joined to LAG-3 using a linker composed of nine glycines, which in turn was attached to the Fc portion of mouse IgG2a to purportedly increase its circulating half-life (FIG. 1A). In response to a ligand of this configuration, CTLA-4 engagement and ligation to the TCR were expected to occur indirectly, via formation of the tri-molecular complex (CTLA-4/MHCII/TTCR) in the immune synapses during early T cell activation (FIG. 1B). Conceptually, outside of the context of the immune synapse, binding of the bispecific fusion protein to either CTLA-4 or MHCII alone or to both CTLA-4 and MHCII should not lead to inhibition of T cell activity. The engagement of CTLA-4 by CD80wa was designed to trigger CTLA-4 signaling via the recruitment of phosphatases to the cytoplasmic tail of CTLA-4. Meanwhile, binding of LAG-3 to MHCII was intended to bring CTLA-4 into the proximity of the cognate TCR, which binds the pMHCII complex in the immune synapse (FIG. 1B). The combination of these two binding events was expected to deliver an inhibitory signal to the TCR. A control fusion protein comprising CD80wa and IgG2a Fc was also constructed (FIG. 1A), which should not be capable of crosslinking CTLA-4 to the TCR (FIG. 1C) as it lacks LAG-3.

The test and control fusion proteins were expressed in Chinese hamster ovary cells and purified with affinity chromatography on a protein G column. Aggregates were removed using size exclusion chromatography. The test bispecific fusion protein (CD80wa-LAG-3-Fc) is referred to as BsB (nucleotide sequence: SEQ ID NO. 3; amino acid sequence: SEQ ID NO: 4), and the control construct (CD80wa-Fc) is known as BsBΔ (nucleotide sequence: SEQ ID NO. 16; amino acid sequence: SEQ ID NO: 17). As expected, both fusion proteins appeared as dimers on non-reducing SDS-PAGE gels (BsB, 200 kDa; BsBΔ 140 kDa) and as monomers (BsB, 100 kDa; BsBΔ 70 kDa) on reducing SDS-PAGE gels. Their identities were further confirmed by Western blotting, using antibodies against LAG-3 and CD80.

Example 2

BsB Inhibits T cell Activation in an Allogenic Mixed Lymphocyte Reaction.

The relative ability of BsB and BsBΔ to inhibit T cell activation was assessed in an allogenic mixed lymphocyte reaction by measuring the production of IL-2. Naïve CD4+ CD25− CD62L$^{high}$CD44$^{low}$ T cells that had been purified from BALB/c mice were mixed with APCs isolated from C57BL/6 mice in the presence or absence of the BsB or BsBΔ. Murine IgG2a and CTLA-4Ig, a co-stimulation inhibitor that binds to CD80/86 and blocks their binding to CD28, were included as negative and positive controls, respectively. Inclusion of BsB but not BsBΔ in the mixed lymphocyte reaction inhibited TL-2 production albeit not to the same extent as that achieved by CTLA-4Ig (FIG. 2). This difference was likely the result of BsB-mediated T cell inhibition occurring later than CTLA-4Ig-mediated inhibition. More specifically, for BsB, inhibition only occurred after CTLA-4 was upregulated following T cell activation. The inability of BsBΔ to reduce IL-2 production strongly suggests that engagement of CTLA-4 alone is insufficient to prevent T cell activation because concurrent crosslinking to the TCR is required. To exclude the possibility that the LAG-3 portion of BsB plays a role in T cell inhibition, LAG-3Ig was tested in this assay and verified not to inhibit T cell activation.

Example 3

BsB Directs T Cell Differentiation into Tregs.

Early termination of TCR signaling by withdrawal of antigen stimulation, inhibition of mTOR signaling, suboptimal TCR stimulation due to a low affinity antigen, or weak co-stimulation during T cell activation have been shown to induce Foxp3+ expression and skew T cell differentiation toward a Treg phenotype (Delgoffe et al., (2009) *Immunity* 30:832-844; Haxhinasto et al., (2008) *J. Exp. Med.* 205:565-574; Sauer et al., (2008) *Proc. Natl. Acad. Sci. USA* 105: 7797-7802). As BsB forces early engagement of the TCR by activation-induced CTLA-4 with consequent attenuation of TCR signaling, its ability to generate Foxp3+ Tregs was also evaluated. Naïve CD4+CD62L$^{high}$GFP" T cells prepared from Foxp3-EGFP knock-in mice (Haribhai et al., (2007) *J. Immunol* 178:2961-2972) were mixed with LPS-treated allogenic APCs in the presence of BsB or BsBΔ. Flow cytometry analysis of the cells after five days of culture revealed a large number of CD4+CD25+GFP+ T cells among the BsB-treated cells (FIG. 3A, middle left panel) but not among cells treated with mouse IgG2a (FIG. 3A, top left panel) or the BsBΔ control (FIG. 3A, bottom left panel), suggesting that these CD4+CD25+ GFP+ T cells were Foxp3+ Tregs. To confirm this finding, cell culture media were collected and assayed for the signature Treg cytokines, IL-10 and TGF-β (Cools et al., (2008) *J. Cell Mol. Med.* 12:690-700). Large amounts of 1L-10 and TFG-β were detected in the media of BsB-treated cells (FIG. 3A, left panels) but not in media of cells treated with BsBΔ or mIgG2a. Surprisingly, CTLA-4Ig did not induce generation of GFP+ Tregs or IL-10 and TGF-β production. Without being bound to a particular theory, the mechanism by which CTLA-4Ig curtails the T cell response is different from that of BsB. LAG-3Ig alone or in combination with BsBΔ also failed to induce generation of GFP+Tregs, suggesting that BsB-mediated crosslinking of CTLA-4 with the TCR was required for Treg induction.

Example 4

Induction of Tregs by BsB Requires Self-stimulated TGF-β

The concurrent detection of elevated levels of IL-10 and TGF-β following treatment with BsB raised the possibility that the cytokines, TGF-β in particular, played a role in facilitating the generation of Tregs (FIG. 3A). To address this, culture media were collected over a period of five days and analyzed for cytokine and Foxp3+ Treg content. Elevated IL-10 and TGF-β levels were detected as early as day 2 post-treatment, and Foxp3+ Tregs were detected after day 3. Without being bound to a particular theory, the endogenous production of TGF-β presumably stimulated by BsB, is involved in Treg differentiation. Addition of an anti-TGF-β antibody (clone 1D11), but not an isotype control IgG (clone 13C4), to the Treg induction assay completely blocked the appearance of Foxp3+ Tregs (FIG. 3B). Without being bound to a particular theory, the early engagement of CTLA-4 and its subsequent crosslinking to the TCR by BsB stimulated endogenous TGF-β production, which in turn encouraged Treg differentiation. Crosslinking of CTLA-4 and the TCR has been previously reported to induce TGF-β production (Chen et al., (1998) *J. Exp. Med.* 188:1849-1857), although Treg differentiation was not assessed in this study.

Tregs have shown considerable therapeutic potential in modulating the disease manifestations in several animal models of autoimmune diseases. However, the importance of the specificity of the induced Tregs against the relevant antigens has been highlighted. Non-antigen specific Tregs that will not be activated against particular autoantigens in the context of autoantigen-specific reactive T cells are presumably not functionally immunosuppressive. Hence, approaches that facilitate the generation of large numbers of antigen-specific Tregs are highly desirable for treating these ailments. Moreover, strategies that facilitate the de novo induction of antigen-specific Tregs in situ (e.g. in islets of pancreas for T1D or in the lamina propria for ulcerative colitis or Crohn's disease) are preferred over the use of adoptive transfer of in vitro differentiated or expanded Tregs.

Example 5

BsB-induced Tregs are Functionally Suppressive in a Cell-cell Contact-dependent Manner.

To assess whether the BsB-induced Tregs were functionally suppressive, BsB-induced Tregs and TGF-β-induced Tregs, which served as a control, were purified using fluorescence-activated cell sorting (FACS) and mixed with CFSE-labeled syngeneic responder T cells at different ratios and allogenic APCs. Cells were co-cultured for three days in either transwells or regular culture wells, after which the proliferation of responder T cells was analyzed using flow cytometry. As summarized in FIG. 5A, both BsB- and TGF-β-induced Tregs cultured in regular culture wells almost completely inhibited the proliferation of the responder T cells. The potency of the suppressive activity of the BsB-induced Tregs was comparable to that of TGF-β-induced Tregs. In contrast, Tregs generated by either BsB or TGF-β did not significantly inhibit the proliferation of responder T cells when the T cells were separated from the Tregs in a transwell. Without being bound to a particular theory, Treg suppressive activity depended on cell-cell contact and was not mediated by secreted cytokines or other factors. Supporting this notion, inclusion of an antibody to IL-10 (clone JES5-2A5) in the regular culture well did not affect the suppressive activity of either the BsB- or the TGF-β-induced Tregs (FIG. 5B). The addition of an antibody to TGF-β1D11 also did not affect the suppressive activity of BsB-induced Tregs, although it partially reduced suppression by TGF-β-induced Tregs (FIG. 5B).

Example 6

BsB Directs Differentiation of OT-II T Cells into Antigen-specific Tregs.

As it was found that a bifunctional fusion protein comprising CD80wa and LAG3 (BsB) that crosslinks CTLA-4 to the TCR (via MHCII) can induce the production of Foxp3+ Tregs in an allogenic MLR, the potential of BsB at eliciting the production of antigen-specific Tregs was examined. To investigate this prospect, naïve OT-II T cells were purified from transgenic mice harboring transgenes encoding the TCR (α- and β-subunits) specific for a chicken ovalbumin peptide (323-339) (Barnden et al., 1998) and mixed with syngeneic APCs in the presence of Ova323-339. After 5 days of culture, significantly greater amounts of Foxp3+ Tregs were detected in OT-II T cells that had been treated with BsB (FIG. 4A, middle left panel) than by the mIgG control (FIG. 4A, upper left panel) or by CTLA-4Ig (data not shown). This induction of Tregs was inhibited by the inclusion of anti-TGF-β antibody in the cultures (FIG. 4A, bottom left panel). Without being bound to a particular theory, differentiation was mediated by endogenously produced TGF-β in an autocrine or paracrine manner. Levels of IL-2 were decreased while those of IL-10 and TGF-β were increased in the media of BsB-treated cells (FIG. 4A, right panels).

To monitor the proliferative activity of the induced Tregs, OT-II cells were preloaded with the fluorescent tracer, CFSE. As shown in FIG. 4B, BsB-induced Foxp3+ Tregs were determined to be proliferative as indicated by a dilution of the CFSE signal. As expected, the addition of CTLA-4Ig, a co-stimulatory blocker, reduced T cell proliferation. Hence, BsB was able to inhibit T cell activation and induce the production of Tregs in both an allogenic MLR and antigen-specific setting.

Example 7

Induction of Tregs by BsB may Involve Attenuation of the AKT/mTOR Signaling Pathway.

Recent reports have indicated that the AKT and mTOR signaling pathways play important roles in determining T cell fate. The presence of constitutively active AKT in T cells diminishes Treg differentiation in a rapamycin-sensitive manner (Haxhinasto et al., 2008), suggesting that the AKT and mTOR signaling pathways intersect to influence Treg fate. Moreover, T cells deficient in mTOR differentiate to Tregs more readily than normal control T cells (Delgoffe et al., (2009) *Immunity* 30:832-844). An obligatory role for the co-inhibitory molecules PD-1/PD-L1 in controlling adaptive Treg development by antagonizing AKT/mTOR has also been reported (Francisco et al., (2009) *J. Exp. Med.* 206:3015-3029). To determine if these pathways are also involved in BsB-mediated induction of Tregs, anti-CD3 and anti-CD28 antibodies were co-immobilized with BsB, mIgG, or PD-L1 on 96-well plates, onto which naïve T cells were seeded. Eighteen hours post-activation, the cells were stained with fluorescently-labeled antibodies against phosphorylated AKT and mTOR and analyzed by flow cytometry. Phosphorylation of both AKT and mTOR was attenuated by BsB and PD-L1 co-immobilization (FIG. 6). Without being bound to a particular theory, signaling events mediated by CTLA-4 and PD-L1 inhibitory molecules may converge at some point along the AKT/mTOR signaling pathway during T cell activation to regulate Treg differentiation.

Example 8

Exposure to BsB Sustains Foxp3+ Expression in Induced Tregs.

In vitro-induced Tregs, unlike fully committed natural Tregs, are reportedly less stable and can lose Foxp3+ expression upon extended culture in the absence of the initial inducer (e.g., TGF-β or retinoic acid) (Selvaraj and Geiger, (2007) *J. Immunol.* 178:7667-7677). In the current study, BsB-induced Tregs showed similar instability, with some cells losing Foxp3 expression following repeated culture (FIG. 7). To test whether re-stimulation by BsB could prolong Foxp3 expression, Tregs were first induced by coating 96-well plates with both anti-CD3/anti-CD28 antibodies and BsB. Purified Tregs were then subjected to an additional round of culture in the presence or absence of BsB. Re-stimulation of the purified Tregs with BsB allowed for maintenance of a large population (~93% of total Tregs) of Foxp3$^+$ Tregs (FIG. 7, bottom right panel), compared to ~40% Foxp3 expression in response to the IgG control (FIG. 7, upper right panel).

Example 9

Pharmacokinetics of BsB in Mice.

Prior to testing the therapeutic utility of BsB in animal models of autoimmune diseases, its pharmacokinetic profile was determined to help design a dosing regimen in vivo. Intraperitoneal injection of BsB into C57BL/6 mice resulted in a measurable rise in circulating levels followed by rapid clearance with an estimated plasma half-life ($t_{1/2}$) of ~12 hr (FIG. 8A). This profile was unexpected since the pharmacokinetics of Fc-containing fusion proteins or antibodies is typically more prolonged. As binding of antibodies to the neonatal Fc receptor (FcRn) is primarily responsible for their prolonged half-lives (Roopenian and Akilesh, 2007), the relative abilities of BsB and a control mouse IgG2a to bind FcRn were compared. FIG. 8B shows that the binding characteristics of both proteins to the FcRn were very similar indicating that a defect in the binding of BsB to FcRn was unlikely to be the cause of its rapid clearance from the circulation.

Another potential explanation for the rapid clearance of BsB could be due to its uptake by carbohydrate receptors on non-target cells. Examples of such receptors include the asialoglycoprotein receptor (ASGPR) on hepatocytes (Weigel, 1994) and the mannose receptor on macrophages and endothelial cells of the reticuloendothelial system (Pontow et al., 1992). Analysis of BsB using the NetNGlyc server suggested it has the potential to harbor up to 10 asparagine-linked oligosaccharide side chains per monomer (FIG. 9). A monosaccharide composition analysis indicated that BsB contained approximately 37 mannose residues, and all the predicted asparagine-linked glycosylation sites may have been used because each of these asparagine-linked oligosaccharide glycans contains the core-mannose structure with three mannose residues (a total of 30 mannose residues). In addition, a small amount of high-mannose type oligosaccharides may also exist to account for the extra mannose residues. Indeed, significant amounts of under-sialylated tri- and tetra-antennary asparagine-linked, as well as some high-mannose type oligosaccharides were identified by mass spectrometry of permethylated glycans released from the protein.

This projection is also consistent with BsB's molecular weight of 100 kDa as indicated by an SDS-PAGE analysis, as opposed to BsB's calculated weight of 80 kDa. The added presence of oligosaccharides contributed to the difference (20 kDa) in molecular weight. Moreover, BsB exhibited a ratio of sialic acids to galactose of 0.68 (FIG. 9), indicating that the glycans were incompletely sialylated. Without being bound to a particular theory, the carbohydrate-mediated clearance of BsB by the ASGPR contributed to its rapid clearance from circulation.

Example 10

A Short Course of Treatment with BsB Delayed the Onset of Autoimmune Diabetes in NOD Mice.

As the $EC_{50}$ of BsB for inducing Tregs in vitro was estimated to be about 100 nM and its circulating half-life was short ($t_{1/2}$ at ~12 h), BsB was tested in NOD mice in a late prevention paradigm. NOD mice were administered BsB over a short interval (every other day for 4 weeks) when they were between 9 and 12 weeks of age. At this age, autoreactive T cells and insulitis are already evident but the mice have yet to develop overt diabetes. As shown in FIG. 10A, NOD mice treated for 2 weeks with BsB showed a modest but statistically significantly increase (25%) in the number of Foxp3$^+$ Treg in the blood when compared to saline-treated controls. However, this increase in Tregs was transient as a difference in the number of Tregs after 4 weeks of treatment or at later times points was unable to be detected. A similar transient increase in Tregs in lymphoid organs was noted previously following treatment of NOD mice with an anti-CD3 antibody (Nishio et al., 2010). Without being bound to a particular theory, the BsB-induced Tregs may have reverted to Foxp3$^-$ T cells after cessation of treatment. They may also have been recruited by specific target tissues (e.g. pancreas) to execute their function. Regardless, this short course of treatment with BsB in a late prevention treatment paradigm appears to modestly delay the onset of disease and decrease the number of mice presenting with overt T1D (FIG. 10B).

The modest response noted may have been due to the presence of active insulitis in the 9 week-old NOD mice prior to commencement of therapy. An inflammatory milieu has been shown to favor the conversion of activating T cells to Th17 cells and suppress their conversion to Tregs. Inflammatory cytokines such as IL-6 or IL-4 have also been shown to inhibit Treg conversion and promote the loss of Foxp3$^+$ expression in Tregs (Caretto et al., 2010; Kastner et al., 2010; Koenen et al., 2008). To circumvent these challenges, NOD mice were treated starting at an earlier age (4 week-old) prior to overt induction of auto-reactive T cells and insulitis. CTLA-4Ig was also included as a positive control in this study as Bluestone and colleagues (Lenschow et al., 1995) had demonstrated a benefit using this agent in this model; mIgG2a was used as an additional negative control to saline. In contrast to the results in older mice (FIG. 10A), the number of Foxp3$^+$ Tregs in the peripheral blood of younger NOD mice treated for 2 weeks with BsB was not increased over those administered saline or mIgG (FIG. 11A). Without being bound to a particular theory, this might be because the number of auto-reactive T cells in 4 week-old NOD mice (in contrast to 9-12 week old mice used in the earlier study) was very low. The number of induced antigen-specific Tregs was likely too small to register beyond the basal levels present in the animals. A significantly lower incidence of T1D was noted in NOD mice administered BsB when compared to the saline-treated controls prior to 24 weeks of age (FIG. 11B). However, this benefit was reduced at the later time points.

Consistent with the report of NOD mice administered CTLA-4Ig (Salomon et al., 2000), the levels of Tregs in the blood (FIG. 11A) were significantly depressed presumably because of CTLA-4Ig's effects on CD28/B7 signaling (Tang et al., 2003). Treatment with CTLA-4Ig also aggravated the disease with mice exhibiting an earlier onset of disease (FIG. 11B) and higher penetrance of disease when compared to the saline- and mI$_B$G-treated controls (FIG. 11B). The reason for the discrepancy between these findings and those reported by Bluestone and colleagues (Lenschow et al., 1995) is unclear but may be due to the differences in the CTLA-4Ig used or the dosing regimen employed. In the present studies, a dose of 10 mg/kg of human CTLA-4Ig (Orencia) was used instead of 2.5 mg/kg of mouse CTLA-4Ig by Bluestone and colleagues. Moreover, BsB treatment was not extended beyond 7 weeks. Without being bound to a particular theory, the use of a higher dose of CTLA-4Ig afforded a more complete blockade of the co-stimulatory signal required for Treg homeostasis.

Example 11

A longer course of treatment with BsB significantly delayed the onset and reduced the incidence of autoimmune diabetes in NOD mice.

Potential reasons for the observed modest benefits of BsB at addressing the disease in NOD mice in the earlier studies include the deployment of a relatively short-course of treatment, the moderate potency of BsB at inducing the production of Tregs ($EC_{50}$ at >100 nM), and the short circulating half-life of BsB that may have limited its exposure. As the potency and circulating half-life of BsB are intrinsic to the molecule and therefore not amenable to facile change, a longer course of treatment was tested. To this end, NOD mice were treated with BsB for 10 weeks instead of 4 weeks starting when the mice were at 4 weeks of age. As shown in FIG. 12A, NOD mice treated for 10 weeks with BsB exhibited a significant delay in the onset of T1D. Importantly, by 35 weeks of age, only ~13% of BsB-treated NOD mice developed T1D as compared to over 70% in the saline-treated controls. Thus, extended treatment of NOD mice with BsB appeared to have protected the animals from developing autoimmune diabetes.

At the conclusion of the study (when mice were 35 week-old), the animals were sacrificed and their pancreata were collected for histopathological analysis. Adjacent serial sections were stained with H&E for a general assessment of the islets, probed with an anti-insulin antibody to detect the presence of insulin in the β-cells, and double stained with anti-CD3 and anti-Foxp3 antibodies to locate T cells and Tregs.

Due to the genetic heterogeneity of the NOD mice, a small number of the untreated animals did not develop disease at 35 weeks of age. Analysis of the islets of these non-diabetic animals (from the saline-treated cohort) showed the β-cells were intact with no obvious evidence of lymphocytic infiltration or insulitis, (FIG. 12B, panels a-c). A few Foxp3$^+$ Treg cells were present in the islets of these mice (arrows in panel c). In contrast, islets from diabetic NOD mice (from the saline-treated cohort) revealed the presence of invasive insulitis (FIG. 12B, panel d) and complete destruction of the β-cells (panel e). In addition to CD3$^+$ T cells and Foxp3$^+$ Tregs, large numbers of non-T cell lymphocytes were also evident (FIG. 12B, panel f). Similar histopathological findings were noted in the corresponding BsB-treated mice that remained disease-free at the end of the study or that developed T1D during the study. Interestingly, in ~50% of the islets of BsB-treated NOD mice that remained non-diabetic, evidence of peri-insulitis were noted (FIG. 12B, panel g); however, the β-cells were well preserved (FIG. 12B, panel h). Staining with antibodies indicated that the cells at the periphery of the islets comprise primarily CD3$^+$ T cells and Tregs. (FIG. 12B, panel i). An enlargement of a section of the image (square in FIG. 12B, panel i) clearly revealed the presence of numerous Foxp3$^+$ Tregs (arrows in FIG. 12B, panel j) that were interspersed with non-Foxp3$^+$ but CD3$^+$ T cells (arrow heads in FIG. 12B, panel j) as well as non-T cell mononucleocytes. The development of peri-insulitis has been noted in young (4-10 week-old) NOD mice (Anderson and Bluestone, 2005) and in older mice treated with other efficacious therapeutic agents that delayed or reversed new onset T1D in NOD mice (Chatenoud et al., 1994; Daniel et al., 2011; Simon et al., 2008; Vergani et al., 2010). Hence, a longer course of treatment of NOD mice with BsB protected the animals from developing invasive insulitis and overt T1D. Without being bound to a particular theory, this was mediated, at least in part, by the de novo and possibly in situ induction of islet antigen-specific Tregs.

Crosslinking CTLA-4 and TCR via MHCII using a novel bispecific fusion protein (BsB) efficiently induced the production of antigen-specific Tregs as well as the anti-inflammatory cytokines, IL-10 and TGF-β. Previous studies showed that Tregs are critical for conferring immune tolerance and that antigen-specific Tregs are more efficacious in animal models of autoimmune diseases. BsB was further evaluated in animal models of autoimmune diseases, such as T1D. Without being bound to a particular theory, it was hypothesized that if BsB promoted the induction of antigen-specific Tregs during the early phase of activation of autoreactive T cells in NOD mice it can delay the onset or halt the progression of disease by converting the autoreactive T cells that are undergoing activation to Tregs.

Despite BsB exhibiting a modest potency (due to its moderate affinity for the MHC-II and TCR) and a short circulating half-life (which limited its exposure), a short course of treatment reproducibly delayed the onset of T1D in NOD mice treated at an early age (between 4-6 weeks of age) and when they were older (between 9-12 weeks of age). However, the observed benefits were modest and unsustained. A longer course of treatment (10 weeks) of NOD mice (between 4 and 13 weeks of age) with BsB significantly delayed the onset of disease and the incidence of animals developing T1D. Without being bound to a particular theory, this benefit was imparted by the de novo generation of induced Tregs that were either produced locally (e.g. in the pancreas or pancreatic draining lymph nodes) or distally that were then recruited to the pancreas to protect the islets from destruction by autoreactive T cells and other non-T cell leukocytes. Immunohistochemical staining of sections of pancreatic tissues of 35 week-old BsB-treated mice that remained non-diabetic clearly indicated an increase in the number of Foxp3$^+$ Tregs at the periphery of the islets. Visually, they appeared to be preventing CD3$^+$ T cells and non-T cell lymphocytes from entering the islets. This phenomenon was observed in ~50% of the islets of BsB-treated NOD mice that remained non-diabetic at the end of the study but in none of the islets of diabetic animals in the control group. The islets of a few non-diabetic mice in the control group remained devoid of lymphocytic infiltrations and were insulitis-free. It is known that because of the genetic heterogeneity of NOD mice, a few animals in a cohort of this size never develop diabetes within this timeframe. In the remaining ~50% of the non-diabetic animals in the BsB-treated group, the islets were also devoid of lymphocytic infiltrations and insulitis-free. Possibilities for the disease-free status of these mice include BsB treatment and the genetic background.

Consistent with the histopathological findings, a small but statistically significant increase in the number of Foxp3$^+$ Tregs was detected in the blood of BsB-treated animals (treated from 9-12 weeks of age) when compared to untreated controls. This increase was not evident in mice that started treatment at a younger age (4 week-old). Without being bound to a particular theory, this may be because more autoreactive T cells were undergoing activation in the 9 week-old than in the 4 week-old mice. The low levels of autoreactive T cells in the 4 week-old mice might have precluded detection of induced Tregs beyond that in the existing milieu of Tregs. The increase in Tregs was also transient in nature. As a similar observation was noted in animals subjected to anti-CD3 therapy (Nishio et al., 2010), it is possible that the induced Tregs were unstable and lost expression of Foxp3. It is more conceivable that the Tregs were recruited from circulation to affected target tissues. In contrast, NOD mice treated with CTLA-4Ig exhibited a significant decrease in the number of circulating Tregs. Treatment also aggravated the disease as evidenced by an expedited onset of disease and a higher incidence of animals displaying overt disease. This is consistent with previous reports showing that the co-stimulatory pathway is involved in Treg homeostasis and that a lack of co-stimulation reduces the production of Tregs. Blocking or knocking-out CD80 or CD86 in NOD mice also results in an earlier onset of T1D (Salomon et al., 2000; Tang et al., 2003).

The appearance of peri-insulitis is typically observed in the pancreas of NOD mice between 4 and 9 weeks of age. If uncontrolled, invasive insulitis ensues leading to the complete destruction of β-cells and the development of overt diabetes between 12 and 35 weeks of age. The pancreata of non-diabetic NOD mice that had been treated for 10 weeks with BsB and analyzed at 35 weeks of age exhibited evidence of peri-insulitis that appeared to be arrested in their progression. No indication of invasive insulitis or excessive destruction of insulin-producing β-cells was noted. There are other reports of different therapeutic interventions similarly delaying or preventing disease in NOD mice (Shoda et al., 2005). The results here are most akin to those reported by Lee et al. (2010), who showed that transfer of diabetogenic $CD4^+CD25^-$ BDC2.5 T cells depleted of $CD4^+CD25^+$ Tregs into female NOD/SCID mice expedited the development of invasive insulitis when compared to mice administered total $CD4^+$ T cells containing $CD4^+CD25^+$ Tregs. Invasive insulitis was largely dominated by infiltration of dendritic cells (DC) rather than by BDC2.5 T cells per se. The authors surmised from their study that Tregs regulated the invasiveness of DCs into the islets by modulating, at least in part, the chemotaxis of DCs in response to the chemokines CCL19 and CCL21 secreted by the islets. The immunohistochemical staining patterns for $Foxp3^+$ Tregs, $CD3^+$ T cells and non-T cell leukocytes noted in the pancreatic sections of BsB-treated, non-diabetic NOD mice are consistent with their findings (FIG. 12B). Without being bound to a particular theory, Tregs produced in NOD mice in response to BsB likely acted to halt the migration of autoreactive T cells and non-T cell lymphocytes into the islets. A longer course of treatment with BsB was more effective because this generated a more robust and sustained induction of Tregs. That continuous stimulation of induced Tregs with BsB in cell cultures extended the expression of $Foxp3^+$ in Tregs is supportive of this notion (Karman et al., 2012).

Cell therapy using freshly isolated, ex vivo expanded or in vitro induced Tregs in animal models of autoimmune diseases or organ transplants have demonstrated that adoptive transfer of Tregs can restore the balance of Tregs versus effector T cells, thereby controlling the exuberant autoimmunity associated with these diseases (Allan et al., 2008; Jiang et al., 2006; Riley et al., 2009; Tang et al., 2012). However, the use of adoptive transfer as a therapeutic strategy presents several challenges to translation into the clinic. Firstly, the number of autologous Tregs that can be isolated from peripheral blood of a human subject is limiting. Hence extensive ex vivo expansion of the Tregs is often necessary, which may alter their functionality and purity. Secondly, as the isolated Tregs are polyclonal, they can exert a pan-immune suppressive function on non-target effector T cells. Thirdly, and most importantly, the plasticity of Tregs poses a significant challenge (Bluestone et al., 2009; Zhou et al., 2009a). It has been shown that adoptively transferred Tregs can lose Foxp3 expression and redifferentiate into Th17 cells (Koenen et al., 2008) or pathogenic memory T cells (Zhou et al., 2009b) which raises the risk of aggravating the autoimmunity or inflammation. Consequently, a therapeutic that induces the generation of Tregs in an antigen-specific manner in situ is more advantageous over adoptive Treg cell therapy. The results presented herein demonstrate the utility and effectiveness of such an agent (BsB) that crosslinks CTLA-4 to MHCII in the context of a mouse model of T1D. The combined demonstration of production of IL-10, TGF-β and Tregs in response to treatment with BsB as well as efficacy in the NOD mouse model of T1D has the potential to provide a novel therapeutic concept. BsB also offers additional advantages over other immune modulators in that it does not affect resting T cells or other lymphocytes. The numbers and percentages of $CD4^+$ T cells and $CD19^+$ B cells in the periphery remained the same in all our NOD studies. Without being bound to a particular theory, this approach is effective in delaying or halting disease progression. The development of BsB variants that are more potent and that harbor a more favorable pharmacokinetic profile should confirm these studies. Thus, this concept may also be applied towards the management of other immune-mediated diseases.

Results reported herein were obtained using the following methods and materials unless indicated otherwise.

Animals. Female wild-type C57BL/6 ($H-2^b$), BALB/c($H-2^d$), transgenic OT-II mice expressing the mouse α-chain and β-chain T cell receptor specific for chicken ovalbumin 323-339 ($Ova_{323-339}$) in C57BL/6 genetic background, and female non-obese diabetic (NOD/LtJ) mice were purchased from The Jackson Laboratory. Animals were maintained in a pathogen-free facility and studies were conducted in accordance with the guidelines issued by the U.S. Department of Health and Human Services (NIH Publication No 86-23) and by Genzyme's Institutional Animal Care and Use committee.

Antibodies and reagents. Functional grade or fluorescently-labeled anti-mouse CD3 (clone 145-2C11), CD25, insulin and $Foxp3^+$ antibodies were purchased from eBioscience or BD Biosciences. Murine CTLA-4-Fc and human CTLA-4Ig (Orencia) were purchased from R&D Systems, Inc. and Bristol-Myers Squibb, respectively. Mouse IgG2a isotype control was obtained from BioXCell Inc. CFSE, ultralow Ig fetal bovine serum (FBS), and other cell culture media were from Invitrogen. Chicken $OVa_{323-339}$ peptide was obtained from New England Peptide.

Construction and production of the bispecific fusion protein BsB. Construction and expression of the bispecific fusion protein (BsB) comprising the extracellular domains of CD80w88a and LAG-3 as well as the Fc of mouse IgG2a (CD80wa-LAG-3-Fc, BsB) were described previously (Karman et al., 2012).

Biacore assays and monosaccharide composition analysis. Biacore was used to compare the binding of BsB and mIgG2a to the mouse neonatal Fc receptor (FcRn). Briefly, a CM5 chip was immobilized with ~1430 RU of mouse FcRn-HPC4 using amine chemistry. Each sample was serially diluted 1:2 to final concentrations of between 200 and 6.25 nM in PBSP (PBS with 0.005% Surfactant P-20), pH 6.0 and injected for 3 min in duplicate, followed by 3 min wash with dissociation buffer. The surface was regenerated with 10mM sodium borate and 1M NaCl, pH 8.5. The carbohydrate monosaccharide composition of BsB was analyzed according to the protocol described by Zhou et al. (Zhou et al., 2011).

Isolation of naïve T cells. Naive T cells from the spleens and lymph nodes of 8-12 week old female BALB/c or OT-II mice were purified by magnetic separation followed by fluorescence-activated cell sorting. Cells were first negatively selected by magnetic cell separation (Miltenyi Biotech) and then sorted as $CD4^+CD25^- CD62L^{hi}CD44^{low}$ cells to a purity of greater than 98%.

Antigen-specific Treg induction assay. Assays in an allogenic MLR setting was performed as previously reported (Karman et al., 2012). For antigen-specific T cell activation, $10^5$ naïve OT-II T cells were mixed in round-bottom 96-well plates with $10^5$ irradiated syngeneic APCs in the presence of Ova$_{323-329}$ at 0.5 µg/ml and 1 µg/ml soluble anti-CD28 (clone 37.51, eBioscience). The test constructs, mouse IgG2a, or mouse CTLA-4Ig were added to the cultured cells at a saturating concentration of 100 µg/ml. The cells were cultured for 5 days to induce production of Tregs and analyzed by flow cytometry. Media were collected for analysis of IL-2, IL-10 and TGF-β using ELISA kits per the manufacturer's instructions. To assess T cell proliferation, purified naïve OT-II T cells were labeled with 5 µM CFSE for 5 min at 37° C. They were then washed to remove unbound CFSE and used in Treg induction assays as described above. Cells were cultured for 5 days to allow them to divide before being analyzed by flow cytometry. To detect Foxp3$^+$ in T cells, cells were stained for surface markers as described above followed by permeabilizing with Fix/Perm buffer (eBioscience) and staining with PE-Cy7 conjugated anti-Foxp3 antibody (clone FJK-16s, eBioscience).

Pharmacokinetics measurements of BsB in mice. The pharmacokinetics of BsB was determined in 8 week-old C57BL/6 mice. 20 mg/kg of BsB was administered into mice by intraperitoneal injection. Blood was collected by saphenous vein bleeding at 1 hr, 5 hr, 24 hr, 48 hr, and 72 hr after administration. The levels of BsB at each time point were measured using an ELISA assay. Briefly, 100 µl (1 µg/ml) of an anti-mouse CD80 antibody in PBS were coated onto 96-well plates and incubated overnight at 4° C. Plates were blocked with 5% fetal bovine serum for 1 h, after which they were washed 4 times with PBS. 100 µl of blood samples at various dilutions were then added into the wells. The plates were incubated for 2 hr with gentle shaking at room temperature and washed 4 times with PBS. Biotinylated anti-mouse LAG-3 antibody (1 µg/ml) was added and incubated for 2 hr. The plates were washed 4 times with PBS after which streptavidine-HRP was added. After 30 min, the plates were washed 6 times with PBS and developed for colorimetric measuring. Purified BsB diluted in assay diluent at various concentrations were used as standards.

Treatment of NOD mice with BsB. In the short course treatment, 4 week-old female NOD mice were treated with saline, 20 mg/kg BsB, 20 mg/kg mouse IgG2a, or 10 mg/kg human CTLA-4Ig (Orencia) three times a week by intraperitoneal injection over a period of 2.5 weeks. For the late prevention model, 9-12 week-old NOD mice were treated with saline or 20 mg/kg BsB as above for 4 weeks. For longer course treatment, NOD mice were treated with BsB or saline as above for 10 weeks from age of 4 weeks to 13 weeks. Non-fasting blood glucose levels were monitored weekly starting at 8 weeks of age. Mice were deemed diabetic when their glucose readings were greater than 300 mg/dL for three consecutive readings. Foxp3$^+$ Tregs in peripheral blood was examined after two weeks of treatment by flow cytometry. Briefly, 50 µl of whole blood was blocked with unlabeled anti-FcγRIIb and FcgRIII (clone 93, eBioscience) for 20 min. Cells were subsequently stained with fluorescently-labeled anti-CD4 antibody for 30 min and then washed. Red blood cells were lysed using FACS Lysing solution (BD Biosciences) for 5 min. After washing, cells were fixed, permeabilized and stained with a FITC-labeled anti-Foxp3 antibody for 30 min as described above. Pancreata were dissected in half with one half fixed in neutral buffer formalin and the other placed into OCT compound and then frozen on dry ice.

Statistical analysis. Cumulative incidences of NOD mice presenting with T1D and hyperglycemia following treatment with BsB or controls were compared using the log-rank (Cox-Mantel) test in Prism 5 (Graphpad, city and state). A value of $p<0.05$ was considered statistically significant.

Histopathological analysis. Neutral buffer formalin-fixed pancreata was stained for CD3, Foxp3$^+$ cells using an automated processer. Tissue sections were dewaxed using xylene-ethanol, the antigens retrieved by incubating for 25 min in citrate buffer and then blocked with serum. Slides were incubated with an anti-CD3 antibody for 45 min, followed by a goat anti-rabbit horse radish peroxidase polymer for 20 min. Chromogen visualization of CD3 was obtained by incubating with 3,3'-diaminobenzidine tetrahydrochloride for 2-4 min. To detect Foxp3$^+$, sections were re-blocked with serum, followed by exposure to an anti-Foxp3 antibody for 45 min.

Slides were then incubated with a rabbit anti-rat IgG antibody for 30 min, followed by a goat anti-rabbit alkaline phosphatase polymer. Chromogen visualization was achieved using Fast Red for 10 min. Tissue sections were counterstained using hematoxylin for 2 min and washed 3 times with 0.05% Tween-20/Tris buffered saline between steps. Adjacent serial sections were stained using an anti-insulin antibody as described above. Pictures were taken using a Nikon Eclipse E800 fluorescent microscope with an attached digital camera from Diagnostic Inc. and images acquired using the Spot Advanced software.

```
Sequences
Legend
CD80w88a = CTLA-4 ligand

IgG2a = IgG2 Fc region

G9 = Gly 9

Lag-3 = MHC ligand

H6 = His 6

SEQ ID NO. 1:
CTLA-4 BsB (Gene1) = mouse CD80w88a(aa1-235)-
IgG2a(aa241-474)-G9-Lag-3(aa25-260)-H6
Nucleotide sequence of mouse surrogate construct
(Gene1):
ATGGCTTGCAATTGTCAGTTGATGCAGGATACACCACTCCTCAAGTTTCC

ATGTCCAAGGCTCATTCTTCTCTTTGTGCTGCTGATTCGTCTTTCACAAG

TGTCTTCAGATGTTGATGAACAACTGTCCAAGTCAGTGAAAGATAAGGTA
```

-continued

```
TTGCTGCCTTGCCGTTACAACTCTCCTCATGAAGATGAGTCTGAAGACCG
AATCTACTGGCAAAAACATGACAAAGTGGTGCTGTCTGTCATTGCTGGGA
AACTAAAAGTGGCGCCCGAGTATAAGAACCGGACTTTATATGACAACACT
ACCTACTCTCTTATCATCCTGGGCCTGGTCCTTTCAGACCGGGGCACATA
CAGCTGTGTCGTFCAAAAGAAGGAAAGAGGAACGTATGAAGTTAAACACT
TGGCTTTAGTAAAGTTGTCCATCAAAGCTGACTTCTCTACCCCCAACATA
ACTGAGTCTGGAAACCCATCTGCAGACACTAAAAGGATTACCTGCTTTGC
TFCCGGGGGITTCCCAAAGCCTCGCTTCTCTTGGTTGGAAAATGGAAGAG
AATTACCTGGCATCAATACGACAATTTCCCAGGATCCTGAATCTGAATTG
TACACCATTAGTAGCCAACTAGATTTCAATACGACTCGCAACCACACCAT
TAAGTGTCTCATFAAATATGGAGATGCTCACGTGTCAGAGGACTTCACCT
GGGAGCCCAGAGGGCCCACAATCAAGCCCTGTCCTCCATGCAAATGCCCA
GCACCTAACCTCTTGGGTGGACCATCCGTCTTCATCTTCCCTCCAAAGAT
CAAGGATGTACTCATGATCTCCCTGAGCCCCATGGTCACATGTGTGGTGG
TGGATGTGAGCGAGGATGACCCAGATGTCCAGATCAGCTGGTTCGTGAAC
AACGTGGAAGTACTCACAGCTCAGACACAAACCCATAGAGAGGATTACAA
CAGTACTCTCCGGGTGGTCAGTGCCCTCCCCATCCAGCACCAGGACTGGA
TGAGTGGCAAGGAGTTCAAATGCAAGGTCAACAACAAAGCCCTCCCAGCG
CCCATCGAGAGAACCATCTCAAAACCCAAAGGGTCAGTAAGAGCTCCACA
GGTATATGTCTTGCCTCCACCAGAAGAAGAGATGACTAAGAAACAGGTCA
CTCTGACCTGCATGGTCACAGACTTCATGCCTGAAGACATTTACGTGGAG
TGGACCAACAACGGGAAAACAGAGCTAAACTACAAGAACACTGAACCAGT
CCTGGACTCTGATGGTTCTTACTTCATGTACAGCAAGCTGAGAGTGGAAA
AGAAGAACTGGGTGGAAAGAAATAGCTACTCCTGCTCAGTGGTCCACGAG
GGTCTGCACAATCACCACACGACTAAGAGCTTCTCCCGGACTCCGGGTAA
AGGCGGTGGCGGCGGAGGCGGTGGCGGTGGGCCTGGGAAAGAGCTCCCCG
TGGTGTGGGCCCAGGAGGGAGCTCCCGTCCATCTTCCCTGCAGCCTCAAA
TCCCCCAACCTGGATCCTAACTTTCTACGAAGAGGAGGGGTTATCTGGCA
ACATCAACCAGACAGTGGCCAACCCACTCCCATCCCGGCCCTTGACCTTC
ACCAGGGGATGCCCTCGCCTAGACAACCCGCACCCGGTCGCTACACGGTG
CTGAGCGTGGCTCCAGGAGGCCTGCGCAGCGGGAGGCAGCCCCTGCATCC
CCACGTGCAGCTGGAGGAGCGCGGCCTCCAGCGCGGGGACTTCTCTCTGT
GGTTGCGCCCAGCTCTGCGCACCGATGCGGGCGAGTACCACGCCACCGTG
CGCCTCCCGAACCGCGCCCTCTCCTGCAGTCTCCGCCTGCGCGTCGGCCA
GGCCTCGATGATTGCTAGTCCCTCAGGAGTCCTCAAGCTGTCTGATTGGG
TCCTTTTGAACTGCTCCTTCAGCCGTCCTGACCGCCCAGTCTCTGTGCAC
TGGTTCCAGGGCCAGAACCGAGTGCCTGTCTACAACTCACCGCGTCATTT
TTTAGCTGAAACTTTCCTGTTACTGCCCCAAGTCAGCCCCCTGGACTCTG
GGACCTGGGGCTGTGTCCTCACCTACAGAGATGGCTTCAATGTCTCCATC
```

ACGTACAACCTCAAGGTTCTGGGTCTGGAGCCCGTAGCCCACCATCACCA

TCATCACTGA

SEQ ID NO. 2:
CTLA-4 BsB (Gene1) = mouse CD80w88a(aa1-235)-
IgG2a(aa241-474)-G9-Lag-3(aa25-260)-H6
Translated protein sequence of mouse surrogate
construct (Gene1):
MACNCQLMQDTPLLKFPCPRLILLFVLLIRLSQVSSDVDEQLSKSVKDKV

LLPCRYNSPHEDESEDRIYWQKHDKVVLSVIAGKLKVAPEYKNRTLYDNT

TYSLIILGLVLSDRGTYSCVVQKKERGTYEVKHLALVKLSIKADFSTPNI

TESGNPSADTKRITCFASGGFPKPRFSWLENGRELPGINTTISQDPESEL

YTISSQLDFNTTRNHTIKCLIKYGDAHVSEDFTWEPRGPTIKPCPPCKCP

APNLLGGPSVFIFPPKIKDVLMISLSPMVTCVVVDVSEDDPDVQISWFVN

NVEVLTAQTQTHREDYNSTLRVVSALPIQHQDWMSGKEFKCKVNNKALPA

PIERTISKPKGSVRAPQVYVLPPPEEEMTKKQVTLTCMVTDFMPEDIYVE

WTNNGKTELNYKNTEPVLDSDGSYFMYSKLRVEKKNWVERNSYSCSVVHE

GLHNHHTTKSFSRTPGKGGGGGGGGGGPGKELPVVWAQEGAPVHLPCSLK

SPNLDPNFLRRGGVIWQHQPDSGQPTPIPALDLHQGMPSPRQPAPGRYTV

LSVAPGGLRSGRQPLHPHVQLEERGLQRGDFSLWLRPALRTDAGEYHATV

RLPNRALSCSLRLRVGQASMIASPSGVLKLSDWVLLNCSFSRPDRPVSVH

WFQGQNRVPVYNSPRHFLAETFLLLPQVSPLDSGTWGCVLTYRDGFNVSI

TYNLKVLGLEPVAHHHHHH

SEQ ID NO. 3:
CTLA-4 BsB (Gene2) = mouse CD80w88a(aa1-235)-
G9-Lag-3(aa25-260)-IgG2a(aa241-474)
Nucleotide sequence of mouse surrogate construct
(Gene 2):
ATGGCTTGCAATTGTCAGTTGATGCAGGATACACCACTCCTCAAGTTTCC

ATGTCCAAGGCTCATTCTTCTCTTTGTGCTGCTGATTCGTCTTTCACAAG

TGTCTTCAGATGTTGATGAACAACTGTCCAAGTCAGTGAAAGATAAGGTA

TTGCTGCCTTGCCGTTACAACTCTCCTCATGAAGATGAGTCTGAAGACCG

AATCTACTGGCAAAAACATGACAAAGTGGTGCTGTCTGTCATTGCTGGGA

AACTAAAAGTGGCGCCCGAGTATAAGAACCGGACTTTATATGACAACACT

ACCTACTCTCTTATCATCCTGGGCCTGGTCCTTTCAGACCGGGGCACATA

CAGCTGTGTCGTTCAAAAGAAGGAAAGAGGAACGTATGAAGTTAAACACT

TGGCTTTAGTAAAGTTGTCCATCAAAGCTGACTTCTCTACCCCCAACATA

ACTGAGTCTGGAAACCCATCTGCAGACACTAAAAGGATTACCTGCTTTGC

TTCCGGGGGTTTCCCAAAGCCTCGCTTCTCTTGGTTGGAAAATGGAAGAG

AATTACCTGGCATCAATACGACAATTTCCCAGGATCCTGAATCTGAATTG

TACACCATTAGTAGCCAACTAGATTTCAATACGACTCGCAACCACACCAT

TAAGTGTCTCATTAAATATGGAGATGCTCACGTGTCAGAGGACTTCACCT

GGGCGGTGGCGGCGGAGGCGGTGGCGGTGGGCCTGGGAAAGAGCTCCCC

GTGGTGTGGGCCCAGGAGGGAGCTCCCGTCCATCTTCCCTGCAGCCTCAA

ATCCCCCAACCTGGATCCTAACTTTCTACGAAGAGGAGGGGTTATCTGGC

AACATCAACCAGACAGTGGCCAACCCACTCCCATCCCGGCCCTTGACCTT

CACCAGGGGATGCCCTCGCCTAGACAACCCGCACCCGGTCGCTACACGGT

-continued
```
GCTGAGCGTGGCTCCAGGAGGCCTGCGCAGCGGGAGGCAGCCCCTGCATC
CCCACGTGCAGCTGGAGGAGCGCGGCCTCCAGCGCGGGGACTTCTCTCTG
TGGTTGCGCCCAGCTCTGCGCACCGATGCGGGCGAGTACCACGCCACCGT
GCGCCTCCCGAACCGCGCCCTCTCCTGCAGTCTCCGCCTGCGCGTCGGCC
AGGCCTCGATGATTGCTAGTCCCTCAGGAGTCCTCAAGCTGTCTGATTGG
GTCCTTTTGAACTGCTCCTTCAGCCGTCCTGACCGCCCAGTCTCTGTGCA
CTGGTTCCAGGGCCAGAACCGAGTGCCTGTCTACAACTCACCGCGTCATT
TTTTAGCTGAAACTTTCCTGTTACTGCCCCAAGTCAGCCCCCTGGACTCT
GGGACCTGGGCTGTGTCCTCACCTACAGAGATGGCTTCAATGTCTCCAT
CACGTACAACCTCAAGGTTCTGGGTCTGGAGCCCGTAGCCCCAGAGGGC
CCACAATCAAGCCCTGTCCTCCATGCAAATGCCCAGCACCTAACCTCTTG
GGTGGACCATCCGTCTTCATCTTCCCTCCAAAGATCAAGGATGTACTCAT
GATCTCCCTGAGCCCCATGGTCACATGTGTGGTGGTGGATGTGAGCGAGG
ATGACCCAGATGTCCAGATCAGCTGGTTCGTGAACAACGTGGAAGTACTC
ACAGCTCAGACACAAACCCATAGAGAGGATTACAACAGTACTCTCCGGGT
GGTCAGTGCCCTCCCCATCCAGCACCAGGACTGGATGAGTGGCAAGGAGT
TCAAATGCAAGGTCAACAACAAAGCCCTCCCAGCGCCCATCGAGAGAACC
ATCTCAAAACCCAAAGGGTCAGTAAGAGCTCCACAGGTATATGTCTTGCC
TCCACCAGAAGAAGAGATGACTAAGAAACAGGTCACTCTGACCTGCATGG
TCACAGACTTCATGCCTGAAGACATTTACGTGGAGTGGACCAACAACGGG
AAAACAGAGCTAAACTACAAGAACACTGAACCAGTCCTGGACTCTGATGG
TTCTTACTTCATGTACAGCAAGCTGAGAGTGGAAAAGAAGAACTGGGTGG
AAAGAAATAGCTACTCCTGCTCAGTGGTCCACGAGGGTCTGCACAATCAC
CACACGACTAAGAGCTTCTCCCGGACTCCGGGTAAATGA
SEQ ID NO. 4:
CTLA-4 BsB (Gene2) = mouse CD80w88a(aa1-235)-
G9-Lag-3(aa25-260)-IgG2a(aa241-474)
Translated protein sequence of mouse surrogate
construct (Gene 2):
MACNCQLMQDTPLLKFPCPRLILLFVLLIRLSQVSSDVDEQLSKSVKDKV
LLPCRYNSPHEDESEDRIYVVQKHDKVVLSVIAGKLKVAPEYKNRTLYDN
TTYSLIILGLVLSDRGTYSCVVQKKERGTYEVKHLALVKLSIKADFSTPN
ITESGNPSADTKRITCFASGGFPKPRFSWLENGRELPGINTTISQDPESE
LYTISSQLDFNTTRNHTIKCLIKYGDAHVSEDFTWGGGGGGGGGPGKEL
PVVWAQEGAPVHLPCSLKSPNLDPNFLRRGGVIWQHQPDSGQPTPIPALD
LHQGMPSPRQPAPGRYTVLSVAPGGLRSGRQPLHPHVQLEERGLQRGDFS
LWLRPALRTDAGEYHATVRLPNRALSCSLRLRVGQASMIASPSGVLKLSD
WVLLNCSFSRPDRPVSVHWFQGQNRVPVYNSPRHFLAETFLLLPQVSPLD
SGTWGCVLTYRDGFNVSITYNLKVLGLEPVAPRGPTIKPCPPCKCPAPNL
LGGPSVFIFPPKIKDVLMISLSPMVTCVVVDVSEDDPDVQISWFVNNVEV
LTAQTQTHREDYNSTLRVVSALPIQHQDWMSGKEFKCKVNNKALPAPIER
TISKPKGSVRAPQVYVLPPPEEEMTKKQVTLTCMVTDFMPEDIYVEWTNN
GKTELNYKNTEPVLDSDGSYFMYSKLRVEKKNWVERNSYSCSVVHEGLHN
HHTTKSFSRTPGK
SEQ ID NO. 5:
CTLA-4 BsB human construct wildtype nucleotide
sequence = (human CD80(aa1-234)-G9-Lag-3(aa27-
262-IgG1a(aa240-471)
ATGGGCCACACACGGAGGCAGGGAACATCACCATCCAAGTGTCCATACCT
CAATTTCTTTCAGCTCTTGGTGCTGGCTGGTCTTTCTCACTTCTGTTCAG
GTGTTATCCACGTGACCAAGGAAGTGAAAGAAGTGGCAACGCTGTCCTGT
GGTCACAATGTTTCTGTTGAAGAGCTGGCACAAACTCGCATCTACTGGCA
AAAGGAGAAGAAAATGGTGCTGACTATGATGTCTGGGGACATGAATATAT
GGCCCGAGTACAAGAACCGGACCATCTTTGATATCACTAATAACCTCTCC
ATTGTGATCCTGGCTCTGCGCCCATCTGACGAGGGCACATACGAGTGTGT
TGTTCTGAAGTATGAAAAAGACGCTTTCAAGCGGGAACACCTGGCTGAAG
TGACGTTATCAGTCAAAGCTGACTTCCCTACACCTAGTATATCTGACTTT
GAAATTCCAACTTCTAATATTAGAAGGATAATTTGCTCAACCTCTGGAGG
TTTTCCAGAGCCTCACCTCTCCTGGTTGGAAAATGGAGAAGAATTAAATG
CCATCAACACAACAGTTTCCCAAGATCCTGAAACTGAGCTCTATGCTGTT
AGCAGCAAACTGGATTTCAATATGACAACCAACCACAGCTTCATGTGTCT
CATCAAGTATGGACATTTAAGAGTGAATCAGACCTTCAACTGGAATACAA
CCGGCGGTGGCGGCGGAGGCGGTGGCGGTTCCGGAGCTGAGGTCCCGGTG
GTGTGGGCCCAGGAGGGGCTCCTGCCCAGCTCCCCTGCAGCCCCACAAT
CCCCCTCCAGGATCTCAGCCTTCTGCGAAGAGCAGGGGTCACTTGGCAGC
ATCAGCCAGACAGTGGCCCGCCCGCTGCCGCCCCCGGCCATCCCCTGGCC
CCCGGCCCTCACCCGGCGGCGCCCTCCTCCTGGGGCCCAGGCCCCGCCG
CTACACGGTGCTGAGCGTGGGTCCCGGAGGCCTGCGCAGCGGGAGGCTGC
CCCTGCAGCCCCGCGTCCAGCTGGATGAGCGCGGCCGGCAGCGCGGGGAC
TTCTCGCTATGGCTGCGCCCAGCCCGGCGCGCGGACGCCGGCGAGTACCG
CGCCGCGGTGCACCTCAGGGACCGCGCCCTCTCCTGCCGCCTCCGTCTGC
GCCTGGGCCAGGCCTCGATGACTGCCAGCCCCCCAGGATCTCTCAGAGCC
TCCGACTGGGTCATTTTGAACTGCTCCTTCAGCCGCCCTGACCGCCCAGC
CTCTGTGCATTGGTTTCGGAACCGGGGCCAGGGCCGAGTCCCTGTCCGGG
AGTCCCCCCATCACCACTTAGCGGAAAGCTTCCTCTTCCTGCCCCAAGTC
AGCCCCATGGACTCTGGGCCTGGGGCTGCATCCTCACCTACAGAGATGG
CTTCAACGTCTCCATCATGTATAACCTCACTGTTCTGGGTCTGCTGGTGC
CCCGGGGCTCCGAGCCCAAATCTTGTGACAAAACTCACACATGCCCACCG
TGCCCAGCACCTGAACTCCTGGGGGGACCGTCAGTCTTCCTCTTCCCCCC
AAAACCCAAGGACACCCTCATGATCTCCCGGACCCCTGAGGTCACATGCG
TGGTGGTGGACGTGAGCCACGAAGACCCTGAGGTCAAGTTCAACTGGTAC
GTGGACGGCGTGGAGGTGCATAATGCCAAGACAAAGCCGCGGGAGGAGCA
GTACAACAGCACGTACCGTGTGGTCAGCGTCCTCACCGTCCTGCACCAGG
ACTGGCTGAATGGCAAGGAGTACAAGTGCAAGGTCTCCAACAAAGCCCTC
CCAGCCCCCATCGAGAAAACCATCTCCAAAGCCAAAGGGCAGCCCCGAGA
```

```
ACCACAGGTGTACACCCTGCCCCCATCTCGGGATGAGCTGACCAAGAACC

AGGTCAGCCTGACCTGCCTGGTCAAAGGCTTCTATCCCAGCGACATCGCC

GTGGAGTGGGAGAGCAATGGGCAGCCGGAGAACAACTACAAGACCACGCC

TCCCGTGCTGGACTCCGACGGCTCCTTCTTCCTATACAGCAAGCTCACCG

TGGACAAGAGCAGGTGGCAGCAGGGGAACGTCTTCTCATGCTCCGTGATG

CATGAGGCTCTGCACAACCACTACACGCAGAAGAGCCTCTCCCTGTCTCC

GGGTAAATGA
```
SEQ ID NO. 6:
CTLA-4 BsB human construct wildtype translated
protein sequence = (human CD80(aa1-234)-G9-Lag-
3(aa27-262)-IgG1a(aa240-471)
```
MGHTRRQGTSPSKCPYLNFFQLLVLAGLSHFCSGVIHVTKEVKEVATLSC

GHNVSVEELAQTRIYWQKEKKMVLTMMSGDMNIWPEYKNRTIFDITNNLS

IVILALRPSDEGTYECVVLKYEKDAFKREHLAEVTLSVKADFPTPSISDF

EIPTSNIRRIICSTSGGFPEPHLSWLENGEELNAINTTVSQDPETELYAV

SSKLDFNMTTNHSFMCLIKYGHLRVNQTFNWNTTGGGGGGGGSGAEVPW

WAQEGAPAQLPCSPTIPLQDLSLLRRAGVTWQHQPDSGPPAAAPGHPLAP

GPHPAAPSSWGPRPRRYTVLSVGPGGLRSGRLPLQPRVQLDERGRQRGDF

SLWLRPARRADAGEYRAAVHLRDRALSCRLRLRLGQASMTASPPGSLRAS

DVVVILNCSFSRPDRPASVHWFRNRGQGRVPVRESPHHHLAESFLFLPQV

SPMDSGPWGCILTYRDGFNVSIMYNLTVLGLLVPRGSEPKSCDKTHTCPP

CPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKAL

PAPIEKTISKAKGQPREPQVYTLPPSRDELTKNQVSLTCLVKGFYPSDIA

VEWESNGQPENNYKTTPPVLDSDGSFFLYSKLTVDKSRWQQGNVFSCSVM

HEALHNHYTQKSLSLSPGK
```
SEQ ID NO. 7:
CTLA-4 BsB human construct variant nucleotide
sequence 1 = (human CD80W84A/S190A(aa1-234)-G9-
Lag-3R316/75E(aa27-262-IgG1aN596/297Q(aa240-471)
```
ATGGGCCACACACGGAGGCAGGGAACATCACCATCCAAGTGTCCATACCT

CAATTTCTTTCAGCTCTTGGTGCTGGCTGGTCTTTCTCACTTCTGTTCAG

GTGTTATCCACGTGACCAAGGAAGTGAAAGAAGTGGCAACGCTGTCCTGT

GGTCACAATGTTTCTGTTGAAGAGCTGGCACAAACTCGCATCTACTGGCA

AAAGGAGAAGAAAATGGTGCTGACTATGATGTCTGGGGACATGAATATAG

CCCCCGAGTACAAGAACCGGACCATCTTTGATATCACTAATAACCTCTCC

ATTGTGATCCTGGCTCTGCGCCCATCTGACGAGGGCACATACGAGTGTGT

TGTTCTGAAGTATGAAAAAGACGCTTTCAAGCGGGAACACCTGGCTGAAG

TGACGTTATCAGTCAAAGCTGACTTCCCTACACCTAGTATATCTGACTTT

GAAATTCCAACTTCTAATATTAGAAGGATAATTTGCTCAACCTCTGGAGG

TTTTCCAGAGCCTCACCTCTCCTGGTTGGAAAATGGAGAAGAATTAAATG

CCATCAACACAACAGTTGCCCAAGATCCTGAAACTGAGCTCTATGCTGTT

AGCAGCAAACTGGATTTCAATATGACAACCAACCACAGCTTCATGTGTCT

CATCAAGTATGGACATTTAAGAGTGAATCAGACCTTCAACTGGAATACAA
```

```
CCGGCGGTGGCGGCGGAGGCGGTGGCGGTTCCGGAGCTGAGGTCCCGGTG

GTGTGGGCCCAGGAGGGGGCTCCTGCCCAGCTCCCCTGCAGCCCCACAAT

CCCCCTCCAGGATCTCAGCCTTCTGCGAAGAGCAGGGGTCACTTGGCAGC

ATCAGCCAGACAGTGGCCCGCCCGCTGCCGCCCCCGGCCATCCCCTGGCC

CCCGGCCCTCACCCGGCGGCGCCCTCCTCCTGGGGGCCCAGGCCCGAGCG

CTACACGGTGCTGAGCGTGGGTCCCGGAGGCCTGCGCAGCGGGAGGCTGC

CCCTGCAGCCCCGCGTCCAGCTGGATGAGCGCGGCCGGCAGCGCGGGGAC

TTCTCGCTATGGCTGCGCCCAGCCCGGCGCGCGGACGCCGGCGAGTACCG

CGCCGCGGTGCACCTCAGGGACCGCGCCCTCTCCTGCCGCCTCCGTCTGC

GCCTGGGCCAGGCCTCGATGACTGCCAGCCCCCCAGGATCTCTCAGAGCC

TCCGACTGGGTCATTTTGAACTGCTCCTTCAGCCGCCCTGACCGCCCAGC

CTCTGTGCATTGGTTTCGGAACCGGGGCCAGGGCCGAGTCCCTGTCCGGG

AGTCCCCCCATCACCACTTAGCGGAAAGCTTCCTCTTCCTGCCCCAAGTC

AGCCCCATGGACTCTGGGCCCTGGGGCTGCATCCTCACCTACAGAGATGG

CTTCAACGTCTCCATCATGTATAACCTCACTGTTCTGGGTCTGCTGGTGC

CCCGGGGCTCCGAGCCCAAATCTTGTGACAAAACTCACACAAGCCCACCG

AGCCCAGCACCTGAACTCCTGGGGGGATCCTCAGTCTTCCTCTTCCCCCC

AAAACCCAAGGACACCCTCATGATCTCCCGGACCCCTGAGGTCACATGCG

TGGTGGTGGACGTGAGCCACGAAGACCCTGAGGTCAAGTTCAACTGGTAC

GTGGACGGCGTGGAGGTGCATAATGCCAAGACAAAGCCGCGGGAGGAGCA

GTACCAGAGCACGTACCGTGTGGTCAGCGTCCTCACCGTCCTGCACCAGG

ACTGGCTGAATGGCAAGGAGTACAAGTGCAAGGTCTCCAACAAAGCCCTC

CCAGCCCCCATCGAGAAAACCATCTCCAAAGCCAAAGGGCAGCCCCGAGA

ACCACAGGTGTACACCCTGCCCCCATCTCGGGATGAGCTGACCAAGAACC

AGGTCAGCCTGACCTGCCTGGTCAAAGGCTTCTATCCCAGCGACATCGCC

GTGGAGTGGGAGAGCAATGGGCAGCCGGAGAACAACTACAAGACCACGCC

TCCCGTGCTGGACTCCGACGGCTCCTTCTTCCTATACAGCAAGCTCACCG

TGGACAAGAGCAGGTGGCAGCAGGGGAACGTCTTCTCATGCTCCGTGATG

CATGAGGCTCTGCACAACCACTACACGCAGAAGAGCCTCTCCCTGTCTCC

GGGTAAATGA
```
SEQ ID NO. 8:
CTLA-4 BsB human construct variant translated
protein sequence 1 = (human CD80W84A/S190A(aa1-
234)-G9-Lag-3R316/75E(aa27-262-IgG1aN596/297Q
(aa240-471)
```
MGHTRRQGTSPSKCPYLNFFQLLVLAGLSHFCSGVIHVTKEVKEVATLSC

GHNVSVEELAQTRIYWQKEKKMVLTMMSGDMNIAPEYKNRTIFDITNNLS

IVILALRPSDEGTYECVVLKYEKDAFKREHLAEVTLSVKADFPTPSISDF

EIPTSNIRRIICSTSGGFPEPHLSWLENGEELNAINTTVAQDPETELYAV

SSKLDFNMTTNHSFMCLIKYGHLRVNQTFNWNTTGGGGGGGGSGAEVPV

VWAQEGAPAQLPCSPTIPLQDLSLLRRAGVTWQHQPDSGPPAAAPGHPLA

PGPHPAAPSSWGPRPRRYTVLSVGPGGLRSGRLPLQPRVQLDERGRQRGD

FSLWLRPARRADAGEYRAAVHLRDRALSCRLRLRLGQASMTASPPGSLRA
```

-continued

SDWVILNCSFSRPDRPASVHWFRNRGQGRVPVRESPHHHLAESFLFLPQV

SPMDSGPWGCILTYRDGFNVSIMYNLTVLGLLVPRGSEPKSCDKTHTSPP

SPAPELLGGSSVFLFPPKPKDTLMISRTPEVTCVVVDVSHEDPEVKFNWY

VDGVEVHNAKTKPREEQYQSTYRVVSVLTVLHQDWLNGKEYKCKVSNKAL

PAPIEKTISKAKGQPREPQVYTLPPSRDELTKNQVSLTCLVKGFYPSDIA

VEWESNGQPENNYKTTPPVLDSDGSFFLYSKLTVDKSRWQQGNVFSCSVM

HEALHNHYTQKSLSLSPGK

SEQ ID NO. 9:
CTLA-4 BsB human construct variant nucleotide
sequence 2 = (human CD80W84A/S190AS201A(aa1-
234)-G9-Lag-3R316/75E(aa27-262-IgG1aN596/
297Q(aa240-471)
ATGGGCCACACACGGAGGCAGGGAACATCACCATCCAAGTGTCCATACCT

CAATTTCTTTCAGCTCTTGGTGCTGGCTGGTCTTTCTCACTTCTGTTCAG

GTGTTATCCACGTGACCAAGGAAGTGAAAGAAGTGGCAACGCTGTCCTGT

GGTCACAATGTTTCTGTTGAAGAGCTGGCACAAACTCGCATCTACTGGCA

AAAGGAGAAGAAAATGGTGCTGACTATGATGTCTGGGGACATGAATATAG

CCCCCGAGTACAAGAACCGGACCATCTTTGATATCACTAATAACCTCTCC

ATTGTGATCCTGGCTCTGCGCCCATCTGACGAGGGCACATACGAGTGTGT

TGTTCTGAAGTATGAAAAAGACGCTTTCAAGCGGGAACACCTGGCTGAAG

TGACGTTATCAGTCAAAGCTGACTTCCCTACACCTAGTATATCTGACTTT

GAAATTCCAACTTCTAATATTAGAAGGATAATTTGCTCAACCTCTGGAGG

TTTTCCAGAGCCTCACCTCTCCTGGTTGGAAAATGGAGAAGAATTAAATG

CCATCAACACAACAGTTGCCCAAGATCCTGAAACTGAGCTCTATGCTGTT

GCCAGCAAACTGGATTTCAATATGACAACCAACCACAGCTTCATGTGTCT

CATCAAGTATGGACATTTAAGAGTGAATCAGACCTTCAACTGGAATACAA

CCGGCGGTGGCGGCGGAGGCGGTGGCGGTTCCGGAGCTGAGGTCCCGGTG

GTGTGGGCCCAGGAGGGGGCTCCTGCCCAGCTCCCCTGCAGCCCCACAAT

CCCCCTCCAGGATCTCAGCCTTCTGCGAAGAGCAGGGGTCACTTGGCAGC

ATCAGCCAGACAGTGGCCCGCCCGCTGCCGCCCCGGCCATCCCCTGGCC

CCCGGCCCTCACCCGGCGGCGCCCTCCTCCTGGGGGCCCAGGCCCGAGCG

CTACACGGTGCTGAGCGTGGGTCCCGGAGGCCTGCGCAGCGGGAGGCTGC

CCCTGCAGCCCCGCGTCCAGCTGGATGAGCGCGGCCGGCAGCGCGGGGAC

TTCTCGCTATGGCTGCGCCCAGCCCGGCGCGCGGACGCCGGCGAGTACCG

CGCCGCGGTGCACCTCAGGGACCGCGCCCTCTCCTGCCGCCTCCGTCTGC

GCCTGGGCCAGGCCTCGATGACTGCCAGCCCCCCAGGATCTCTCAGAGCC

TCCGACTGGGTCATTTTGAACTGCTCCTTCAGCCGCCCTGACCGCCCAGC

CTCTGTGCATTGGTTTCGGAACCGGGGCCAGGGCCGAGTCCCTGTCCGGG

AGTCCCCCCATCACCACTTAGCGGAAAGCTTCCTCTTCCTGCCCCAAGTC

AGCCCCCATGGACTCTGGGCCCTGGGGCTGCATCCTCACCTACAGAGATGG

CTTCAACGTCTCCATCATGTATAACCTCACTGTTCTGGGTCTGCTGGTGC

CCCGGGGCTCCGAGCCCAAATCTTGTGACAAAACTCACACAAGCCCACCG

AGCCCAGCACCTGAACTCCTGGGGGGATCCTCAGTCTTCCTCTTCCCCCC

-continued

AAAACCCAAGGACACCCTCATGATCTCCCGGACCCCTGAGGTCACATGCG

TGGTGGTGGACGTGAGCCACGAAGACCCTGAGGTCAAGTTCAACTGGTAC

GTGGACGGCGTGGAGGTGCATAATGCCAAGACAAAGCCGCGGGAGGAGCA

GTACCAGAGCACGTACCGTGTGGTCAGCGTCCTCACCGTCCTGCACCAGG

ACTGGCTGAATGGCAAGGAGTACAAGTGCAAGGTCTCCAACAAAGCCCTC

CCAGCCCCCATCGAGAAAACCATCTCCAAAGCCAAAGGGCAGCCCCGAGA

ACCACAGGTGTACACCCTGCCCCCATCTCGGGATGAGCTGACCAAGAACC

AGGTCAGCCTGACCTGCCTGGTCAAAGGCTTCTATCCCAGCGACATCGCC

GTGGAGTGGGAGAGCAATGGGCAGCCGGAGAACAACTACAAGACCACGCC

TCCCGTGCTGGACTCCGACGGCTCCTTCTTCCTATACAGCAAGCTCACCG

TGGACAAGAGCAGGTGGCAGCAGGGGAACGTCTTCTCATGCTCCGTGATG

CATGAGGCTCTGCACAACCACTACACGCAGAAGAGCCTCTCCCTGTCTCC

GGGTAAATGA

SEQ ID NO. 10:
CTLA-4 BsB human construct variant translated:
protein sequence 2 = (human CD80W84A/S190AS201A
(aa1-234)-G9-Lag-3R316/75E(aa27-262-IgG1aN596/
297Q(aa240-471)
MGHTRRQGTSPSKCPYLNFFQLLVLAGLSHFCSGVIHVTKEVKEVATLSC

GHNVSVEELAQTRIYWQKEKKMVLTMMSGDMNIAPEYKNRTIFDITNNLS

IVILALRPSDEGTYECVVLKYEKDAFKREHLAEVTLSVKADFPTPSISDF

EIPTSNIRRIICSTSGGFPEPHLSWLENGEELNAINTTVAQDPETELYAV

ASKLDFNMTTNHSFMCLIKYGHLRVNQTFNWNTTGGGGGGGGSGAEVPV

VWAQEGAPAQLPCSPTIPLQDLSLLRRAGVTWQHQPDSGPPAAAPGHPLA

PGPHPAAPSSWGPRPERYTVLSVGPGGLRSGRLPLQPRVQLDERGRQRGD

FSLWLRPARRADAGEYRAAVHLRDRALSCRLRLRLGQASMTASPPGSLRA

SDWVILNCSFSRPDRPASVHWFRNRGQGRVPVRESPHHHLAESFLFLPQV

SPMDSGPWGCILTYRDGFNVSIMYNLTVLGLLVPRGSEPKSCDKTHTSPP

SPAPELLGGSSVFLFPPKPKDTLMISRTPEVTCVVVDVSHEDPEVKFNWY

VDGVEVHNAKTKPREEQYQSTYRVVSVLTVLHQDWLNGKEYKCKVSNKAL

PAPIEKTISKAKGQPREPQVYTLPPSRDELTKNQVSLTCLVKGFYPSDIA

VEWESNGQPENNYKTTPPVLDSDGSFFLYSKLTVDKSRWQQGNVFSCSVM

HEALHNHYTQKSLSLSPGK

SEQ ID NO. 11:
CTLA-4 BsB human construct variant nucleotide
sequence 3 = (human CD80E196A/S190A(aa1-234)-
G9-Lag-3R316/75E(aa27-262-IgG1aN596/297Q
(aa240-471)
ATGGGCCACACACGGAGGCAGGGAACATCACCATCCAAGTGTCCATACCT

CAATTTCTTTCAGCTCTTGGTGCTGGCTGGTCTTTCTCACTTCTGTTCAG

GTGTTATCCACGTGACCAAGGAAGTGAAAGAAGTGGCAACGCTGTCCTGT

GGTCACAATGTTTCTGTTGAAGAGCTGGCACAAACTCGCATCTACTGGCA

AAAGGAGAAGAAAATGGTGCTGACTATGATGTCTGGGGACATGAATATAT

GGCCCGAGTACAAGAACCGGACCATCTTTGATATCACTAATAACCTCTCC

-continued

```
ATTGTGATCCTGGCTCTGCGCCCATCTGACGAGGGCACATACGAGTGTGT
TGTTCTGAAGTATGAAAAAGACGCTTTCAAGCGGGAACACCTGGCTGAAG
TGACGTTATCAGTCAAAGCTGACTTCCCTACACCTAGTATATCTGACTTT
GAAATTCCAACTTCTAATATTAGAAGGATAATTTGCTCAACCTCTGGAGG
TTTTCCAGAGCCTCACCTCTCCTGGTTGGAAAATGGAGAAGAATTAAATG
CCATCAACACAACAGTTGCCCAAGATCCTGAAACTGCCCTCTATGCTGTT
AGCAGCAAACTGGATTTCAATATGACAACCAACCACAGCTTCATGTGTCT
CATCAAGTATGGACATTTAAGAGTGAATCAGACCTTCAACTGGAATACAA
CCGGCGGTGGCGGCGGAGGCGGTGGCGGTTCCGGAGCTGAGGTCCCGGTG
GTGTGGGCCCAGGAGGGGGCTCCTGCCCAGCTCCCCTGCAGCCCCACAAT
CCCCCTCCAGGATCTCAGCCTTCTGCAAGAGCAGGGGTCACTTGGCAGC
ATCAGCCAGACAGTGGCCCGCCCGCTGCCGCCCCCGGCCATCCCCTGGCC
CCCGGCCCTCACCCGGCGGCGCCCTCCTCCTGGGGGCCCAGGCCCGAGCG
CTACACGGTGCTGAGCGTGGGTCCCGGAGGCCTGCGCAGCGGGAGGCTGC
CCCTGCAGCCCCGCGTCCAGCTGGATGAGCGCGGCCGGCAGCGCGGGGAC
TTCTCGCTATGGCTGCGCCCAGCCCGGCGCGCGGACGCCGGCGAGTACCG
CGCCGCGGTGCACCTCAGGGACCGCGCCCTCTCCTGCCGCCTCCGTCTGC
GCCTGGGCCAGGCCTCGATGACTGCCAGCCCCCAGGATCTCTCAGAGCC
TCCGACTGGGTCATTTTGAACTGCTCCTTCAGCCGCCCTGACCGCCCAGC
CTCTGTGCATTGGTTTCGGAACCGGGCCAGGGCCGAGTCCCTGTCCGGG
AGTCCCCCCATCACCACTTAGCGGAAAGCTTCCTCTTCCTGCCCCAAGTC
AGCCCCATGGACTCTGGGCCCTGGGGCTGCATCCTCACCTACAGAGATGG
CTTCAACGTCTCCATCATGTATAACCTCACTGTTCTGGGTCTGCTGGTGC
CCCGGGGCTCCGAGCCCAAATCTTGTGACAAAACTCACACAAGCCCACCG
AGCCCAGCACCTGAACTCCTGGGGGGATCCTCAGTCTTCCTCTTCCCCCC
AAAACCCAAGGACACCCTCATGATCTCCCGGACCCCTGAGGTCACATGCG
TGGTGGTGGACGTGAGCCACGAAGACCCTGAGGTCAAGTTCAACTGGTAC
GTGGACGGCGTGGAGGTGCATAATGCCAAGACAAAGCCGCGGGAGGAGCA
GTACCAGAGCACGTACCGTGTGGTCAGCGTCCTCACCGTCCTGCACCAGG
ACTGGCTGAATGGCAAGGAGTACAAGTGCAAGGTCTCCAACAAAGCCCTC
CCAGCCCCCATCGAGAAAACCATCTCCAAAGCCAAAGGGCAGCCCCGAGA
ACCACAGGTGTACACCCTGCCCCCATCTCGGGATGAGCTGACCAAGAACC
AGGTCAGCCTGACCTGCCTGGTCAAAGGCTTCTATCCCAGCGACATCGCC
GTGGAGTGGGAGAGCAATGGGCAGCCGGAGAACAACTACAAGACCACGCC
TCCCGTGCTGGACTCCGACGGCTCCTTCTTCCTATACAGCAAGCTCACCG
TGGACAAGAGCAGGTGGCAGCAGGGGAACGTCTTCTCATGCTCCGTGATG
CATGAGGCTCTGCACAACCACTACACGCAGAAGAGCCTCTCCCTGTCTCC
GGGTAAATGA
```

SEQ ID NO. 12:
CTLA-4 BsB human construct variant translated protein sequence 3 = (human CD80E196A/S190A (aa1-234)-G9-Lag-3R316/75E(aa27-262-IgG1 aN596/297Q(aa240-471)

MGHTRRQGTSPSKCPYLNFFQLLVLAGLSHFCSGVIHVTKEVKEVATLSC
GHNVSVEELAQTRIYWQKEKKMVLTMMSGDMNIWPEYKNRTIFDITNNLS
IVILALRPSDEGTYECVVLKYEKDAFKREHLAEVTLSVKADFPTPSISDF
EIPTSNIRRIICSTSGGFPEPHLSWLENGEELNAINTTVAQDPETALYAV
SSKLDFNMTTNHSFMCLIKYGHLRVNQTFNWNTTGGGGGGGGSGAEVPV
VWAQEGAPAQLPCSPTIPLQDLSLLRRAGVTWQHQPDSGPPAAAPGHPLA
PGPHPAAPSSWGPRPERYTVLSVGPGGLRSGRLPLQPRVQLDERGRQRGD
FSLWLRPARRADAGEYRAAVHLRDRALSCRLRLRLGQASMTASPPGSLRA
SDVVVILNCSFSRPDRPASVHWFRNRGQGRVPVRESPHHHLAESFLFLPQ
VSPMDSGPWGCILTYRDGFNVSIMYNLTVLGLLVPRGSEPKSCDKTHTSP
PSPAPELLGGSSVFLFPPKPKDTLMISRTPEVTCVVVDVSHEDPEVKFNW
YVDGVEVHNAKTKPREEQYQSTYRVVSVLTVLHQDWLNGKEYKCKVSNKA
LPAPIEKTISKAKGQPREPQVYTLPPSRDELTKNQVSLTCLVKGFYPSDI
AVEWESNGQPENNYKTTPPVLDSDGSFFLYSKLTVDKSRWQQGNVFSCSV
MHEALHNHYTQKSLSLSPGK

SEQ ID NO. 13:
CTLA-4 BsB human construct variant nucleotide sequence 4 = (human CD80E196A/S190AS201A(aa1-234)-G9-Lag-3R316/75E(aa27-262-IgG1a N596/297Q (aa240-471)

```
ATGGGCCACACACGGAGGCAGGGAACATCACCATCCAAGTGTCCATACCT
CAATTTCTTTCAGCTCTTGGTGCTGGCTGGTCTTTCTCACTTCTGTTCAG
GTGTTATCCACGTGACCAAGGAAGTGAAAGAAGTGGCAACGCTGTCCTGT
GGTCACAATGTTTCTGYFGAAGAGCTGGCACAAACTCGCATCTACTGGCA
AAAGGAGAAGAAAATGGTGCTGACTATGATGTCTGGGGACATGAATATAT
GGCCCGAGTACAAGAACCGGACCATCTTTGATATCACTAATAACCTCTCC
ATTGTGATCCTGGCTCTGCGCCCATCTGACGAGGGCACATACGAGTGTGT
TGTTCTGAAGTATGAAAAAGACGCTTTCAAGCGGGAACACCTGGCTGAAG
TGACGTTATCAGTCAAAGCTGACTTCCCTACACCTAGTATATCTGACTTT
GAAATTCCAACTTCTAATATTAGAAGGATAATTTGCTCAACCTCTGGAGG
TTTTCCAGAGCCTCACCTCTCCTGGTTGGAAAATGGAGAAGAATTAAATG
CCATCAACACAACAGTTGCCCAAGATCCTGAAACTGCCCTCTATGCTGTT
GCCAGCAAACTGGATTTCAATATGACAACCAACCACAGCTTCATGTGTCT
CATCAAGTATGGACATTTAAGAGTGAATCAGACCTTCAACTGGAATACAA
CCGGCGGTGGCGGCGGAGGCGGTGGCGGTTCCGGAGCTGAGGTCCCGGTG
GTGTGGGCCCAGGAGGGGGCTCCTGCCCAGCTCCCCTGCAGCCCCACAAT
CCCCCTCCAGGATCTCAGCCTTCTGCAAGAGCAGGGGTCACTTGGCAGC
ATCAGCCAGACAGTGGCCCGCCCGCTGCCGCCCCCGGCCATCCCCTGGCC
CCCGGCCCTCACCCGGCGGCGCCCTCCTCCTGGGGGCCCAGGCCCGAGCG
CTACACGGTGCTGAGCGTGGGTCCCGGAGGCCTGCGCAGCGGGAGGCTGC
CCCTGCAGCCCCGCGTCCAGCTGGATGAGCGCGGCCGGCAGCGCGGGGAC
```

```
TTCTCGCTATGGCTGCGCCCAGCCCGGCGCGCGGACGCCGGCGAGTACCG

CGCCGCGGTGCACCTCAGGGACCGCGCCCTCTCCTGCCGCCTCCGTCTGC

GCCTGGGCCAGGCCTCGATGACTGCCAGCCCCCCAGGATCTCTCAGAGCC

TCCGACTGGGTCATTTTGAACTGCTCCTTCAGCCGCCCTGACCGCCCAGC

CTCTGTGCATTGGTTTCGGAACCGGGCCAGGGCCGAGTCCCTGTCCGGG

AGTCCCCCCATCACCACTTAGCGGAAAGCTTCCTCTTCCTGCCCCAAGTC

AGCCCCATGGACTCTGGGCCCTGGGGCTGCATCCTCACCTACAGAGATGG

CTTCAACGTCTCCATCATGTATAACCTCACTGTTCTGGGTCTGCTGGTGC

CCCGGGGCTCCGAGCCCAAATCTTGTGACAAAACTCACACAAGCCCACCG

AGCCCAGCACCTGAACTCCTGGGGGGATCCTCAGTCTTCCTCTTCCCCCC

AAAACCCAAGGACACCCTCATGATCTCCCGGACCCCTGAGGTCACATGCG

TGGTGGTGGACGTGAGCCACGAAGACCCTGAGGTCAAGTTCAACTGGTAC

GTGGACGGCGTGGAGGTGCATAATGCCAAGACAAAGCCGCGGGAGGAGCA

GTACCAGAGCACGTACCGTGTGGTCAGCGTCCTCACCGTCCTGCACCAGG

ACTGGCTGAATGGCAAGGAGTACAAGTGCAAGGTCTCCAACAAAGCCCTC

CCAGCCCCCATCGAGAAAACCATCTCCAAAGCCAAAGGGCAGCCCCGAGA

ACCACAGGTGTACACCCTGCCCCCATCTCGGGATGAGCTGACCAAGAACC

AGGTCAGCCTGACCTGCCTGGTCAAAGGCTTCTATCCCAGCGACATCGCC

GTGGAGTGGGAGAGCAATGGGCAGCCGGAGAACAACTACAAGACCACGCC

TCCCGTGCTGGACTCCGACGGCTCCTTCTTCCTATACAGCAAGCTCACCG

TGGACAAGAGCAGGTGGCAGCAGGGGAACGTCTTCTCATGCTCCGTGATG

CATGAGGCTCTGCACAACCACTACACGCAGAAGAGCCTCTCCCTGTCTCC

GGGTAAATGA

SEQ ID NO. 14:
CTLA-4 BsB human construct variant translated
protein sequence 4 = (human CD80E196A/S190AS201A
(aa1-234)-G9-Lag-3R316/75E(aa27-262-IgG1aN596/
297Q(aa240-471)
MGHTRRQGTSPSKCPYLNFFQLLVLAGLSHFCSGVIHVTKEVKEVATLSC

GHNVSVEELAQTRIYWQKEKKMVLTMMSGDMNIWPEYKNRTIFDITNNLS

IVILALRPSDEGTYECVVLKYEKDAFKREHLAEVTLSVKADFPTPSISDF

EIPTSNIRRIICSTSGGFPEPHLSWLENGEELNAINTTVAQDPETALYAV

ASKLDFNMTTNHSFMCLIKYGHLRVNQTFNWNTTGGGGGGGGGSGAEVPV

VWAQEGAPAQLPCSPTIPLQDLSLLRRAGVTINQHQPDSGPPAAAPGHPL

APGPHPAAPSSWGPRPERYTVLSVGPGGLRSGRLPLQPRVQLDERGRQRG

DFSLWLRPARRADAGEYRAAVHLRDRALSCRLRLRLGQASMTASPPGSLR

ASDWVILNCSFSRPDRPASVHWFRNRGQGRVPVRESPHHHLAESFLFLPQ

VSPMDSGPWGCILTYRDGFNVSIMYNLTVLGLLVPRGSEPKSCDKTHTSP

PSPAPELLGGSSVFLFPPKPKDTLMISRTPEVTCVVVDVSHEDPEVKFNW

YVDGVEVHNAKTKPREEQYQSTYRVVSVLTVLHQDWLNGKEYKCKVSNKA

LPAPIEKTISKAKGQPREPQVYTLPPSRDELTKNQVSLTCLVKGFYPSDI

AVEWESNGQPENNYKTTPPVLDSDGSFFLYSKLTVDKSRWQQG NVFSCS

VMHEALHNHYTQKSLSLSPGK

SEQ ID NO. 15
Human CD80
MGHTRRQGTS PSKCPYLNFF QLLVLAGLSH FCSGVIHVTK

EVKEVATLSC GHNVSVEELA QTRIYWQKEK KMVLTMMSGD

MNIWPEYKNR TIFDITNNLS IVILALRPSD EGTYECVVLK

YEKDAFKREH LAEVTLSVKA DFPTPSISDF EIPTSNIRRI

ICSTSGGFPE PHLSWLENGE ELNAINTTVS QDPETELYAV

SSKLDFNMTT NHSFMCLIKY GHLRVNQTFN WNTTKQEHFP

DNLLPSWAIT LISVNGIFVI CCLTYCFAPR CRERRRNERL

RRESVRPV

SEQ ID NO. 16
BsBΔ (CD80wa-Fc) DNA = mouse CD80w88a(aa1-235)-
IgG2a(aa241-474)
Nucleotide sequence of mouse surrogate construct
(BsBΔ; CD80wa-Fc):
ATGGCTTGCAATTGTCAGTTGATGCAGGATACACCACTCCTCAAGTTTCC

ATGTCCAAGGCTCATTCTTCTCTTTGTGCTGCTGATTCGTCTTTCACAAG

TGTCTTCAGATGTTGATGAACAACTGTCCAAGTCAGTGAAAGATAAGGTA

TTGCTGCCTTGCCGTTACAACTCTCCTCATGAAGATGAGTCTGAAGACCG

AATCTACTGGCAAAAACATGACAAAGTGGTGCTGTCTGTCATTGCTGGGA

AACTAAAAGTGGCGCCCGAGTATAAGAACCGGACTTTATATGACAACACT

ACCTACTCTCTTATCATCCTGGGCCTGGTCCTTTCAGACCGGGGCACATA

CAGCTGTGTCGTTCAAAAGAAGGAAAGAGGAACGTATGAAGTTAAACACT

TGGCTTTAGTAAAGTTGTCCATCAAAGCTGACTTCTCTACCCCCAACATA

ACTGAGTCTGGAAACCCATCTGCAGACACTAAAAGGATTACCTGCTTTGC

TTCCGGGGGTTTCCCAAAGCCTCGCTTCTCTTGGTTGGAAAATGGAAGAG

AATTACCTGGCATCAATACGACAATTTCCCAGGATCCTGAATCTGAATTG

TACACCATTAGTAGCCAACTAGATTTCAATACGACTCGCAACCACACCAT

TAAGTGTCTCATTAAATATGGAGATGCTCACGTGTCAGAGGACTTCACCT

GGGAGCCCAGAGGGCCCACAATCAAGCCCTGTCCTCCATGCAAATGCCCA

GCACCTAACCTCTTGGGTGGACCATCCGTCTTCATCTTCCCTCCAAAGAT

CAAGGATGTACTCATGATCTCCCTGAGCCCCATGGTCACATGTGTGGTGG

TGGATGTGAGCGAGGATGACCCAGATGTCCAGATCAGCTGGTTCGTGAAC

AACGTGGAAGTACTCACAGCTCAGACACAAACCCATAGAGAGGATTACAA

CAGTACTCTCCGGGTGGTCAGTGCCCTCCCCATCCAGCACCAGGACTGGA

TGAGTGGCAAGGAGTTCAAATGCAAGGTCAACAACAAAGCCCTCCCAGCG

CCCATCGAGAGAACCATCTCAAAACCCAAAGGGTCAGTAAGAGCTCCACA

GGTATATGTCTTGCCTCCACCAGAAGAAGAGATGACTAAGAAACAGGTCA

CTCTGACCTGCATGGTCACAGACTTCATGCCTGAAGACATTTACGTGGAG

TGGACCAACAACGGGAAAACAGAGCTAAACTACAAGAACACTGAACCAGT

CCTGGACTCTGATGGTTCTTACTTCATGTACAGCAAGCTGAGAGTGGAAA

AGAAGAACTGGGTGGAAAGAAATAGCTACTCCTGCTCAGTGGTCCACGAG

GGTCTGCACAATCACCACGAGACTAAGAGCTTCTCCCGGACTCCGGGTAA
```

```
                        -continued
AGGCGGTGGCGGCGGAGGCGGTGGCGGTGGGCCTGGGAAAGAGCTGGGTC

TGGAGCCCGTAGCCCACCATCACCATCATCACTGA

SEQ ID NO. 17
BsBA (CD80wa-Fc) Protein = mouse CD80w88a(aa1-
235)-IgG2a(aa241-474)
Translated protein sequence of mouse surrogate
construct (BsBΔ; CD80wa-Fc):
MACNCQLMQDTPLLKFPCPRLILLFVLLIRLSQVSSDVDEQLSKSVKDKV

LLPCRYNSPHEDESEDRIYWQKHDKVVLSVIAGKLKVAPEYKNRTLYDNT

TYSLIILGLVLSDRGTYSCVVQKKERGTYEVKHLALVKLSIKADFSTPNI

TESGNPSADTKRITCFASGGFPKPRFSWLENGRELPGINTTISQDPESEL

YTISSQLDFNTTRNHTIKCLIKYGDAHVSEDFTWEPRGPTIKPCPPCKCP

APNLLGGPSVFIFPPKIKDVLMISLSPMVTCVVVDVSEDDPDVQISWFVN

NVEVLTAQTQTHREDYNSTLRVVSALPIQHQDWMSGKEFKCKVNNKALPA

PIERTISKPKGSVRAPQVYVLPPPEEEMTKKQVTLTCMVTDFMPEDIYVE

WTNNGKTELNYKNTEPVLDSDGSYFMYSKLRVEKKNWVERNSYSCSVVHE

GLHNHHTTKSFSRTPGKGGGGGGGGGPGKELGLEPVAHHHHHH
```

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

REFERENCES

The following documents are cited herein.

Allan, S. E., R. Broady, S. Gregori, M. E. Himmel, N. Locke, M. G. Roncarolo, R. Bacchetta, and M. K. Levings. 2008. CD4+T-regulatory cells: toward therapy for human diseases. Immunol Rev 223:391-421.

Anderson, B. E., J. M. McNiff, C. Matte, I. Athanasiadis, W. D. Shlomchik, and M. J. Shlomchik. 2004. Recipient CD4+ T cells that survive irradiation regulate chronic graft-versus-host disease. Blood 104:1565-1573.

Anderson, M. S., and J. A. Bluestone. 2005. The NOD mouse: a model of immune dysregulation. Annu Rev Immunol 23:447-485.

Barnden, M. J., J. Allison, W. R. Heath, and F. R. Carbone. 1998. Defective TCR expression in transgenic mice constructed using cDNA-based alpha- and beta-chain genes under the control of heterologous regulatory elements. Immunol Cell Biol 76:34-40.

Baroja, M. L., L. Vijayakrishnan, E. Bettelli, P. J. Darlington, T. A. Chau, V. Ling, M. Collins, B. M. Carreno, J. Madrenas, and V. K. Kuchroo. 2002. Inhibition of CTLA-4 function by the regulatory subunit of serine/threonine phosphatase 2A. J Immunol 168:5070-5078.

Bettini, M., A. L. Szymczak-Workman, K. Forbes, A. H. Castellaw, M. Selby, X. Pan, C. G. Drake, A. J. Korman, and D. A. Vignali. 2011. Cutting edge: accelerated autoimmune diabetes in the absence of LAG-3. J Immunol 187:3493-3498.

Blair, P. J., J. L. Riley, B. L. Levine, K. P. Lee, N. Craighead, T. Francomano, S. J. Perfetto, G. S. Gray, B. M. Carreno, and C. H. June. 1998. CTLA-4 ligation delivers a unique signal to resting human CD4 T cells that inhibits interleukin-2 secretion but allows Bcl-X(L) induction. J Immunol 160:12-15.

Bluestone, J. A., C. R. Mackay, J. J. O'Shea, and B. Stockinger. 2009. The functional plasticity of T cell subsets. Nat Rev Immunol 9:811-816.

Caretto, D., S. D. Katzman, A. V. Villarino, E. Gallo, and A. K. Abbas. 2010. Cutting edge: the Th1 response inhibits the generation of peripheral regulatory T cells. J Immunol 184:30-34.

Chatenoud, L., E. Thervet, J. Primo, and J. F. Bach. 1994. Anti-CD3 antibody induces long-term remission of overt autoimmunity in nonobese diabetic mice. Proc Natl Acad Sci U S A 91:123-127.

Chen, W., W. Jin, N. Hardegen, K. J. Lei, L. Li, N. Marinos, G. McGrady, and S. M. Wahl. 2003. Conversion of peripheral CD4+CD25− naive T cells to CD4+CD25+ regulatory T cells by TGF-beta induction of transcription factor Foxp3. J Exp Med 198:1875-1886.

Chuang, E., T. S. Fisher, R. W. Morgan, M. D. Robbins, J. M. Duerr, M. G. Vander Heiden, J. P. Gardner, J. E. Hambor, M. J. Neveu, and C. B. Thompson. 2000. The CD28 and CTLA-4 receptors associate with the serine/threonine phosphatase PP2A. Immunity 13:313-322.

Daniel, C., B. Weigmann, R. Bronson, and H. von Boehmer. 2011. Prevention of type 1 diabetes in mice by tolerogenic vaccination with a strong agonist insulin mimetope. J Exp Med 208:1501-1510.

Fife, B. T., M. D. Griffin, A. K. Abbas, R. M. Locksley, and J. A. Bluestone. 2006. Inhibition of T cell activation and autoimmune diabetes using a B cell surface-linked CTLA-4 agonist. J Clin Invest 116:2252-2261.

Gonzalez-Rey, E., A. Fernandez-Martin, A. Chorny, and M. Delgado. 2006. Vasoactive intestinal peptide induces CD4+,CD25+ T regulatory cells with therapeutic effect in collagen-induced arthritis. Arthritis Rheum 54:864-876.

Griffin, M. D., D. K. Hong, P. O. Holman, K. M. Lee, M. J. Whitters, S. M. O'Herrin, F. Fallarino, M. Collins, D. M. Segal, T. F. Gajewski, D. M. Kranz, and J. A. Bluestone. 2000. Blockade of T cell activation using a surface-linked single-chain antibody to CTLA-4 (CD152). J Immunol 164:4433-4442.

Grohmann, U., C. Orabona, F. Fallarino, C. Vacca, F. Calcinaro, A. Falorni, P. Candeloro, M. L. Belladonna, R. Bianchi, M. C. Fioretti, and P. Puccetti. 2002. CTLA-4-Ig regulates tryptophan catabolism in vivo. Nat Immunol 3:1097-1101.

Guntermann, C., and D. R. Alexander. 2002. CTLA-4 suppresses proximal TCR signaling in resting human CD4 (+) T cells by inhibiting ZAP-70 Tyr(319) phosphorylation: a potential role for tyrosine phosphatases. J Immunol 168: 4420-4429.

Ise, W., M. Kohyama, K. M. Nutsch, H. M. Lee, A. Suri, E. R. Unanue, T. L. Murphy, and K. M. Murphy. 2010. CTLA-4 suppresses the pathogenicity of self antigen-specific T cells by cell-intrinsic and cell-extrinsic mechanisms. Nat Immunol 11:129-135.

Jain, N., H. Nguyen, C. Chambers, and J. Kang. 2010. Dual function of CTLA-4 in regulatory T cells and conventional T cells to prevent multiorgan autoimmunity. Proc Natl Acad Sci USA 107:1524-1528.

Jiang, S., R. I. Lechler, and G. Lombardi. 2006. CD4+ CD25+ regulatory T-cell therapy. Expert review of clinical immunology 2:387-392.

Karandikar, N. J., C. L. Vanderlugt, T. L. Walunas, S. D. Miller, and J. A. Bluestone. 1996. CTLA-4: a negative regulator of autoimmune disease. J Exp Med 184:783-788.

Karman, J., J. L. Jiang, N. Gumlaw, H. Zhao, J. Campos-Rivera, J. Sancho, J. Zhang, C. Jiang, S. H. Cheng, and Y. Zhu. 2012. Ligation of cytotoxic T lymphocyte antigen-4 to the TCR inhibits T cell activation and directs differentiation into FOXP3+ regulatory T cells. J Biol Chem Kastner, L., D. Dwyer, and F. X. Qin. 2010. Synergistic effect of IL-6 and IL-4 in driving fate revision of natural Foxp3+ regulatory T cells. J Immunol 185:5778-5786.

Kehrl, J. H., L. M. Wakefield, A. B. Roberts, S. Jakowlew, M. Alvarez-Mon, R. Derynck, M. B. Sporn, and A. S. Fauci. 1986. Production of transforming growth factor beta by human T lymphocytes and its potential role in the regulation of T cell growth. J Exp Med 163:1037-1050.

Koenen, H. J., R. L. Smeets, P. M. Vink, E. van Rijssen, A. M. Boots, and I. Joosten. 2008. Human CD25highFoxp3pos regulatory T cells differentiate into IL-17-producing cells. Blood 112:2340-2352.

Krummel, M. F., and J. P. Allison. 1995. CD28 and CTLA-4 have opposing effects on the response of T cells to stimulation. J Exp Med 182:459-465.

Krummel, M. F., and J. P. Allison. 1996. CTLA-4 engagement inhibits IL-2 accumulation and cell cycle progression upon activation of resting T cells. J Exp Med 183:2533-2540.

Lenschow, D. J., S. C. Ho, H. Sattar, L. Rhee, G. Gray, N. Nabavi, K. C. Herold, and J. A. Bluestone. 1995. Differential effects of anti-B7-1 and anti-B7-2 monoclonal antibody treatment on the development of diabetes in the nonobese diabetic mouse. J Exp Med 181:1145-1155.

Linsley, P. S., and P. Golstein. 1996. Lymphocyte activation: T-cell regulation by CTLA-4. Curr Biol 6:398-400.

Linsley, P. S., J. L. Greene, W. Brady, J. Bajorath, J. A. Ledbetter, and R. Peach. 1994. Human B7-1 (CD80) and B7-2 (CD86) bind with similar avidities but distinct kinetics to CD28 and CTLA-4 receptors. Immunity 1:793-801.

Marie, J. C., J. J. Letterio, M. Gavin, and A. Y. Rudensky. 2005. TGF-beta1 maintains suppressor function and Foxp3 expression in CD4+CD25+ regulatory T cells. J Exp Med 201:1061-1067.

Masteller, M. R. Warner, Q. Tang, K. V. Tarbell, H. McDevitt, and J. A. Bluestone. 2005. Expansion of functional endogenous antigen-specific CD4+CD25+ regulatory T cells from nonobese diabetic mice. J Immunol 175:3053-3059.

McDevitt, H., S. Singer, and R. Tisch. 1996. The role of MHC class II genes in susceptibility and resistance to type I diabetes mellitus in the NOD mouse. Hormone and metabolic research =Hormon-und Stoffwcchsclforschung=Hormoncs ct mctabolismc 28:287-288.

Murai, M., O. Turovskaya, G. Kim, R. Madan, C. L. Karp, H. Cheroutre, and M. Kronenberg. 2009. Interleukin 10 acts on regulatory T cells to maintain expression of the transcription factor Foxp3 and suppressive function in mice with colitis. Nat Immunol 10:1178-1184.

Nishio, J., M. Feuerer, J. Wong, D. Mathis, and C. Benoist. 2010. Anti-CD3 therapy permits regulatory T cells to surmount T cell receptor-specified peripheral niche constraints. J Exp Med 207:1879-1889.

Ohata, J., T. Miura, T. A. Johnson, S. Hori, S. F. Ziegler, and H. Kohsaka. 2007. Enhanced efficacy of regulatory T cell transfer against increasing resistance, by elevated Foxp3 expression induced in arthritic murine hosts. Arthritis Rheum 56:2947-2956.

Onodera, T., M. H. Jang, Z. Guo, M. Yamasaki, T. Hirata, Z. Bai, N. M. Tsuji, D. Nagakubo, O. Yoshie, S. Sakaguchi, O. Takikawa, and M. Miyasaka. 2009. Constitutive expression of IDO by dendritic cells of mesenteric lymph nodes: functional involvement of the CTLA-4/B7 and CCL22/CCR4 interactions. J Immunol 183:5608-5614.

Paterson, A. M., and A. H. Sharpe. 2010. Taming tissue-specific T cells: CTLA-4 reins in self-reactive T cells. Nat Immunol 11:109-111.

Pentcheva-Hoang, T., J. G. Egen, K. Wojnoonski, and J. P. Allison. 2004. B7-1 and B7-2 selectively recruit CTLA-4 and CD28 to the immunological synapse. Immunity 21:401-413.

Pontow, S. E., V. Kery, and P. D. Stahl. 1992. Mannose receptor. Int Rev Cytol 137B:221-244.

Qu, H. Q., J. P. Bradfield, S. F. Grant, H. Hakonarson, and C. Polychronakos. 2009. Remapping the type I diabetes association of the CTLA4 locus. Genes and immunity 10 Suppl 1:S27-32.

Riley, J. L., C. H. June, and B. R. Blazar. 2009. Human T regulatory cell therapy: take a billion or so and call me in the morning. Immunity 30:656-665.

Roncarolo, M. G., S. Gregori, M. Battaglia, R. Bacchetta, K. Fleischhauer, and M. K. Levings. 2006. Interleukin-10-secreting type 1 regulatory T cells in rodents and humans. Immunol Rev 212:28-50.

Roopenian, D. C., and S. Akilesh. 2007. FcRn: the neonatal Fc receptor comes of age. Nat Rev Immunol 7:715-725.

Sakaguchi, S., N. Sakaguchi, M. Asano, M. Itoh, and M. Toda. 1995. Immunologic self-tolerance maintained by activated T cells expressing IL-2 receptor alpha-chains (CD25). Breakdown of a single mechanism of self-tolerance causes various autoimmune diseases. J Immunol 155:1151-1164.

Salomon, B., D. J. Lenschow, L. Rhee, N. Ashourian, B. Singh, A. Sharpe, and J. A. Bluestone. 2000. B7/CD28 costimulation is essential for the homeostasis of the CD4+ CD25+ immunoregulatory T cells that control autoimmune diabetes. Immunity 12:431-440.

Shoda, L. K., D. L. Young, S. Ramanujan, C. C. Whiting, M. A. Atkinson, J. A. Bluestone, G. S. Eisenbarth, D. Mathis, A. A. Rossini, S. E. Campbell, R. Kahn, and H. T. Kreuwel. 2005. A comprehensive review of interventions in the NOD mouse and implications for translation. Immunity 23:115-126.

Simon, G., M. Parker, V. Ramiya, C. Wasserfall, Y. Huang, D. Bresson, R. F. Schwartz, M. Campbell-Thompson, L. Tenace, T. Brusko, S. Xue, A. Scaria, M. Lukason, S. Eisenbeis, J. Williams, M. Clare-Salzler, D. Schatz, B. Kaplan, M. Von Herrath, K. Womer, and M. A. Atkinson. 2008. Murine antithymocyte globulin therapy alters disease progression in NOD mice by a time-dependent induction of immunoregulation. Diabetes 57:405-414.

Steinman, R. M., D. Hawiger, and M. C. Nussenzweig. 2003. Tolerogenic dendritic cells. Annu Rev Immunol 21:685-711.

Tang, Q., J. A. Bluestone, and S. M. Kang. 2012. CD4 (+)Foxp3(+) regulatory T cell therapy in transplantation. Journal of molecular cell biology 4:11-21.

Tang, Q., K. J. Henriksen, M. Bi, E. B. Finger, G. Szot, J. Ye, E. L. Masteller, H. McDevitt, M. Bonyhadi, and J. A. Bluestone. 2004. In vitro-expanded antigen-specific regulatory T cells suppress autoimmune diabetes. J Exp Med 199:1455-1465.

Tang, Q., K. J. Henriksen, E. K. Boden, A. J. Tooley, J. Ye, S. K. Subudhi, X. X. Zheng, T. B. Strom, and J. A. Bluestone. 2003. Cutting edge: CD28 controls peripheral homeostasis of CD4+CD25+ regulatory T cells. J Immunol 171:3348-3352.

Tarbell, K. V., L. Petit, X. Zuo, P. Toy, X. Luo, A. Mqadmi, H. Yang, M. Suthanthiran, S. Mojsov, and R. M. Steinman. 2007. Dendritic cell-expanded, islet-specific CD4+CD25+ CD62L+ regulatory T cells restore normoglycemia in diabetic NOD mice. J Exp Med 204:191-201.

Taylor, P. A., C. J. Lees, and B. R. Blazar. 2002. The infusion of ex vivo activated and expanded CD4(+)CD25(+) immune regulatory cells inhibits graft-versus-host disease lethality. Blood 99:3493-3499.

Tivol, E. A., F. Borriello, A. N. Schweitzer, W. P. Lynch, J. A. Bluestone, and A. H. Sharpe. 1995. Loss of CTLA-4 leads to massive lymphoproliferation and fatal multiorgan tissue destruction, revealing a critical negative regulatory role of CTLA-4. Immunity 3:541-547.

Tsunawaki, S., M. Sporn, A. Ding, and C. Nathan. 1988. Deactivation of macrophages by transforming growth factor-beta. Nature 334:260-262.

Ueda, H., J. M. Howson, L. Esposito, J. Heward, H. Snook, G. Chamberlain, D. B. Rainbow, K. M. Hunter, A. N. Smith, G. Di Genova, M. H. Herr, I. Dahlman, F. Payne, D. Smyth, C. Lowe, R. C. Twells, S. Howlett, B. Healy, S. Nutland, H. E. Rance, V. Everett, L. J. Smink, A. C. Lam, H. J. Cordell, N. M. Walker, C. Bordin, J. Hulme, C. Motzo, F. Cucca, J. F. Hess, M. L. Metzker, J. Rogers, S. Gregory, A. Allahabadia, R. Nithiyananthan, E. Tuomilchto-Wolf, J. Tuomilehto, P. Bingley, K. M. Gillespie, D. E. Undlien, K. S. Ronningen, C. Guja, C. Ionescu-Tirgoviste, D. A. Savage, A. P. Maxwell, D. J. Carson, C. C. Patterson, J. A. Franklyn, D. G. Clayton, L. B. Peterson, L. S. Wicker, J. A. Todd, and S. C. Gough. 2003. Association of the T-cell regulatory gene CTLA4 with susceptibility to autoimmune disease. Nature 423:506-511.

Vergani, A., F. D'Addio, M. Jurewicz, A. Petrelli, T. Watanabe, K. Liu, K. Law, C. Schuetz, M. Carvello, E. Orsenigo, S. Deng, S. J. Rodig, J. M. Ansari, C. Staudacher, R. Abdi, J. Williams, J. Markmann, M. Atkinson, M. H. Sayegh, and P. Fiorina. 2010. A novel clinically relevant strategy to abrogate autoimmunity and regulate alloimmunity in NOD mice. Diabetes 59:2253-2264.

Wahl, S. M., N. McCartney-Francis, J. B. Allen, E. B. Dougherty, and S. F. Dougherty. 1990. Macrophage production of TGF-beta and regulation by TGF-beta. Ann N Y Acad Sci 593:188-196.

Walunas, T. L., C. Y. Bakker, and J. A. Bluestone. 1996. CTLA-4 ligation blocks CD28-dependent T cell activation. J Exp Med 183:2541-2550.

Walunas, T. L., and J. A. Bluestone. 1998. CTLA-4 regulates tolerance induction and T cell differentiation in vivo. J Immunol 160:3855-3860.

Walunas, T. L., D. J. Lenschow, C. Y. Bakker, P. S. Linsley, G. J. Freeman, J. M. Green, C. B. Thompson, and J. A. Bluestone. 1994. CTLA-4 can function as a negative regulator of T cell activation. Immunity 1:405-413.

Waterhouse, P., J. M. Penninger, E. Timms, A. Wakeham, A. Shahinian, K. P. Lee, C. B. Thompson, H. Griesser, and T. W. Mak. 1995. Lymphoproliferative disorders with early lethality in mice deficient in Ctla-4. Science 270:985-988.

Weigel, P. H. 1994. Galactosyl and N-acetylgalactosaminyl homeostasis: a function for mammalian asialoglycoprotein receptors. BioEssays: news and reviews in molecular, cellular and developmental biology 16:519-524.

Wicker, L. S., J. A. Todd, and L. B. Peterson. 1995. Genetic control of autoimmune diabetes in the NOD mouse. Annu Rev Immunol 13:179-200.

Yamagiwa, S., J. D. Gray, S. Hashimoto, and D. A. Horwitz. 2001. A role for TGF-beta in the generation and expansion of CD4+CD25+ regulatory T cells from human peripheral blood. J Immunol 166:7282-7289.

Zhao, D., C. Zhang, T. Yi, C. L. Lin, I. Todorov, F. Kandeel, S. Forman, and D. Zeng. 2008. In vivo-activated CD103+CD4+regulatory T cells ameliorate ongoing chronic graft-versus-host disease. Blood 112:2129-2138.

Zheng, S. G., J. D. Gray, K. Ohtsuka, S. Yamagiwa, and D. A. Horwitz. 2002. Generation ex vivo of TGF-beta-producing regulatory T cells from CD4+CD25− precursors. J Immunol 169:4183-4189.

Zhou, X., S. Bailey-Bucktrout, L. T. Jeker, and J. A. Bluestone. 2009a. Plasticity of CD4(+) FoxP3(+) T cells. Curr Opin Immunol 21:281-285.

Zhou, X., S. L. Bailey-Bucktrout, L. T. Jeker, C. Penaranda, M. Martinez-Llordella, M. Ashby, M. Nakayama, W. Rosenthal, and J. A. Bluestone. 2009b. Instability of the transcription factor Foxp3 leads to the generation of pathogenic memory T cells in vivo. Nat Immunol 10:1000-1007.

The invention claimed is:

1. A method of tolerizing a T-cell to an antigen, comprising contacting said T-cell with an antigen-presenting cell which is presenting a peptide derived from said antigen complexed to a MHC molecule and a bispecific fusion protein comprising a ligand specific for CTLA-4 and a ligand specific for a peptide-MHC class II (pMHCII) complex, wherein the T-cell expresses a T-cell receptor (TCR) and cell surface CTLA-4, and the ligand specific for CTLA-4 is selected from the group consisting of CD80

(B7-1), CD86 (B7-2), and mutants thereof with greater binding avidity for CTLA-4 than CD28, thereby crosslinking CTLA-4 to the pMHCII complex and the TCR.

2. The method of claim 1, wherein the method is used to treat an autoimmune disease.

3. The method according to claim 2, wherein the bispecific fusion protein is administered in combination with a further immune suppressant or modulator.

4. The method according to claim 2, wherein the autoimmune disease is selected from type 1 diabetes (T1D), Systemic Lupus Erythematosus (SLE), Rheumatoid Arthritis RA, inflammatory bowel disease (IBD), ulcerative colitis (UC), Crohn's disease (CD), multiple sclerosis (MS), scleroderma, pemphigus vulgaris (PV), psoriasis, atopic dermatitis, celiac disease, Chronic Obstructive Lung disease, Hashimoto's thyroiditis, Graves' disease (thyroid), Sjogren's syndrome, Guillain-Barré syndrome, Goodpasture's syndrome, Addison's disease, Wegener's granulomatosis, primary biliary sclerosis, sclerosing cholangitis, autoimmune hepatitis, polymyalgia rheumatica, Raynaud's phenomenon, temporal arteritis, giant cell arteritis, autoimmune hemolytic anemia, pernicious anemia, polyarteritis nodosa, Behcet's disease, primary biliary cirrhosis, uveitis, myocarditis, rheumatic fever, ankylosing spondylitis, glomerulonephritis, sarcoidosis, dermatomyositis, myasthenia gravis, polymyositis, alopecia areata, and vitiligo.

5. The method of claim 2, wherein the ligand specific for the pMHCII complex is selected from an anti-MHC antibody and LAG-3.

6. The method of claim 2, wherein the ligand specific for CTLA-4 and the ligand specific for the pMHCII complex are spaced apart by a linker.

7. The method of claim 6, wherein the linker is one or more of a polyamino acid sequence and an antibody Fc domain.

8. The method of claim 7, wherein the polyamino acid sequence is G9 (Gly-9).

9. The method of claim 2, wherein the ligand specific for CTLA-4 is CD80.

10. The method of claim 9, wherein CD80 is mutated to increase binding avidity or specificity for CTLA-4 over CD28.

11. The method of claim 10, wherein CD80 is human CD80 comprising at least one of mutations W84A, K71G, K71V, S109G, R123S, R123D, G124L, S190A, S201A, R63A, M81A, N97A and E196A.

12. The method of claim 11, wherein CD80 comprises the mutation W84A or E196A of human CD80.

13. The method of claim 2, wherein the ligand specific for the pMHCII complex is LAG-3.

14. The method of claim 13, wherein LAG-3 is mutated to increase specificity for pMHCII.

15. The method of claim 14, wherein LAG-3 is human LAG-3 comprising at least one of mutations R73E, R75A, R75E and R76E.

16. The method of claim 14, wherein LAG-3 comprises the mutation R75A or R75E.

* * * * *